(12) United States Patent
Cini et al.

(10) Patent No.: US 10,376,582 B2
(45) Date of Patent: Aug. 13, 2019

(54) BUFFER FORMULATIONS FOR ENHANCED ANTIBODY STABILITY

(71) Applicant: Outlook Therapeutics, Inc., Cranbury, NJ (US)

(72) Inventors: John Cini, Cranbury, NJ (US); Athena Nagi, Cranbury, NJ (US); Maria Taddei, Cranbury, NJ (US)

(73) Assignee: Outlook Therapeutics, Inc., Cranbury, NJ (US)

( * ) Notice: Subject to any disclaimer, the term of this patent is extended or adjusted under 35 U.S.C. 154(b) by 130 days.

(21) Appl. No.: 15/025,088

(22) PCT Filed: Oct. 16, 2014

(86) PCT No.: PCT/US2014/060810
§ 371 (c)(1),
(2) Date: Mar. 25, 2016

(87) PCT Pub. No.: WO2015/057910
PCT Pub. Date: Apr. 23, 2015

(65) Prior Publication Data
US 2016/0235845 A1    Aug. 18, 2016

Related U.S. Application Data

(60) Provisional application No. 61/891,485, filed on Oct. 16, 2013.

(51) Int. Cl.
| | | |
|---|---|---|
| A61K 39/395 | (2006.01) |
| C07K 16/24 | (2006.01) |
| A61K 9/08 | (2006.01) |
| A61K 47/02 | (2006.01) |
| A61K 47/12 | (2006.01) |
| A61K 47/26 | (2006.01) |

(52) U.S. Cl.
CPC .......... *A61K 39/39591* (2013.01); *A61K 9/08* (2013.01); *A61K 47/02* (2013.01); *A61K 47/12* (2013.01); *A61K 47/26* (2013.01); *C07K 16/241* (2013.01); *C07K 2317/51* (2013.01); *C07K 2317/515* (2013.01); *C07K 2317/52* (2013.01)

(58) Field of Classification Search
None
See application file for complete search history.

(56) References Cited

U.S. PATENT DOCUMENTS

| | | |
|---|---|---|
| 6,090,382 A | 7/2000 | Salfeld et al. |
| 6,258,562 B1 | 6/2001 | Salfeld et al. |
| 7,223,394 B2 | 5/2007 | Safeld et al. |
| 7,541,031 B2 | 6/2009 | Safeld et al. |
| 7,863,426 B2 | 1/2011 | Wan et al. |
| 7,919,264 B2 | 4/2011 | Maksymowych et al. |
| 7,935,808 B2 | 5/2011 | Gion et al. |
| 8,034,906 B2 | 10/2011 | Borhani et al. |
| 8,067,547 B2 | 11/2011 | Ewert et al. |
| 8,092,998 B2 | 1/2012 | Stuhlmüller et al. |
| 8,093,045 B2 | 1/2012 | Pla et al. |
| 8,187,836 B2 | 5/2012 | Hsieh et al. |
| 8,206,714 B2 | 6/2012 | Salfeld et al. |
| 8,216,583 B2 | 7/2012 | Kruase et al. |
| 8,231,876 B2 | 7/2012 | Wan et al. |
| 8,258,268 B2 | 9/2012 | Wu et al. |
| 8,372,400 B2 | 2/2013 | Salfeld et al. |
| 8,410,259 B2 | 4/2013 | Gion et al. |
| 8,414,894 B2 | 4/2013 | Salfeld et al. |
| 8,420,081 B2 | 4/2013 | Fraunhofer et al. |
| 8,455,219 B2 | 6/2013 | Hsieh et al. |
| 8,652,474 B2 | 2/2014 | Harris et al. |
| 8,663,945 B2 | 3/2014 | Pla et al. |
| 8,679,061 B2 | 3/2014 | Julian et al. |
| 8,715,664 B2 | 5/2014 | Hoffman et al. |
| 8,747,854 B2 | 6/2014 | Okun et al. |
| 8,753,633 B2 | 6/2014 | Salfeld et al. |
| 8,753,839 B2 | 6/2014 | Fraunhofer et al. |
| 8,795,670 B2 | 8/2014 | Krause et al. |
| 8,802,100 B2 | 8/2014 | Krause et al. |
| 8,802,101 B2 | 8/2014 | Krause et al. |
| 8,802,102 B2 | 8/2014 | Krause et al. |
| 8,808,700 B1 | 8/2014 | Hoffman et al. |
| 8,821,865 B2 | 9/2014 | Neu et al. |

(Continued)

FOREIGN PATENT DOCUMENTS

| | | |
|---|---|---|
| CN | 102078608 A | 6/2011 |
| CN | 105779394 A | 7/2016 |

(Continued)

OTHER PUBLICATIONS

Allen, J.G. et al. (2016) "Facile Modulation of Antibody Fucosylation with Small Molecule Fucostatin Inhibitors and Cocrystal Structure with GDP-Mannose 4,6-Dehydratase" *ACS Chem Biol*, 11:2734-2743.

Bandyopadhyay, S. et al. (2015) "Physicochemical and functional characterization of a biosimilar adalimumab ZRC-3197" *Biosimilars*, 5:1-18.

Beck, A. et al. (Apr. 2012) "Biosimilar, Biobetter, and Next Generation Antibody Characterization by Mass Spectrometry" *Anal Chem*, 84(11):4637-4646.

Beck, A. et al. (2015) "Cutting-edge mass spectrometry characterization of originator, biosimilar and biobetter antibodies" *J Mass Spectrom*, 50:285-297.

Butler, M. et al. (2012) "Recent advances in technology supporting biopharmaceutical production from mammalian cells" *Appl Microbiol Biotechnol*, 96:885-894.

(Continued)

*Primary Examiner* — Yunsoo Kim
(74) *Attorney, Agent, or Firm* — Cooley LLP; Matthew Pavao

(57) ABSTRACT

The invention provides buffered formulations of adalimumab. The formulations comprise a buffer comprising an acetate salt, mannitol, glacial acetic acid, sodium chloride, and polysorbate 80. The formulations have an acidic pH, and enhance the thermal, conformational and colloidal stability of antibodies, including the adalimumab antibody.

82 Claims, 25 Drawing Sheets

Specification includes a Sequence Listing.

(56) References Cited

U.S. PATENT DOCUMENTS

| | | |
|---|---|---|
| 8,846,046 B2 | 9/2014 | Kaymakcalan et al. |
| 8,883,146 B2 | 11/2014 | Fraunhofer et al. |
| 8,883,156 B2 | 11/2014 | Wan et al. |
| 8,889,135 B2 | 11/2014 | Fischkoff et al. |
| 8,889,136 B2 | 11/2014 | Hoffman et al. |
| 8,895,009 B2 | 11/2014 | Wan et al. |
| 8,895,709 B2 | 11/2014 | Hickman et al. |
| 8,906,372 B2 | 12/2014 | Wan et al. |
| 8,906,373 B2 | 12/2014 | Banerjee et al. |
| 8,906,646 B2 | 12/2014 | Pla et al. |
| 8,911,737 B2 | 12/2014 | Fischkoff et al. |
| 8,911,741 B2 | 12/2014 | Krause et al. |
| 8,911,964 B2 | 12/2014 | Pla et al. |
| 8,916,153 B2 | 12/2014 | Wan et al. |
| 8,916,157 B2 * | 12/2014 | Krause .................... A61K 9/19 424/158.1 |
| 8,916,158 B2 | 12/2014 | Krause et al. |
| 8,932,591 B2 | 1/2015 | Krause et al. |
| 8,940,305 B2 | 1/2015 | Krause et al. |
| 8,961,973 B2 | 2/2015 | Hoffman et al. |
| 8,961,974 B2 | 2/2015 | Hoffman et al. |
| 8,974,790 B2 | 3/2015 | Fischkoff et al. |
| 8,986,693 B1 | 3/2015 | Hoffman et al. |
| 8,992,926 B2 | 3/2015 | Fischkoff et al. |
| 8,999,337 B2 | 4/2015 | Medich et al. |
| 9,017,680 B2 | 4/2015 | Fischkoff et al. |
| 9,018,361 B2 | 4/2015 | Hickman et al. |
| 9,061,005 B2 | 6/2015 | Hoffman et al. |
| 9,062,106 B2 | 6/2015 | Bengea et al. |
| 9,067,990 B2 | 6/2015 | Wang |
| 9,067,992 B2 | 6/2015 | Hoffman et al. |
| 9,072,668 B2 | 7/2015 | Dai et al. |
| 9,073,987 B2 | 7/2015 | Fischkoff et al. |
| 9,073,988 B2 | 7/2015 | Pla et al. |
| 9,085,618 B2 | 7/2015 | Ramasubramanyan et al. |
| 9,085,619 B2 | 7/2015 | Fraunhofer |
| 9,085,620 B1 | 7/2015 | Hoffman et al. |
| 9,086,418 B2 | 7/2015 | Maksymowych et al. |
| 9,090,688 B2 | 7/2015 | Bengea |
| 9,090,689 B1 | 7/2015 | Hoffman et al. |
| 9,090,867 B2 | 7/2015 | Pla et al. |
| 9,096,666 B2 | 8/2015 | Wan et al. |
| 9,102,723 B2 | 8/2015 | Wan et al. |
| 9,109,010 B2 | 8/2015 | Hickman et al. |
| 9,114,166 B2 | 8/2015 | Krause et al. |
| 9,150,645 B2 | 10/2015 | Subramanian et al. |
| 9,180,205 B2 | 11/2015 | Zeng et al. |
| 9,181,572 B2 | 11/2015 | Subramanian et al. |
| 9,187,559 B2 | 11/2015 | Hoffman et al. |
| 9,193,787 B2 | 11/2015 | Chumsae |
| 9,200,070 B2 | 12/2015 | Ramasubramanyan et al. |
| 9,220,781 B2 | 12/2015 | Krause et al. |
| 9,234,032 B2 | 1/2016 | Pla et al. |
| 9,272,041 B2 | 3/2016 | Krause et al. |
| 9,272,042 B2 | 3/2016 | Krause et al. |
| 9,273,132 B2 | 3/2016 | Wan et al. |
| 9,284,370 B1 | 3/2016 | Medich et al. |
| 9,289,497 B2 | 3/2016 | Krause et al. |
| 9,295,725 B2 | 3/2016 | Krause et al. |
| 9,302,011 B2 | 4/2016 | Krause et al. |
| 9,320,797 B2 | 4/2016 | Sloey |
| 9,327,032 B2 | 5/2016 | Krause et al. |
| 9,328,165 B2 | 5/2016 | Wan et al. |
| 9,334,319 B2 | 5/2016 | Ramasubramanyan et al. |
| 9,334,320 B2 | 5/2016 | Okun et al. |
| 9,340,611 B2 | 5/2016 | Manning et al. |
| 9,340,612 B2 | 5/2016 | Manning et al. |
| 9,346,880 B2 | 5/2016 | Manning et al. |
| 9,359,434 B2 | 6/2016 | Subramanian et al. |
| 9,365,645 B1 | 6/2016 | Bengea et al. |
| 9,382,317 B2 | 7/2016 | Manning et al. |
| 9,393,304 B2 | 7/2016 | Fernandez et al. |
| 9,452,138 B2 | 9/2016 | Trollsas et al. |
| 9,669,093 B2 | 6/2017 | Medich et al. |
| 2008/0118496 A1 | 5/2008 | Medich et al. |
| 2008/0166348 A1 | 7/2008 | Kupper et al. |
| 2009/0028794 A1 | 1/2009 | Medich et al. |
| 2009/0123378 A1 | 5/2009 | Wong et al. |
| 2009/0226530 A1 | 9/2009 | Lassner et al. |
| 2010/0021451 A1 | 1/2010 | Wong |
| 2010/0111853 A1 | 5/2010 | Hickman et al. |
| 2010/0278822 A1 | 11/2010 | Fraunhofer et al. |
| 2011/0059079 A1 | 3/2011 | Babuka et al. |
| 2011/0076273 A1 | 3/2011 | Adler et al. |
| 2011/0171227 A1 | 7/2011 | Okun et al. |
| 2011/0312000 A1 | 12/2011 | Kobayashi et al. |
| 2012/0122076 A1 | 5/2012 | Lau et al. |
| 2013/0079272 A1 | 3/2013 | Hui et al. |
| 2013/0115224 A1 | 5/2013 | Salfeld et al. |
| 2013/0122018 A1 | 5/2013 | Salfeld et al. |
| 2013/0243764 A1 | 9/2013 | Ellis et al. |
| 2013/0330356 A1 | 12/2013 | Salfeld et al. |
| 2013/0338344 A1 | 12/2013 | Ramasubramanyan et al. |
| 2014/0141007 A1 | 5/2014 | Fraunhofer et al. |
| 2014/0141008 A1 | 5/2014 | Fraunhofer et al. |
| 2014/0170152 A1 | 6/2014 | Hsieh et al. |
| 2014/0186368 A1 | 7/2014 | Fischkoff et al. |
| 2014/0186446 A1 | 7/2014 | Trollsas et al. |
| 2014/0200332 A1 | 7/2014 | Kaymakcalan et al. |
| 2014/0248215 A1 | 9/2014 | Hoffman et al. |
| 2014/0271633 A1 | 9/2014 | Hossler |
| 2014/0275486 A1 | 9/2014 | Chumsae |
| 2014/0314745 A1 | 10/2014 | Rives et al. |
| 2014/0329279 A1 | 11/2014 | Wang et al. |
| 2014/0288278 A1 | 12/2014 | Nti-Gyabaah et al. |
| 2014/0377275 A1 | 12/2014 | Neu et al. |
| 2015/0065696 A1 | 3/2015 | Wang et al. |
| 2015/0210735 A1 | 7/2015 | Hickman et al. |
| 2015/0246968 A1 | 9/2015 | Fischkoff et al. |
| 2015/0344564 A1 | 12/2015 | Hickman et al. |
| 2015/0361170 A1 | 12/2015 | Fraunhofer et al. |
| 2016/0017030 A1 | 1/2016 | Neu et al. |
| 2016/0046708 A1 | 2/2016 | Subramanian et al. |
| 2016/0083452 A1 | 3/2016 | Hickman et al. |
| 2016/0089495 A1 | 3/2016 | Julian et al. |
| 2016/0185849 A1 | 6/2016 | Hoffman et al. |
| 2016/0186130 A1 | 6/2016 | Pla et al. |
| 2016/0207992 A1 | 7/2016 | Bengea et al. |
| 2018/0009876 A1 | 1/2018 | Yonan et al. |
| 2019/0030163 A1 | 1/2019 | Gutka et al. |
| 2019/0048070 A1 | 2/2019 | Santoro et al. |

FOREIGN PATENT DOCUMENTS

| | | |
|---|---|---|
| EP | 0929578 B1 | 5/2003 |
| EP | 2081025 A1 | 7/2009 |
| EP | 2295071 A1 | 3/2011 |
| EP | 2324851 A1 | 5/2011 |
| EP | 2332565 A1 | 6/2011 |
| EP | 2335731 A2 | 6/2011 |
| EP | 2335732 A2 | 6/2011 |
| EP | 2338516 A2 | 6/2011 |
| EP | 1578439 B1 | 7/2011 |
| EP | 2359855 A2 | 8/2011 |
| EP | 2359856 A1 | 8/2011 |
| EP | 2361637 A1 | 8/2011 |
| EP | 2363144 A1 | 9/2011 |
| EP | 2363145 A1 | 9/2011 |
| EP | 2364731 A2 | 9/2011 |
| EP | 2371859 A2 | 10/2011 |
| EP | 1528933 B1 | 5/2012 |
| EP | 2500037 A2 | 9/2012 |
| EP | 2500413 A1 | 9/2012 |
| EP | 2500414 A1 | 9/2012 |
| EP | 2500415 A1 | 9/2012 |
| EP | 2500416 A1 | 9/2012 |
| EP | 2527425 A1 | 11/2012 |
| EP | 2532737 A1 | 12/2012 |
| EP | 1406656 B1 | 1/2013 |
| EP | 2660328 A1 | 11/2013 |
| EP | 2666472 A2 | 11/2013 |
| EP | 2666478 A2 | 11/2013 |
| EP | 2666479 A2 | 11/2013 |
| EP | 2666480 A2 | 11/2013 |

(56) References Cited

FOREIGN PATENT DOCUMENTS

| | | | |
|---|---|---|---|
| EP | 2703010 A2 | 3/2014 | |
| EP | 2708242 A2 | 3/2014 | |
| EP | 2738178 A1 | 6/2014 | |
| EP | 2738179 A1 | 6/2014 | |
| EP | 1924287 B1 | 1/2015 | |
| EP | 2946765 A1 | 11/2015 | |
| EP | 2990485 A1 | 3/2016 | |
| EP | 2397494 B1 | 8/2016 | |
| EP | 2637690 B1 | 9/2016 | |
| EP | 1737491 B1 | 11/2016 | |
| EP | 2357200 B1 | 11/2016 | |
| EP | 2359856 B1 | 5/2017 | |
| WO | WO 92/13876 A1 | 8/1992 | |
| WO | WO 2006/096461 A2 | 9/2006 | |
| WO | WO 2006/125229 A2 | 11/2006 | |
| WO | WO 2007/050498 A2 | 5/2007 | |
| WO | WO 2008/033517 A2 | 3/2008 | |
| WO | WO 2008/154543 A2 | 12/2008 | |
| WO | WO 2009/073569 A2 | 6/2009 | |
| WO | WO-2009073805 A2 * | 6/2009 | ........... C07K 16/241 |
| WO | WO 2009/118662 A2 | 10/2009 | |
| WO | WO 2010/062896 A1 | 6/2010 | |
| WO | WO 2010/129469 A1 | 11/2010 | |
| WO | WO 2010/141855 A1 | 12/2010 | |
| WO | WO 2011/104381 A2 | 9/2011 | |
| WO | WO 2012/041768 A1 | 4/2012 | |
| WO | WO 2012/051147 A1 | 4/2012 | |
| WO | WO 2013/011076 A | 1/2013 | |
| WO | WO 2013/114164 A1 | 8/2013 | |
| WO | WO 2013/114165 A1 | 8/2013 | |
| WO | WO 2013/158279 A1 | 10/2013 | |
| WO | WO 2013/186230 A1 | 12/2013 | |
| WO | WO 2014/039903 A2 | 3/2014 | |
| WO | WO 2014/055370 A1 | 4/2014 | |
| WO | WO-2014/099636 A1 | 6/2014 | |
| WO | WO 2014/143185 A1 | 9/2014 | |
| WO | WO 2014/158231 A1 | 10/2014 | |
| WO | WO 2014/207763 A1 | 12/2014 | |
| WO | WO 2015/051310 A2 | 4/2015 | |
| WO | WO-2015/057910 A1 | 4/2015 | |
| WO | WO 2015/140700 A1 | 9/2015 | |
| WO | WO 2016/066688 A1 | 5/2016 | |
| WO | WO-2016/118707 A1 | 7/2016 | |
| WO | WO 2016/120413 A1 | 8/2016 | |
| WO | WO 2017/120347 A1 | 7/2017 | |
| WO | WO 2017/120359 A1 | 7/2017 | |
| WO | WO 2017/136433 A1 | 8/2017 | |
| WO | WO 2017/136753 A1 | 8/2017 | |

OTHER PUBLICATIONS

Cleland, J.L. et al. (Mar. 2001) "A specific molar ratio of stabilizer to protein is required for storage stability of a lyophilized monoclonal antibody" *J Pharma Sci*, 90(3):310-321.

Cole, L. (Apr. 2012) "Screening optimal buffer conditions for a therapeutic antibody using Chirascan™-plus Automated Circular Dichroism" *Appl Photophysics*, p. 1-8 [online]. Retrieved from the Internet: http://www.photophysics.com/sites/default/files/documents/application_notes/4210Q244_AppNote_ACD.pdf. Retrieved on Jun. 30, 2015.

Costa, A.R. et al. (2013) "The impact of microcarrier culture optimization on the glycosylation profile of a monoclonal antibody" *SpringerPlus*, 2:25, 10 pages.

Fransson, J. et al. (Nov. 1996) "Local Tolerance of Subcutaneous Injections" *J Pharm Pharmacol*, 48:1012-1015.

Hossler, P. et al. (2015) "Cell Culture Media Supplementation of Bioflavonoids for the Targeted Reduction of Acidic Species Charge Variants on Recombinant Therapeutic Proteins" *Biotechnol Prog*, 31:1039-1052.

Imai-Nishiya, H. et al. (2007) "Double knockdown of α1,6-fucosyltransferase (FUT8) and GDP-mannose 4,6-dehydratase (GMD) in antibody-producing cells: a new strategy for generating fully non-fucosylated therapeutic antibodies with enhanced ADCC" *BMC Biotechnology*, 7:84, 13 pages.

Kaiser, C. et al. (Sep. 2011) "Injection-site reactions upon Kineret (anakinra) administration: experiences and explanations" *Rheumatol International: Clinical and Experimental Investigations*, 32(2):295-299.

Kanda, Y. et al. (2007) "Establishment of a GDP-mannose 4,6-dehydratase (GMD) knockout host cell line: A new strategy for generating completely non-fucosylated recombinant therapeutics" *J Biotechnol*, 130:300-310.

Kawasaki, Nana and Akiko Ishii (Sep. 2012) "Kotai-iyakuhin no Baio-Kouzokuhin no Syorai Tenbou (Japanese) (Future outlook for biosimilars of antibody preparations)" *Rinsho to Biseibutsu (Clinical and Microorganisms)*, vol. 39, No. 5, p. 459-465.

Lapadula, G. et al. (Jan. 2014) "Adalimumab in the Treatment of Immune-Mediated Diseases" *Intl J Immunopathol Pharmacol*, 27(1):33-48.

Matsuda, Rieko (1996) "Acids and Bases-Bronsted Setsu wo chushin ni (Japanese) (Focusing on the Bases-Bronsted theory)" *Kagaku to Kyouiku (Chemistry & Education)*. The Chemical Society of Japan, vol. 44, No. 1, p. 44-47.

Mori, K. et al. (2007) "Non-fucosylated therapeutic antibodies: the next generation of therapeutic antifodies" *Cytotechnology*, 55:109-114.

Notice of Reasons for Rejection dated Jun. 5, 2018, in Japanese Patent Application No. 2016-549199, filed Oct. 16, 2014 by Oncobiologics, Inc.; 6 pages.

Rillahan, C.D. et al. (2012) "Global metabolic inhibitors of sialyl- and fucosyltransferases remodel the glycome" *Nat Chem Biol*, 8:661-668.

Rouiller, Y. et al. (2014) "Modulation of mAb Quality Attributes Using Microliter Scale Fed-Battch Cultures" *Biotechnol Prog*, 30:571-583.

Satoh, M. et al. (2006) "Non-fucosylated therapeutic antibodies as next-generation therapeutic antibodies" *Expert Opin Biol Ther*, 6(11):1161-1173.

Serrato, J.A. et al. (2007) "Differences in the glycosylation profile of a monoclonal antibody produced by hybridomas cultured in serum-supplemented, serum-free or chemically defined media" *Biotechnol Appl Biochem*, 47:113-124.

Schmelzer, A.E. and W.M. Miller (2002) "Hyperosmotic Stress and Elevated $pCO_2$ Alter Monoclonal Antibody Charge Distribution and Monosaccharide Content" *Biotechnol Prog*, 18:346-353.

Tummala, S. et al. (2013) "Evaluation of Exogenous siRNA Addition as a Metabolic Engineering Tool for Modifying Biopharmaceuticals" *Biotechnol Prog*, 29(2):415-424. NIH Public Access Author Manuscript; available in PMC Nov. 10, 2014, 19 pages.

Von Horsten, H.H. et al. (2010) "Production of non-fucosylated antibodies by co-expression of heterologous GDP-6-deoxy-D-lyxo-4-hexulose reductase" *Glycobiology*, 20(12):1607-1618.

Wang, W. (Aug. 1999) "Instability, stabilization, and formulation of liquid protein pharmaceuticals" *Intl J Pharma*, 185(2):129-188.

Wang, W. et al. (2007) "Antibody Structure, Instability and Formulation" *J Pharma Sci*, 96(1):1-26.

Xie, P. et al. (2016) "Elucidating the effects of pH shift on IgG1 monoglonal antibody acidic charge variant levels in Chinese hamster ovary cell cultures" *Appl Microbiol Biotechnol*, 100:10343-10353.

Yamane-Ohnuki, N. and M. Satoh (2009) "Production of therapeutic antibodies with controlled fucosylation" *mAbs*, 1(3):230-236.

Zhang, X. et al. (2015) "Culture temperature modulates monoclonal antibody charge variation distribution in Chinese hamster ovary cell cultures" *Biotechnol Lett*, 37:2151-2157.

Zhou, Q. et al. (Feb. 15, 2008) "Development of a simple and rapid method for producing non-fucosylated oligomannose containing antibodies with increased effector function" *Biotechnol Bioeng*, 99(3):652-665.

Du, Y. et al. (2012) "Chromatographic analysis of the acidic and basic species of recombinant monoclonal antibodies" mAbs, 4(5):578-585.

\* cited by examiner

US 10,376,582 B2

BUFFER FORMULATIONS FOR ENHANCED ANTIBODY STABILITY

CROSS REFERENCE TO RELATED APPLICATIONS

This application is a National Stage Application, filed under 35 U.S.C. § 371, of International Application No. PCT/US2014/060810, filed on Oct. 16, 2014, which claims priority to, and the benefit of, U.S. Provisional Application No. 61/891,485 filed on Oct. 16, 2013. The contents of each of these applications are incorporated herein in their entireties.

REFERENCE TO A SEQUENCE LISTING

This application includes a Sequence Listing submitted electronically as a text file named Buffered Adalimumab ST25.txt, created on Oct. 10, 2014, with a size of 16,000 bytes. The Sequence Listing is incorporated by reference herein.

FIELD OF THE INVENTION

The invention relates generally to the field of antibody formulation chemistry. More particularly, the invention relates to buffered formulations for antibody storage, which enhance the thermal stability, conformational and colloidal stability of the antibody, thereby enhancing long term storage of the antibody.

BACKGROUND OF THE INVENTION

Various publications, including patents, published applications, accession numbers, technical articles and scholarly articles are cited throughout the specification. Each of these cited publications is incorporated by reference herein, in its entirety and for all purposes.

As part of the Biologics Price Competition and Innovation Act (BPCIA), a biological drug product (produced in or derived from living organisms) may be demonstrated to be "biosimilar" if data show that, among other things, the product is "highly similar" to an already-approved biological product. The biosimilar product should retain at least the biologic function and treatment efficacy of the U.S. Food and Drug Agency-approved biological product. The biosimilar product may be formulated differently, however, from the approved biological product. The formulation may improve stability and shelf storage of the biologic drug product, and may also improve the efficacy in treating a particular disease or condition. The formulation may also improve other aspects of administration, including a reduction in patient discomfort or other untoward effects that a patient may experience upon administration of the approved biological product.

Antibody molecules may be used as biological drugs, and many such antibodies are approved for use in human beings. Antibody molecules may be produced as a biosimilar, and reformulated accordingly. There remains a need in the art for high-quality antibody biosimilars.

SUMMARY OF THE INVENTION

The invention features buffered antibody formulations, comprising (a) an antibody. The antibody may specifically bind to tumor necrosis factor alpha. The antibody may comprise a heavy chain comprising the amino acid sequence of SEQ ID NO: 1 and a light chain comprising the amino acid sequence of SEQ ID NO: 2. The formulation, in addition to the antibody, comprises (b) an aqueous buffer comprising from about 0.7 mM to about 1.3 mM of an acetate salt, preferably sodium acetate trihydrate, from about 200 mM to about 206 mM of mannitol, from about 16 mM to about 22 mM of glacial acetic acid, and from about 24 mM to about 28 mM of sodium chloride, and (c) about 0.07% (v/v) to about 0.15% (v/v) of a non-ionic surfactant such as polysorbate 80. The buffered antibody formulation has a pH of from about 5.1 to about 5.3, preferably about 5.2.

In some aspects, the formulation comprises from about 30 mg to about 50 mg of the antibody. In some preferred aspects, the formulation comprises from about 35 mg to about 45 mg of the antibody. In some preferred aspects, the formulation comprises from about 37 mg to about 43 mg of the antibody. In some preferred aspects, the formulation comprises about 40 mg of the antibody.

The buffer may comprise from about 0.8 mM to about 1.2 mM of sodium acetate trihydrate, or from about 0.9 mM to about 1.1 mM of sodium acetate trihydrate, or about 1 mM of sodium acetate trihydrate. The buffer may comprise from about 201 mM to about 205 mM of mannitol, or from about 202 mM to about 204 mM of mannitol, or about 203 mM of mannitol. The buffer may comprise from about 17 mM to about 21 mM of glacial acetic acid, or from about 18 mM to about 20 mM of glacial acetic acid, or about 19 mM of glacial acetic acid. The buffer may comprise from about 25 mM to about 27 mM of sodium chloride, or about 26 mM of sodium chloride, or about 27 mM of sodium chloride, or about 26.35 mM of sodium chloride.

The buffered antibody formulation includes a non-ionic surfactant, which preferably is polysorbate 80. In some aspects, the formulation comprises from about 0.08% (v/v) to about 0.12% (v/v) of polysorbate 80. In some aspects, the formulation comprises from about 0.09% (v/v) to about 0.11% (v/v) of polysorbate 80. In some aspects, the formulation comprises about 0.1% (v/v) of polysorbate 80.

In a detailed aspect, a buffered antibody formulation comprises (a) about 30 mg to about 50 mg of an antibody comprising a heavy chain comprising the amino acid sequence of SEQ ID NO: 1 and a light chain comprising the amino acid sequence of SEQ ID NO: 2, (b) a buffer comprising about 1 mM of an acetate salt, preferably sodium acetate trihydrate, about 203 mM of mannitol, about 19 mM of glacial acetic acid, and about 26.35 mM of sodium chloride, and (c) about 0.1% (by volume) of polysorbate 80. The buffered antibody formulation has a pH of from about 5.1 to about 5.3, preferably about 5.2. In some preferred aspects, the formulation comprises from about 35 mg to about 45 mg of the antibody. In some preferred aspects, the formulation comprises from about 37 mg to about 43 mg of the antibody. In some preferred aspects, the formulation comprises about 40 mg of the antibody.

The buffered antibody formulations may be used as a medicament, and may be used in methods of treatment. For example, the buffered antibody formulations may be for use in the treatment of arthritis. In some aspects, the buffered antibody formulations may be for use in the treatment of Rheumatoid Arthritis, or Juvenile Idiopathic Arthritis, or Psoriatic Arthritis. In some aspects, the buffered antibody formulations may be for use in the treatment of Ankylosing Spondylitis. In some aspects, the buffered antibody formulations may be for use in the treatment of Crohn's Disease. In some aspects, the buffered antibody formulations may be for use in the treatment of Ulcerative Colitis. In some aspects, the buffered antibody formulations may be for use in the treatment of Plaque Psoriasis.

The methods of treatment include methods for treating arthritis, including Rheumatoid Arthritis, Juvenile Idiopathic Arthritis, and Psoriatic Arthritis. The methods of treatment also include methods for treating Ankylosing Spondylitis, methods for treating Crohn's Disease, methods for treating Plaque Psoriasis, and methods for treating Ulcerative Colitis.

In some aspects, methods of treatment comprise administering to an arthritis patient, including a Rheumatoid Arthritis, Juvenile Idiopathic Arthritis, or Psoriatic Arthritis, an amount of the buffered antibody formulations described or exemplified herein effective to treat the arthritis in the patient. In some aspects, methods of treatment comprise administering to an Ankylosing Spondylitis patient an amount of the buffered antibody formulations described or exemplified herein effective to treat the Ankylosing Spondylitis in the patient. In some aspects, methods of treatment comprise administering to a Crohn's Disease patient an amount of the buffered antibody formulations described or exemplified herein effective to treat the Crohn's Disease in the patient. In some aspects, methods of treatment comprise administering to an Ulcerative Colitis patient an amount of the buffered antibody formulations described or exemplified herein effective to treat the Ulcerative Colitis in the patient. In some aspects, methods of treatment comprise administering to a Plaque Psoriasis patient an amount of the buffered antibody formulations described or exemplified herein effective to treat the Plaque Psoriasis in the patient. The buffered antibody formulations are preferably administered subcutaneously to the patient, for example, by subcutaneous injection. The patient preferably is a human being.

The invention also provides kits, which may be used, for example, in accordance with the methods of treatment. Thus, for example, the kits generally comprise any of the buffered antibody formulations described or exemplified herein and instructions for using the formulation in a method of treatment. The method of treatment may be a method for treating arthritis. The method of treatment may be a method for treating Rheumatoid Arthritis. The method of treatment may be a method for treating Juvenile Idiopathic Arthritis. The method of treatment may be a method for treating Psoriatic Arthritis. The method of treatment may be a method for treating Ankylosing Spondylitis. The method of treatment may be a method for treating Crohn's Disease. The method of treatment may be a method for treating Ulcerative Colitis. The method of treatment may be a method for treating Plaque Psoriasis. The kits may include a device for administering the antibody formulation to a patient. The device may comprise a syringe and a needle. The device may comprise a catheter.

DETAILED DESCRIPTION OF THE INVENTION

Figure 1:
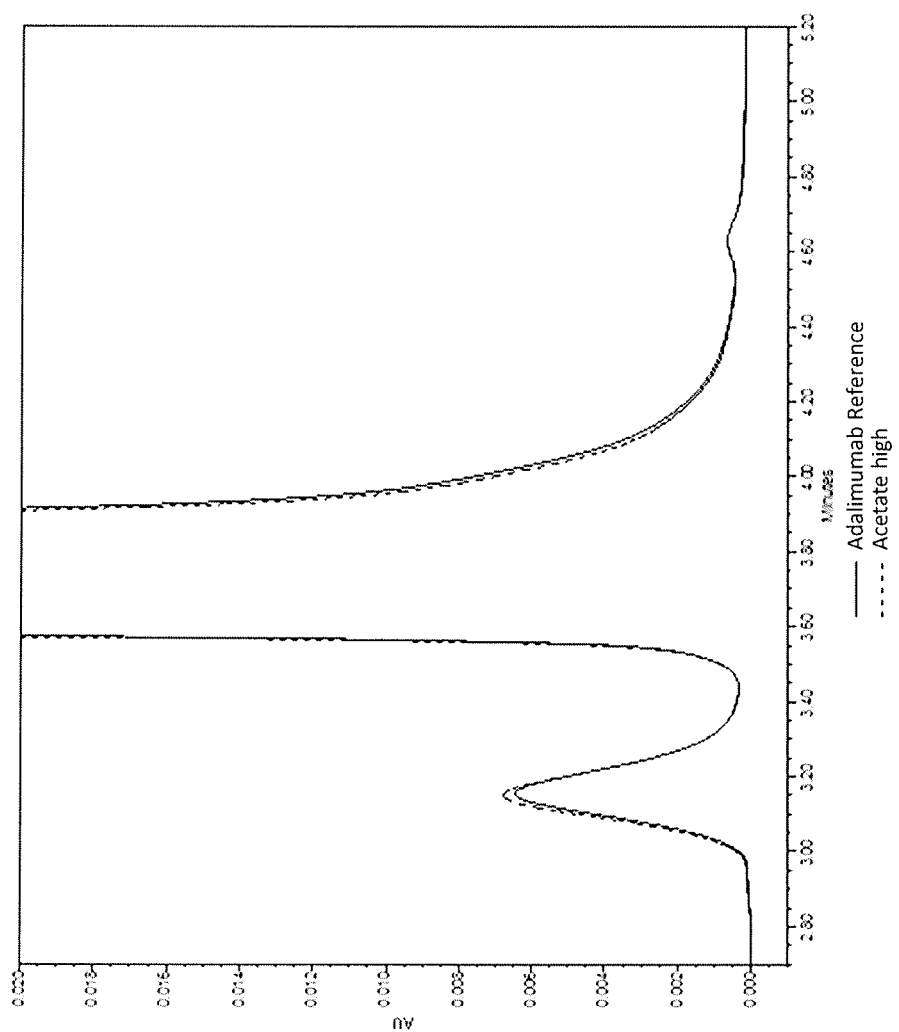
FIG. 1 shows an overlay of SE-UPLC chromatograms from representative experimental series 1 formulation conditions.

Various terms relating to aspects of the present invention are used throughout the specification and claims. Such terms are to be given their ordinary meaning in the art, unless otherwise indicated. Other specifically defined terms are to be construed in a manner consistent with the definition provided herein.

As used herein, the singular forms "a," "an," and "the" include plural referents unless expressly stated otherwise.

As used herein, the terms "comprising," "having," and "including" encompass the more restrictive terms "consisting essentially of" and "consisting of."

The terms subject and patient are used interchangeably, and include any animal. Subjects include mammals, including companion and farm mammals, as well as rodents, including mice, rabbits, and rats, and other rodents. Non-human primates preferred subjects. Human beings are highly preferred subjects.

It has been observed in accordance with the invention that formulations of ONS-3010, which specifically binds to tumor necrosis factor alpha, can be buffered with mannitol and acetate, while minimizing sodium chloride, with the buffers enhancing the thermal and colloidal stability of the antibody, even more so than formulations of adalimumab currently approved for patient use. It was observed that there is a fine balance in establishing and maintaining an acidic pH of about 5.2 with the appropriate salts and buffer components. It was observed, for example, that high levels of salt may induce aggregation and degradation, which could be improved by lowering the salt level. Accordingly, the disclosure features buffered formulations for antibodies, which formulations include an aqueous carrier comprising buffer comprising acetate and mannitol, as well as a non-ionic surfactant, but with minimal sodium chloride.

In some preferred aspects, the antibody specifically binds to an epitope on tumor necrosis factor alpha, and the epitope may be linear or conformational. In some preferred aspects, the antibody comprises a heavy chain comprising the amino acid sequence of SEQ ID NO: 1. In some preferred aspects, the antibody comprises a light chain comprising the amino acid sequence of SEQ ID NO: 2. Preferably, the antibody comprises a heavy chain constant domain and/or a light chain constant domain. In highly preferred aspects, the antibody comprises a heavy chain comprising the amino acid sequence of SEQ ID NO: 1 and a light chain comprising the amino acid sequence of SEQ ID NO: 2, an example of which is ONS-3010. The heavy and light chain amino acid sequences of the antibody may comprise those of U.S. Pat. No. 6,090,382.

Preferably, the antibody is a full length antibody, comprising both variable and constant regions, although in some aspects, the antibody may comprise a derivative or fragment or portion of a full-length antibody that retains the antigen-binding specificity, and also preferably retains most or all of the affinity, of the full length antibody molecule. The antibody may comprise post-translational modifications (PTMs) or moieties, which may impact antibody activity or stability. The antibody may be methylated, acetylated, glycosylated, sulfated, phosphorylated, carboxylated, and/or amidated, and may comprise other moieties that are well known in the art. Common PTMs for ONS-3010 include N-glycosylation, C-terminal variants (e.g., cleavage of lysine, proline amidation), N-terminal pyro-E formation, oxidation, isomerization, deamidation, succinimide formation, mannosylation, K98 glycation, and fragmentation. Moieties include any chemical group or combinations of groups commonly found on immunoglobulin molecules in nature, or otherwise added to antibodies by recombinant expression systems, including prokaryotic and eukaryotic expression systems.

The formulation preferably comprises a therapeutically effective amount of an antibody. The antibody may be any antibody compatible with the aqueous buffer formulation. A preferred antibody comprises a heavy chain having the amino acid sequence of SEQ ID NO: 1 and a light chain having the amino acid sequence of SEQ ID NO: 2. A therapeutically effective amount may vary, depending on the disease or condition being treated upon administration of the antibody, and/or depending on the characteristics of the subject to which the antibody is administered, such as age, gender, height, weight, state of advancement or stage of the disease or condition, the number and efficacy of previous administrations, other therapeutic agents administered to the subject, and other characteristics that are known to the practitioner or that would otherwise be taken into account in determining appropriate dosing. Preferably, a therapeutically effective amount is an amount that is effective to treat Rheumatoid Arthritis. In some preferred aspects, a therapeutically effective amount is an amount that is effective to treat Juvenile Idiopathic Arthritis, Psoriatic Arthritis, Ankylosing Spondylitis, Crohn's Disease, Plaque Psoriasis, Ulcerative Colitis, Inflammatory Bowel Disease, Hidradenitis Suppurativa, or Refractory Asthma.

The formulation may comprise from about 10 mg to about 70 mg of the antibody. In some aspects, the formulation comprises from about 20 mg to about 60 mg of the antibody. In some aspects, the formulation comprises from about 30 mg to about 50 mg of the antibody. In some aspects, the formulation comprises from about 35 mg to about 45 mg of the antibody. In some aspects, the formulation comprises from about 37 mg to about 43 mg of the antibody. In some aspects, the formulation comprises from about 38 mg to about 42 mg of the antibody. In some aspects, the formulation comprises from about 39 mg to about 41 mg of the antibody. In some aspects, the formulation comprises from about 30 mg to about 60 mg of the antibody. In some aspects, the formulation comprises from about 35 mg to about 55 mg of the antibody. In some aspects, the formulation comprises from about 40 mg to about 60 mg of the antibody. These ranges include the lower and upper amounts that define the range. In some aspects, the formulation comprises about 40 mg of the antibody.

The antibody is preferably formulated with a buffered aqueous carrier, and the carrier preferably comprises water. The buffered antibody formulation is preferably in liquid form, and more preferably in liquid form suitable for subcutaneous administration. Thus, the amount of water in the buffered formulation may vary in accordance with the desired volume of the injectable bolus. The buffer comprises sodium acetate trihydrate, mannitol, sodium chloride, glacial acetic acid, and a non-ionic surfactant, and maintains the antibody formulation at an acidic pH. When stored in the buffered formulation, the antibody is shelf-stable under normal storage conditions.

The buffer may comprise from about 0.1 mM to about 5 mM of an acetate salt. In some aspects, the buffer may comprise from about 0.3 mM to about 3 mM of an acetate salt. In some aspects, the buffer may comprise from about 0.5 mM to about 2 mM of an acetate salt. In some aspects, the buffer may comprise from about 0.5 mM to about 1.5 mM of an acetate salt. In some aspects, the buffer may comprise from about 0.6 mM to about 1.4 mM of an acetate salt. In some aspects, the buffer may comprise from about 0.7 mM to about 1.5 mM of an acetate salt. In some aspects, the buffer may comprise from about 0.7 mM to about 1.3 mM of an acetate salt. In some aspects, the buffer may comprise from about 0.8 mM to about 1.2 mM of an acetate salt. In some aspects, the buffer may comprise from about 0.8 mM to about 1.5 mM of an acetate salt. In some aspects, the buffer may comprise from about 0.8 mM to about 1.1 mM of an acetate salt. In some aspects, the buffer may comprise from about 0.9 mM to about 1.2 mM of an acetate salt. In some aspects, the buffer may comprise from about 0.9 mM to about 1.4 mM of an acetate salt. In some aspects, the buffer may comprise from about 0.9 mM to about 1.1 mM of an acetate salt. These ranges include the lower and upper amounts that define the range. In some aspects, the buffer comprises about 1 mM of an acetate salt. The acetate salt may comprise any suitable acetate salt. Non-limiting examples of preferred acetate salts include magnesium acetate salts, potassium acetate salts, calcium acetate salts, zinc acetate salts, and sodium acetate salts. More preferred acetate salts include anhydrous sodium acetate and sodium acetate trihydrate. Sodium acetate trihydrate is highly preferred.

The buffer may comprise from about 100 mM to about 300 mM of mannitol. In some aspects, the buffer may comprise from about 110 mM to about 290 mM of mannitol. In some aspects, the buffer may comprise from about 120 mM to about 280 mM of mannitol. In some aspects, the buffer may comprise from about 150 mM to about 250 mM of mannitol. In some aspects, the buffer may comprise from about 175 mM to about 225 mM of mannitol. In some aspects, the buffer may comprise from about 180 mM to about 220 mM of mannitol. In some aspects, the buffer may comprise from about 185 mM to about 215 mM of mannitol. In some aspects, the buffer may comprise from about 190 mM to about 215 mM of mannitol. In some aspects, the buffer may comprise from about 195 mM to about 210 mM of mannitol. In some aspects, the buffer may comprise from about 197 mM to about 209 mM of mannitol. In some aspects, the buffer may comprise from about 198 mM to about 208 mM of mannitol. In some aspects, the buffer may comprise from about 198 mM to about 205 mM of mannitol. In some aspects, the buffer may comprise from about 199 mM to about 207 mM of mannitol. In some aspects, the buffer may comprise from about 200 mM to about 210 mM of mannitol. In some aspects, the buffer may comprise from about 200 mM to about 207 mM of mannitol. In some aspects, the buffer may comprise from about 200 mM to about 206 mM of mannitol. In some aspects, the buffer may comprise from about 200 mM to about 205 mM of mannitol. In some aspects, the buffer may comprise from about 200 mM to about 203 mM of mannitol. In some aspects, the buffer may comprise from about 201 mM to about 205 mM of mannitol. In some aspects, the buffer may comprise from about 201 mM to about 204 mM of mannitol. In some aspects, the buffer may comprise from about 201 mM to about 203 mM of mannitol. In some aspects, the buffer may comprise from about 202 mM to about 204 mM of mannitol. In some aspects, the buffer may comprise from about 202 mM to about 203 mM of mannitol. In some aspects, the buffer may comprise from about 202 mM to about 206 mM of mannitol. These ranges include the lower and upper amounts that define the range. In some aspects, the buffer comprises about 203 mM of mannitol.

The buffer may comprise from about 9 mM to about 30 mM of glacial acetic acid. In some aspects, the buffer may comprise from about 10 mM to about 30 mM of glacial acetic acid. In some aspects, the buffer may comprise from about 9 mM to about 29 mM of glacial acetic acid. In some aspects, the buffer may comprise from about 10 mM to about 28 mM of glacial acetic acid. In some aspects, the buffer may comprise from about 11 mM to about 27 mM of glacial acetic acid. In some aspects, the buffer may comprise from about 12 mM to about 26 mM of glacial acetic acid. In some aspects, the buffer may comprise from about 13 mM to about 25 mM of glacial acetic acid. In some aspects, the buffer may comprise from about 14 mM to about 24 mM of glacial acetic acid. In some aspects, the buffer may comprise from about 15 mM to about 23 mM of glacial acetic acid. In some aspects, the buffer may comprise from about 15 mM to about 21 mM of glacial acetic acid. In some aspects, the buffer may comprise from about 15 mM to about 20 mM of glacial acetic acid. In some aspects, the buffer may comprise from about 16 mM to about 22 mM of glacial acetic acid. In some aspects, the buffer may comprise from about 16 mM to about 20 mM of glacial acetic acid. In some aspects, the buffer may comprise from about 17 mM to about 21 mM of glacial acetic acid. In some aspects, the buffer may comprise from about 17 mM to about 20 mM of glacial acetic acid. In some aspects, the buffer may comprise from about 18 mM to about 20 mM of glacial acetic acid. In some aspects, the buffer may comprise from about 18 mM to about 19 mM of glacial acetic acid. In some aspects, the buffer may comprise from about 18 mM to about 23 mM of glacial acetic acid. In some aspects, the buffer may comprise from about 19 mM to about 20 mM of glacial acetic acid. These ranges include the lower and upper amounts that define the range. In some aspects, the buffer comprises about 19 mM of glacial acetic acid.

The buffer preferably includes minimal amounts of sodium chloride, and in some aspects, includes no sodium chloride. In some aspects, the buffer may comprise from about 15 mM to about 36 mM of sodium chloride. In some aspects, the buffer may comprise from about 16 mM to about 36 mM of sodium chloride. In some aspects, the buffer may comprise from about 18 mM to about 34 mM of sodium chloride. In some aspects, the buffer may comprise from about 20 mM to about 32 mM of sodium chloride. In some aspects, the buffer may comprise from about 22 mM to about 30 mM of sodium chloride. In some aspects, the buffer may comprise from about 23 mM to about 29 mM of sodium chloride. In some aspects, the buffer may comprise from about 23 mM to about 27 mM of sodium chloride. In some aspects, the buffer may comprise from about 24 mM to about 28 mM of sodium chloride. In some aspects, the buffer may comprise from about 24 mM to about 30 mM of sodium chloride. In some aspects, the buffer may comprise from about 25 mM to about 27 mM of sodium chloride. In some aspects, the buffer may comprise from about 25 mM to about 28 mM of sodium chloride. In some aspects, the buffer may comprise from about 25 mM to about 30 mM of sodium chloride. In some aspects, the buffer may comprise from about 25.5 mM to about 27.5 mM of sodium chloride. In some aspects, the buffer may comprise from about 25.3 mM to about 27.3 mM of sodium chloride. In some aspects, the buffer may comprise from about 25.4 mM to about 27.4 mM of sodium chloride. In some aspects, the buffer may comprise from about 25.35 mM to about 27.35 mM of sodium chloride. In some aspects, the buffer may comprise from about 26 mM to about 30 mM of sodium chloride. In some aspects, the buffer may comprise from about 26 mM to about 28 mM of sodium chloride. In some aspects, the buffer may comprise from about 26 mM to about 27 mM of sodium chloride. In some aspects, the buffer may comprise from about 26.3 mM to about 27.3 mM of sodium chloride. In some aspects, the buffer may comprise from about 26.4 mM to about 27.4 mM of sodium chloride. In some aspects, the buffer may comprise from about 26.3 mM to about 26.4 mM of sodium chloride. These ranges include the lower and upper amounts that define the range. In some aspects, the buffer comprises about 26 mM of sodium chloride. In some aspects, the buffer comprises about 27 mM of sodium chloride. In some aspects, the buffer comprises about 26.3 mM of sodium chloride. In some aspects, the buffer comprises about 26.4 mM of sodium chloride. In some aspects, the buffer comprises about 26.35 mM of sodium chloride.

The antibody formulation preferably comprises a non-ionic surfactant. More preferably, the non-ionic surfactant comprises polysorbate 80. The antibody formulation, including the antibody and the aqueous buffer, preferably comprises from about 0.01% to about 1% (by volume) of polysorbate 80. In some aspects, the antibody formulation comprises from about 0.03% to about 0.7% (by volume) of polysorbate 80. In some aspects, the antibody formulation comprises from about 0.05% to about 0.4% (by volume) of polysorbate 80. In some aspects, the antibody formulation comprises from about 0.075% to about 0.3% (by volume) of polysorbate 80. In some aspects, the antibody formulation comprises from about 0.07% to about 0.25% (by volume) of polysorbate 80. In some aspects, the antibody formulation comprises from about 0.07% to about 0.2% (by volume) of polysorbate 80. In some aspects, the antibody formulation comprises from about 0.07% to about 0.15% (by volume) of polysorbate 80. In some aspects, the antibody formulation comprises from about 0.07% to about 0.14% (by volume) of polysorbate 80. In some aspects, the antibody formulation comprises from about 0.08% to about 0.3% (by volume) of polysorbate 80. In some aspects, the antibody formulation comprises from about 0.08% to about 0.2% (by volume) of polysorbate 80. In some aspects, the antibody formulation comprises from about 0.08% to about 0.15% (by volume) of polysorbate 80. In some aspects, the antibody formulation comprises from about 0.08% to about 0.12% (by volume) of polysorbate 80. In some aspects, the antibody formulation comprises from about 0.08% to about 0.1% (by volume) of polysorbate 80. In some aspects, the antibody formulation comprises from about 0.09% to about 0.15% (by volume) of polysorbate 80. In some aspects, the antibody formulation comprises from about 0.09% to about 0.2% (by volume) of polysorbate 80. In some aspects, the antibody formulation comprises from about 0.09% to about 0.18% (by volume) of polysorbate 80. In some aspects, the antibody formulation comprises from about 0.09% to about 0.11% (by volume) of polysorbate 80. In some aspects, the antibody formulation comprises from about 0.09% to about 0.1% (by volume) of polysorbate 80. These ranges include the lower and upper amounts that define the range. In some aspects, the antibody formulation comprises about 0.1% (by volume) of polysorbate 80.

The antibody formulation preferably is buffered to an acidic pH. The formulation preferably has a pH of about 4.8 to about 5.6. In some aspects, the formulation has a pH of about 4.9 to about 5.5. In some aspects, the formulation has a pH of about 5.0 to about 5.4. In some preferred aspects, the formulation has a pH of about 5.0 to about 5.3. In some preferred aspects, the formulation has a pH of about 5.0 to about 5.2. In some aspects, the formulation has a pH of about 5.1 to about 5.3. In some aspects, the formulation has a pH of about 5.1 to about 5.5. In some preferred aspects, the formulation has a pH of about 5.1 to about 5.2. In some preferred aspects, the formulation has a pH of about 5.1 to about 5.4. In some aspects, the formulation has a pH of about 5.2 to about 5.4. In some aspects, the formulation has a pH of about 5.2 to about 5.5. In some preferred aspects, the formulation has a pH of about 5.2 to about 5.3. These ranges include the lower and upper amounts that define the range. In some aspects, the formulation has a pH of about 5.2.

In some preferred aspects, the antibody formulation comprises about 35 mg to about 45 mg of an antibody that specifically binds to tumor necrosis factor alpha and comprises a heavy chain comprising the amino acid sequence of SEQ ID NO: 1 and a light chain comprising the amino acid sequence of SEQ ID NO: 2, a buffer comprising about 0.7 mM to about 1.3 mM of sodium acetate trihydrate, about 200 mM to about 206 mM of mannitol, about 16 mM to about 22 mM of glacial acetic acid, and about 24 mM to about 28 mM of sodium chloride, and about 0.07% to about 0.15% (by volume) of polysorbate 80, and has a pH of about 5.1 to about 5.3. In some aspects, the antibody formulation consists essentially of about 35 mg to about 45 mg of an antibody that specifically binds to tumor necrosis factor alpha and comprises a heavy chain comprising the amino acid sequence of SEQ ID NO: 1 and a light chain comprising the amino acid sequence of SEQ ID NO: 2, a buffer consisting essentially of about 0.7 mM to about 1.3 mM of sodium acetate trihydrate, about 200 mM to about 206 mM of mannitol, about 16 mM to about 22 mM of glacial acetic acid, and about 24 mM to about 28 mM of sodium chloride, and about 0.07% to about 0.15% (by volume) of polysorbate 80, and has a pH of about 5.1 to about 5.3. In some aspects, the antibody formulation consists of about 35 mg to about 45 mg of an antibody that specifically binds to tumor necrosis factor alpha and comprises a heavy chain comprising the amino acid sequence of SEQ ID NO: 1 and a light chain comprising the amino acid sequence of SEQ ID NO: 2, a buffer consisting of about 0.7 mM to about 1.3 mM of sodium acetate trihydrate, about 200 mM to about 206 mM of mannitol, about 16 mM to about 22 mM of glacial acetic acid, and about 24 mM to about 28 mM of sodium chloride, and about 0.07% to about 0.15% (by volume) of polysorbate 80, and has a pH of about 5.1 to about 5.3. In any such embodiments, the antibody may be present in the formulation at about 37 mg to about 43 mg, or about 38 mg to about 42 mg, or about 39 mg to about 41 mg, or about 40 mg.

In some preferred aspects, the antibody formulation comprises about 35 mg to about 45 mg of an antibody that specifically binds to tumor necrosis factor alpha and comprises a heavy chain comprising the amino acid sequence of SEQ ID NO: 1 and a light chain comprising the amino acid sequence of SEQ ID NO: 2, a buffer comprising about 0.8 mM to about 1.2 mM of an acetate salt, about 201 mM to about 205 mM of mannitol, about 17 mM to about 21 mM of glacial acetic acid, and about 25 mM to about 27 mM of sodium chloride, and about 0.08% to about 0.15% (by volume) of polysorbate 80, and has a pH of about 5.1 to about 5.3. In some aspects, the antibody formulation consists essentially of about 35 mg to about 45 mg of an antibody that specifically binds to tumor necrosis factor alpha and comprises a heavy chain comprising the amino acid sequence of SEQ ID NO: 1 and a light chain comprising the amino acid sequence of SEQ ID NO: 2, a buffer consisting essentially of about 0.8 mM to about 1.2 mM of an acetate salt, about 201 mM to about 205 mM of mannitol, about 17 mM to about 21 mM of glacial acetic acid, and about 25 mM to about 27 mM of sodium chloride, and about 0.08% to about 0.15% (by volume) of polysorbate 80, and has a pH of about 5.1 to about 5.3. In some aspects, the antibody formulation consists of about 35 mg to about 45 mg of an antibody that specifically binds to tumor necrosis factor alpha and comprises a heavy chain comprising the amino acid sequence of SEQ ID NO: 1 and a light chain comprising the amino acid sequence of SEQ ID NO: 2, a buffer consisting of about 0.8 mM to about 1.2 mM of an acetate salt, about 201 mM to about 205 mM of mannitol, about 17 mM to about 21 mM of glacial acetic acid, and about 25 mM to about 27 mM of sodium chloride, and about 0.08% to about 0.15% (by volume) of polysorbate 80, and has a pH of about 5.1 to about 5.3. In any such embodiments, the antibody may be present in the formulation at about 37 mg to about 43 mg, or about 38 mg to about 42 mg, or about 39 mg to about 41 mg, or about 40 mg. The acetate salt may comprise any suitable acetate salt. Non-limiting examples of preferred acetate salts include magnesium acetate salts, potassium acetate salts, calcium acetate salts, zinc acetate salts, and sodium acetate salts. More preferred acetate salts include anhydrous sodium acetate and sodium acetate trihydrate. Sodium acetate trihydrate is highly preferred.

In some preferred aspects, the antibody formulation comprises about 39 mg to about 41 mg of an antibody that specifically binds to tumor necrosis factor alpha and comprises a heavy chain comprising the amino acid sequence of SEQ ID NO: 1 and a light chain comprising the amino acid sequence of SEQ ID NO: 2, a buffer comprising about 0.9 mM to about 1.1 mM of an acetate salt, about 202 mM to about 204 mM of mannitol, about 18 mM to about 20 mM of glacial acetic acid, and about 25.35 mM to about 26.35 mM of sodium chloride, and about 0.09% to about 0.11% (by volume) of polysorbate 80, and has a pH of about 5.1 to about 5.3. In some aspects, the antibody formulation consists essentially of about 39 mg to about 41 mg of an antibody that specifically binds to tumor necrosis factor alpha and comprises a heavy chain comprising the amino acid sequence of SEQ ID NO: 1 and a light chain comprising the amino acid sequence of SEQ ID NO: 2, a buffer consisting essentially of about 0.9 mM to about 1.1 mM of an acetate salt, about 202 mM to about 204 mM of mannitol, about 18 mM to about 20 mM of glacial acetic acid, and about 25.35 mM to about 26.35 mM of sodium chloride, and about 0.09% to about 0.11% (by volume) of polysorbate 80, and has a pH of about 5.1 to about 5.3. In some aspects, the antibody formulation consists of about 39 mg to about 41 mg of an antibody that specifically binds to tumor necrosis factor alpha and comprises a heavy chain comprising the amino acid sequence of SEQ ID NO: 1 and a light chain comprising the amino acid sequence of SEQ ID NO: 2, a buffer consisting of about 0.9 mM to about 1.1 mM of an acetate salt, about 202 mM to about 204 mM of mannitol, about 18 mM to about 20 mM of glacial acetic acid, and about 25.35 mM to about 26.35 mM of sodium chloride, and about 0.09% to about 0.11% (by volume) of polysorbate 80, and has a pH of about 5.1 to about 5.3. In any such embodiments, the antibody may be present in the formulation at about 37 mg to about 43 mg, or about 38 mg to about 42 mg, or about 39 mg to about 41 mg, or about 40 mg. The acetate salt may comprise any suitable acetate salt. Non-limiting examples of preferred acetate salts include magnesium acetate salts, potassium acetate salts, calcium acetate salts, zinc acetate salts, and sodium acetate salts. More preferred acetate salts include anhydrous sodium acetate and sodium acetate trihydrate. Sodium acetate trihydrate is highly preferred.

In some preferred aspects, the antibody formulation comprises about 40 mg of an antibody that specifically binds to tumor necrosis factor alpha and comprises a heavy chain comprising the amino acid sequence of SEQ ID NO: 1 and a light chain comprising the amino acid sequence of SEQ ID NO: 2, a buffer comprising about 1 mM of an acetate salt, about 203 mM of mannitol, about 19 mM of glacial acetic acid, and about 26.35 mM of sodium chloride, and about 0.1% (by volume) of polysorbate 80, and has a pH of about 5.2. In some aspects, the antibody formulation consists essentially of about 40 mg of an antibody that specifically binds to tumor necrosis factor alpha and comprises a heavy chain comprising the amino acid sequence of SEQ ID NO: 1 and a light chain comprising the amino acid sequence of SEQ ID NO: 2, a buffer consisting essentially of about 1 mM of an acetate salt, about 203 mM of mannitol, about 19 mM of glacial acetic acid, and about 26.35 mM of sodium chloride, and about 0.1% (by volume) of polysorbate 80, and has a pH of about 5.2. In some aspects, the antibody formulation consists of about 40 mg of an antibody that specifically binds to tumor necrosis factor alpha and comprises a heavy chain comprising the amino acid sequence of SEQ ID NO: 1 and a light chain comprising the amino acid sequence of SEQ ID NO: 2, a buffer consisting of about 1 mM of an acetate salt, about 203 mM of mannitol, about 19 mM of glacial acetic acid, and about 26.35 mM of sodium chloride, and about 0.1% (by volume) of polysorbate 80, and has a pH of about 5.2. The acetate salt may comprise any suitable acetate salt. Non-limiting examples of preferred acetate salts include magnesium acetate salts, potassium acetate salts, calcium acetate salts, zinc acetate salts, and sodium acetate salts. More preferred acetate salts include anhydrous sodium acetate and sodium acetate trihydrate. Sodium acetate trihydrate is highly preferred.

The formulation stabilizes the antibody for improved shelf storage, particularly over a period of months to years. When stored in the formulation, the antibody maintains thermal and colloidal stability during the period of storage. For example, when stored in the formulation, the antibody is stable and exhibits minimal aggregation, flocculation, fragmentation, and denaturation, and the antibody retains it tumor necrosis factor alpha binding activity.

It is preferred that the antibody formulation be stored under refrigerated conditions, and preferably at a temperature of from about 2° C. to about 8° C., including from about 2° C. to about 6° C., and including about 2° C., about 3° C., about 4° C., about 5° C., about 6° C., about 7° C., or about 8° C. The antibody formulation may be stored at such temperatures for at least about 3 months. In some aspects, the antibody formulation may be stored at such temperatures for at least about 6 months. In some aspects, the antibody formulation may be stored at such temperatures for at least about 9 months. In some aspects, the antibody formulation may be stored at such temperatures for at least about 12 months. In some aspects, the antibody formulation may be stored at such temperatures for at least about 15 months. In some aspects, the antibody formulation may be stored at such temperatures for at least about 18 months. During the storage period the antibody is stable and exhibits minimal aggregation, flocculation, fragmentation, and denaturation, and the antibody retains it tumor necrosis factor alpha binding activity such that the antibody formulation may be removed from storage, administered to a patient, and still exhibit therapeutic efficacy against the condition for which the formulation is administered.

The formulation comprises about 10 mg to about 70 mg of antibody. Among this amount of antibody protein is a percentage of antibody monomers in active, native form, as well as a percentage of antibody fragments, antibody aggregates, and denatured or partially denatured antibodies that have reduced or no tumor necrosis binding activity. It is highly preferred that the formulation include a maximal amount of functional antibody monomers and a minimal amount of antibody fragments, aggregates, and structurally altered forms of the antibody with reduced binding activity and/or therapeutic efficacy (relative to the unaltered monomer). For example, the antibody formulation preferably contains at least about 85% by weight of antibody monomers, and less than about 15% by weight of antibody fragments, aggregates, and structurally altered forms with reduced tumor necrosis factor alpha binding activity and/or therapeutic efficacy when stored at about 2° C. to about 8° C. for at least about six months.

In some aspects, the antibody formulation contains at least about 90% by weight of antibody monomers, and less than about 10% by weight of antibody fragments, aggregates, and structurally altered forms with reduced tumor necrosis factor alpha binding activity and/or therapeutic efficacy when stored at about 2° C. to about 8° C. for at least about six months. In some aspects, the antibody formulation contains at least about 93% by weight of antibody monomers, and less than about 7% by weight of antibody fragments, aggregates, and structurally altered forms with reduced tumor necrosis factor alpha binding activity and/or therapeutic efficacy when stored at about 2° C. to about 8° C. for at least about six months. In some aspects, the antibody formulation contains at least about 95% by weight of antibody monomers, and less than about 5% by weight of antibody fragments, aggregates, and structurally altered forms with reduced tumor necrosis factor alpha binding activity and/or therapeutic efficacy when stored at about 2° C. to about 8° C. for at least about six months. In some aspects, the antibody formulation contains at least about 96% by weight of antibody monomers, and less than about 4% by weight of antibody fragments, aggregates, and structurally altered forms with reduced tumor necrosis factor alpha binding activity and/or therapeutic efficacy when stored at about 2° C. to about 8° C. for at least about six months. In some aspects, the antibody formulation contains at least about 97% by weight of antibody monomers, and less than about 3% by weight of antibody fragments, aggregates, and structurally altered forms with reduced tumor necrosis factor alpha binding activity and/or therapeutic efficacy when stored at about 2° C. to about 8° C. for at least about six months. In some aspects, the antibody formulation contains at least about 98% by weight of antibody monomers, and less than about 2% by weight of antibody fragments, aggregates, and structurally altered forms with reduced tumor necrosis factor alpha binding activity and/or therapeutic efficacy when stored at about 2° C. to about 8° C. for at least about six months. In some aspects, the antibody formulation contains at least about 99% by weight of antibody monomers, and less than about 1% by weight of antibody fragments, aggregates, and structurally altered forms with reduced tumor necrosis factor alpha binding activity and/or therapeutic efficacy when stored at about 2° C. to about 8° C. for at least about six months. The amount of antibody monomers and antibody fragments, aggregates, and structurally altered forms may be determined according to any technique suitable in the art, including those described or exemplified herein, including any one or combination of dynamic light scattering (DLS), differential scanning calorimetry (DSC), size exclusion chromatography (SE-UPLC), non-reducing and reducing capillary electrophoresis SDS (NR CE-SDS and R CE-SDS), peptide mapping and particle counting (PC).

In some aspects, the antibody formulation contains at least about 90% by weight of antibody monomers, and less than about 10% by weight of antibody fragments, aggregates, and structurally altered forms with reduced tumor necrosis factor alpha binding activity and/or therapeutic efficacy when stored at about 2° C. to about 8° C. for at least about twelve months. In some aspects, the antibody formulation contains at least about 93% by weight of antibody monomers, and less than about 7% by weight of antibody fragments, aggregates, and structurally altered forms with reduced tumor necrosis factor alpha binding activity and/or therapeutic efficacy when stored at about 2° C. to about 8° C. for at least about twelve months. In some aspects, the antibody formulation contains at least about 95% by weight of antibody monomers, and less than about 5% by weight of antibody fragments, aggregates, and structurally altered forms with reduced tumor necrosis factor alpha binding activity and/or therapeutic efficacy when stored at about 2° C. to about 8° C. for at least about twelve months. In some aspects, the antibody formulation contains at least about 96% by weight of antibody monomers, and less than about 4% by weight of antibody fragments, aggregates, and structurally altered forms with reduced tumor necrosis factor alpha binding activity and/or therapeutic efficacy when stored at about 2° C. to about 8° C. for at least about twelve months. In some aspects, the antibody formulation contains at least about 97% by weight of antibody monomers, and less than about 3% by weight of antibody fragments, aggregates, and structurally altered forms with reduced tumor necrosis factor alpha binding activity and/or therapeutic efficacy when stored at about 2° C. to about 8° C. for at least about twelve months. In some aspects, the antibody formulation contains at least about 98% by weight of antibody monomers, and less than about 2% by weight of antibody fragments, aggregates, and structurally altered forms with reduced tumor necrosis factor alpha binding activity and/or therapeutic efficacy when stored at about 2° C. to about 8° C. for at least about twelve months. In some aspects, the antibody formulation contains at least about 99% by weight of antibody monomers, and less than about 1% by weight of antibody fragments, aggregates, and structurally altered forms with reduced tumor necrosis factor alpha binding activity and/or therapeutic efficacy when stored at about 2° C. to about 8° C. for at least about twelve months. The amount of antibody monomers and antibody fragments, aggregates, and structurally altered forms may be determined according to any technique suitable in the art, including those described or exemplified herein, including any one or combination of dynamic light scattering (DLS), differential scanning calorimetry (DSC), size exclusion chromatography (SE-UPLC), non-reducing and reducing capillary electrophoresis SDS (NR CE-SDS and R CE-SDS), peptide mapping and particle counting (PC).

In some aspects, the antibody formulation contains at least about 90% by weight of antibody monomers, and less than about 10% by weight of antibody fragments, aggregates, and structurally altered forms with reduced tumor necrosis factor alpha binding activity and/or therapeutic efficacy when stored at about 2° C. to about 8° C. for at least about eighteen months. In some aspects, the antibody formulation contains at least about 93% by weight of antibody monomers, and less than about 7% by weight of antibody fragments, aggregates, and structurally altered forms with reduced tumor necrosis factor alpha binding activity and/or therapeutic efficacy when stored at about 2° C. to about 8° C. for at least about eighteen months. In some aspects, the antibody formulation contains at least about 95% by weight of antibody monomers, and less than about 5% by weight of antibody fragments, aggregates, and structurally altered forms with reduced tumor necrosis factor alpha binding activity and/or therapeutic efficacy when stored at about 2° C. to about 8° C. for at least about eighteen months. In some aspects, the antibody formulation contains at least about 96% by weight of antibody monomers, and less than about 4% by weight of antibody fragments, aggregates, and structurally altered forms with reduced tumor necrosis factor alpha binding activity and/or therapeutic efficacy when stored at about 2° C. to about 8° C. for at least about eighteen months. In some aspects, the antibody formulation contains at least about 97% by weight of antibody monomers, and less than about 3% by weight of antibody fragments, aggregates, and structurally altered forms with reduced tumor necrosis factor alpha binding activity and/or therapeutic efficacy when stored at about 2° C. to about 8° C. for at least about eighteen months. In some aspects, the antibody formulation contains at least about 98% by weight of antibody monomers, and less than about 2% by weight of antibody fragments, aggregates, and structurally altered forms with reduced tumor necrosis factor alpha binding activity and/or therapeutic efficacy when stored at about 2° C. to about 8° C. for at least about eighteen months. In some aspects, the antibody formulation contains at least about 99% by weight of antibody monomers, and less than about 1% by weight of antibody fragments, aggregates, and structurally altered forms with reduced tumor necrosis factor alpha binding activity and/or therapeutic efficacy when stored at about 2° C. to about 8° C. for at least about eighteen months. The amount of antibody monomers and antibody fragments, aggregates, and structurally altered forms may be determined according to any technique suitable in the art, including those described or exemplified herein, including any one or combination of dynamic light scattering (DLS), differential scanning calorimetry (DSC), size exclusion chromatography (SE-UPLC), non-reducing and reducing capillary electrophoresis SDS (NR CE-SDS and R CE-SDS), peptide mapping and particle counting (PC).

The invention also features methods for treating Rheumatoid Arthritis in a subject in need thereof by administering a therapeutically effective amount of any of the antibody formulations described or exemplified herein. The invention also features methods for treating Juvenile Idiopathic Arthritis, Psoriatic Arthritis, Ankylosing Spondylitis, Crohn's Disease, Plaque Psoriasis, Ulcerative Colitis, Inflammatory Bowel Disease, Hidradenitis Suppurativa, or Refractory Asthma by administering a therapeutically effective amount of any of the antibody formulations described or exemplified herein. Therapeutic efficacy is attained, for example, by the ONS-3010 antibody present in the administered formulation. Administration of the antibody formulation may be according to any suitable route, preferably by injection, and more preferably by subcutaneous injection. Administration may be carried out under the direction or supervision of a medical practitioner.

The antibody formulations described and exemplified herein may be for use as a medicament. The antibody formulations described and exemplified herein may be for use in the manufacture of a medicament. The formulations may be for use in the treatment of Rheumatoid Arthritis. The formulations may be for use in the treatment of Juvenile Idiopathic Arthritis. The formulations may be for use in the treatment of Psoriatic Arthritis. The formulations may be for use in the treatment of Ankylosing Spondylitis. The formulations may be for use in the treatment of Crohn's Disease. The formulations may be for use in the treatment of Plaque Psoriasis. The formulations may be for use in the treatment of Ulcerative Colitis. The formulations may be for use in the treatment of Inflammatory Bowel Disease. The formulations may be for use in the treatment of Hidradenitis Suppurativa. The formulations may be for use in the treatment of Refractory Asthma.

The invention also features kits. The kits may be used, for example, to practice any of the methods described or exemplified herein. In some aspects, a kit comprises any antibody formulation described or exemplified herein, and instructions for using the antibody formulation in any of the methods or uses described or exemplified herein. The kit may comprise a device for injecting the antibody formulation into a subject, including but not limited to a syringe and needle, or catheter.

The instructions included with the kit may include instructions for administering the antibody formulation in a method for treating Rheumatoid Arthritis, including instructions for injecting the antibody formulation into a Rheumatoid Arthritis patient in need thereof. In some aspects, the instructions included with the kit may include instructions for administering the antibody formulation in a method for treating Juvenile Idiopathic Arthritis, including instructions for injecting the antibody formulation into a Juvenile Idiopathic Arthritis patient in need thereof. In some aspects, the instructions included with the kit may include instructions for administering the antibody formulation in a method for treating Psoriatic Arthritis, including instructions for injecting the antibody formulation into a Psoriatic Arthritis patient in need thereof. In some aspects, the instructions included with the kit may include instructions for administering the antibody formulation in a method for treating Ankylosing Spondylitis, including instructions for injecting the antibody formulation into a Ankylosing Spondylitis patient in need thereof. In some aspects, the instructions included with the kit may include instructions for administering the antibody formulation in a method for treating Crohn's Disease, including instructions for injecting the antibody formulation into a Crohn's Disease patient in need thereof. In some aspects, the instructions included with the kit may include instructions for administering the antibody formulation in a method for treating Plaque Psoriasis, including instructions for injecting the antibody formulation into a Plaque Psoriasis patient in need thereof. In some aspects, the instructions included with the kit may include instructions for administering the antibody formulation in a method for treating Ulcerative Colitis, including instructions for injecting the antibody formulation into a Ulcerative Colitis patient in need thereof. In some aspects, the instructions included with the kit may include instructions for administering the antibody formulation in a method for treating Inflammatory Bowel Disease, including instructions for injecting the antibody formulation into an Inflammatory Bowel Disease patient in need thereof. In some aspects, the instructions included with the kit may include instructions for administering the antibody formulation in a method for treating Hidradenitis Suppurativa, including instructions for injecting the antibody formulation into a Hidradenitis Suppurativa patient in need thereof. In some aspects, the instructions included with the kit may include instructions for administering the antibody formulation in a method for treating Refractory Asthma, including instructions for injecting the antibody formulation into a Refractory Asthma patient in need thereof.

The following examples are provided to describe the invention in greater detail. They are intended to illustrate, not to limit, the invention.

EXAMPLE 1

Materials and Methods

Introduction. Antibody ONS-3010 represents a biosimilar of adalimumab, and has been reformulated for enhanced storage stability. It is believed that the modifications to the buffer of the formulation composition may reduce the incidence of injection-site reaction, including injection pain and a burning sensation observed from subcutaneous administration of adalimumab (Kaiser C et al. (2012) Rheumatol. Int. 32:295-9, and Fransson J et al. (1996) J. Pharm. Pharmacol. 48:1012-5). Current adalimumab formulations include (in addition to the antibody), sodium chloride, monobasic sodium phosphate dihydrate, dibasic sodium phosphate dihydrate, sodium citrate, citric acid monohydrate, mannitol, polysorbate 80, and sterile water for injection. The experimental approach described below included three experimental series of development work to reformulate adalimumab for therapeutic administration.

The first experimental series of studies focused on buffer composition, strength, and ability to achieve the desired pH of about 5.2. The second experimental series of experiments utilized stressed stability studies with refined set of formulation conditions based on results of experimental series 1. Sodium chloride concentration was probed in experimental series 2. The third experimental series of formulation development studies compared three conditions, including a control of the adalimumab reference product buffer (per 0.8 ml: 40 mg adalimumab, 4.93 mg sodium chloride, 0.69 mg monobasic sodium phosphate dihydrate, 1.22 mg dibasic sodium phosphate dihydrate, 0.24 mg sodium citrate, 1.04 mg citric acid monohydrate, 9.6 mg mannitol, 0.8 mg polysorbate 80, and Q.S. sterile water for injection, pH 5.2). For each buffer system, there was one condition for the adalimumab reference formulation level of NaCl and mannitol, and a condition where those levels were modified relative to the adalimumab reference formulation (lower NaCl, higher mannitol (LS/HM)). These modifications resulted in formulations of comparable osmolality to the adalimumab reference formulation, while maintaining isotonicity.

Dynamic Light Scattering (DLS). The DLS testing method used a Wyatt DynaPro™ Plate Reader to provide information on protein size distribution and overall colloidal stability in solution. Hydrodynamic radius provided information on the presence of aggregation and confirmation of the molecule's structure in solution. DLS testing provided an orthogonal measure of size distribution in solution under non-denaturing conditions.

Differential Scanning calorimetry (DSC). Differential scanning calorimetry measured the melting transitions for the protein and, thus, provided information on protein thermal stability in solution. Calorimetry was performed using a GE VP Capillary DSC system. The protein was heated from 25° C. to 95° C. at an optimized scan rate allowing the melting transitions (Tm) to occur while the protein is unfolding. A buffer control was heated alongside the sample and used to calculate melting temperatures and transitions. The DSC profile was typical of antibodies and demonstrated that the protein folded into distinct domains.

Size Exclusion Chromatography (SE-UPLC). SE-UPLC was used to monitor ONS-3010 size variant distribution. The SE-UPLC testing method separates proteins based on size. The method is isocratic with a sodium phosphate running buffer, using a Waters Acquity UPLC BEH200 SEC column (1.7 μm, 4.6×150 mm). Peaks were monitored using absorbance at 280 nm. Species eluting before the monomer peak were aggregates (HMWS) and peaks eluting after the monomer peak were degradants (LMWS).

NonReducing and Reducing Capillary Electrophoresis SDS (NR CE-SDS and R CE-SDS). CE-SDS analysis was used to compare ONS-3010 size variants under denaturing conditions, with both non-reducing and reducing conditions, using a Beckman PA800 plus instrument. Capillary gel electrophoresis provides automated analysis of reduced and non-reduced proteins by size to determine protein purity and/or heterogeneity. Samples were treated with either an alkylation or reducing agent and SDS was bound to all proteins via a sample buffer. A polymer matrix was filled into the capillary prior to sample analysis. Samples were electrokinetically introduced to the capillary by an applied voltage, then electrophoresis was performed by applying a constant voltage to the capillary. The SDS treated proteins have mass to charge properties that are proportional to the protein weights, which allows for the separation of the SDS-bound proteins by the differences in molecular weight. Test article proteins were quantified by UV detection at 220 nm.

Modulation of TNF-alpha activity: L929 Cell-Based Bioassay. The primary mechanism of action of adalimumab is the neutralization of circulating TNF-alpha. L929 cell-based bioassay measures cell death/viability. TNF-alpha induces cytotoxicity in L929 cells; relative potency of adalimumab was measured by monitoring live cells through a luminescent tag.

Peptide mapping. N-terminal sequence variants, C-terminal sequence variants, oxidation, deamidation, succinimide formation, isomerization are measured using peptide mapping LC-MS methodologies.

Particle count. The level of aggregates and particulates is a critical quality attribute to assess for liquid protein formulations. The presence of aggregates and particulates may negatively impact product quality.

EXAMPLE 2

Results

Figure 2:
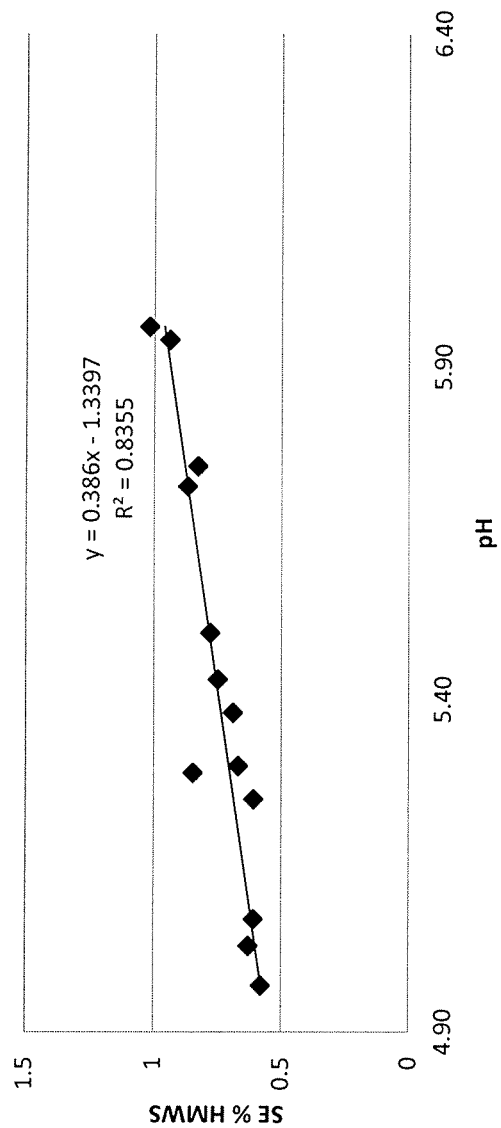
FIG. 2 shows trends in SE-UPLC % high molecular weight species (HMWS) as a function of solution pH.

Experimental series 1. The first experimental series of studies focused on buffer composition, strength, and ability to achieve the desired pH of 5.2. Buffers tested included citrate and phosphate (which are used in the reference product formulation) and acetate (Table 1). Sodium chloride and mannitol concentrations (equivalent to those in adalimumab reference formulation) were added to conditions throughout experimental series 1 experiments. From this experimental series of experiments, it was observed that some buffers were better than others at achieving and maintaining the desired pH in the range of 4.9-5.5 (0.3 pH units outside of the adalimumab reference formulation). SE-UPLC purity, in particular, was highly correlated with pH, and the use of acetate buffer resulted in preferable profiles (FIGS. 1 and 2).

TABLE 1

Round 1 Formulation Conditions

| Description | Citrate | Phosphate | Acetate | NaCl | Mannitol | Target pH 4.9 | Target pH 5.2 | Target pH 5.5 |
|---|---|---|---|---|---|---|---|---|
| Adalimumab reference | Y | Y | | | Y | Y | | Y | Y |
| Citrate low | 10 mM | | | | Y | Y | Y | Y | Y |
| Citrate high | 20 mM | | | | Y | Y | Y | Y | Y |
| Acetate low | | | | 10 mM | Y | Y | Y | Y | Y |
| Acetate high | | | | 20 mM | Y | Y | Y | Y | Y |

Figure 3:
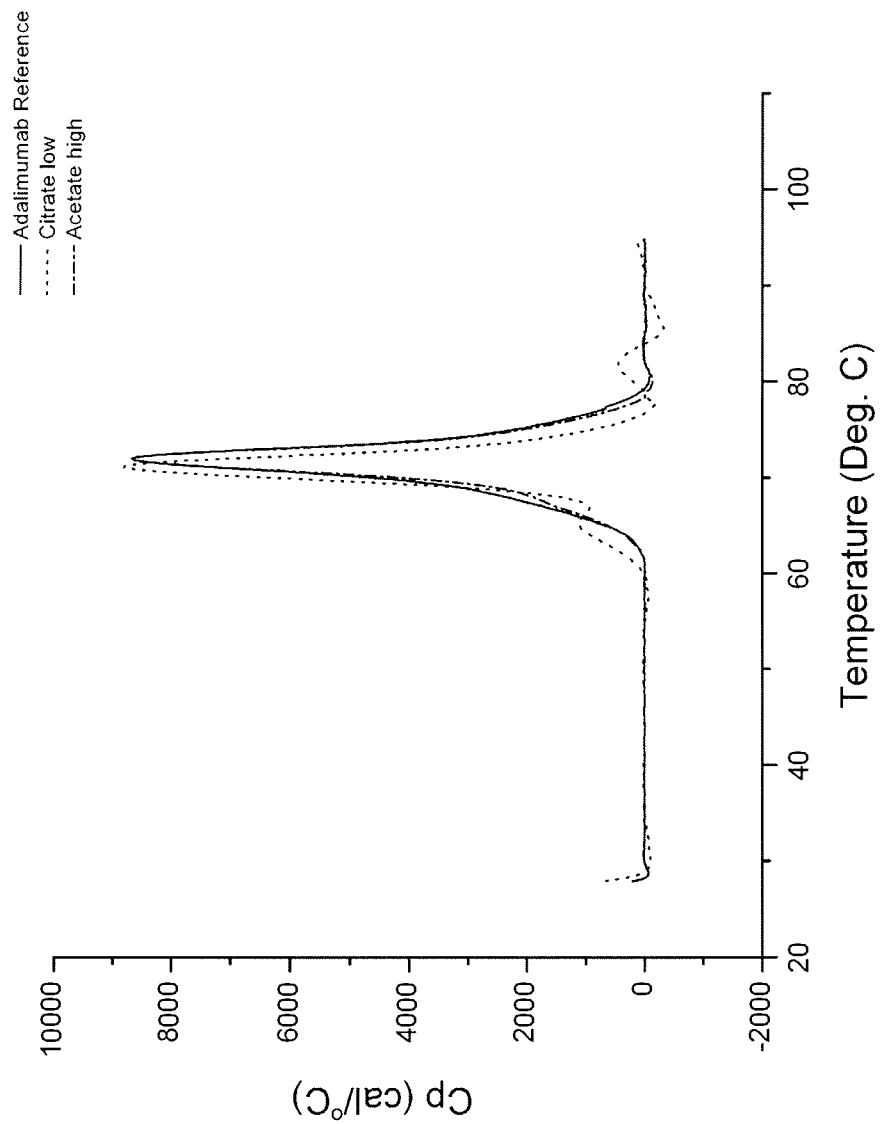
FIG. 3 shows a DSC thermograms for representative experimental series 1 formulation conditions.

Y: NaCl and mannitol included at Adalimumab reference buffer concentrations of 4.93 mg/0.08 mL and 9.6 mg/0.8 mL, respectively DSC thermograms were helpful in assessing product stability toward thermal denaturation. All traces showed two dominant thermal transitions: a larger one after 72° C., and a smaller one after 80° C. Under certain conditions, an additional shoulder is seen after 60° C., which is believed to indicate the beginning of an unfolding process under these formulation conditions (FIG. 3). These latter formulations were excluded from subsequent experimental series of screening.

Figure 4:
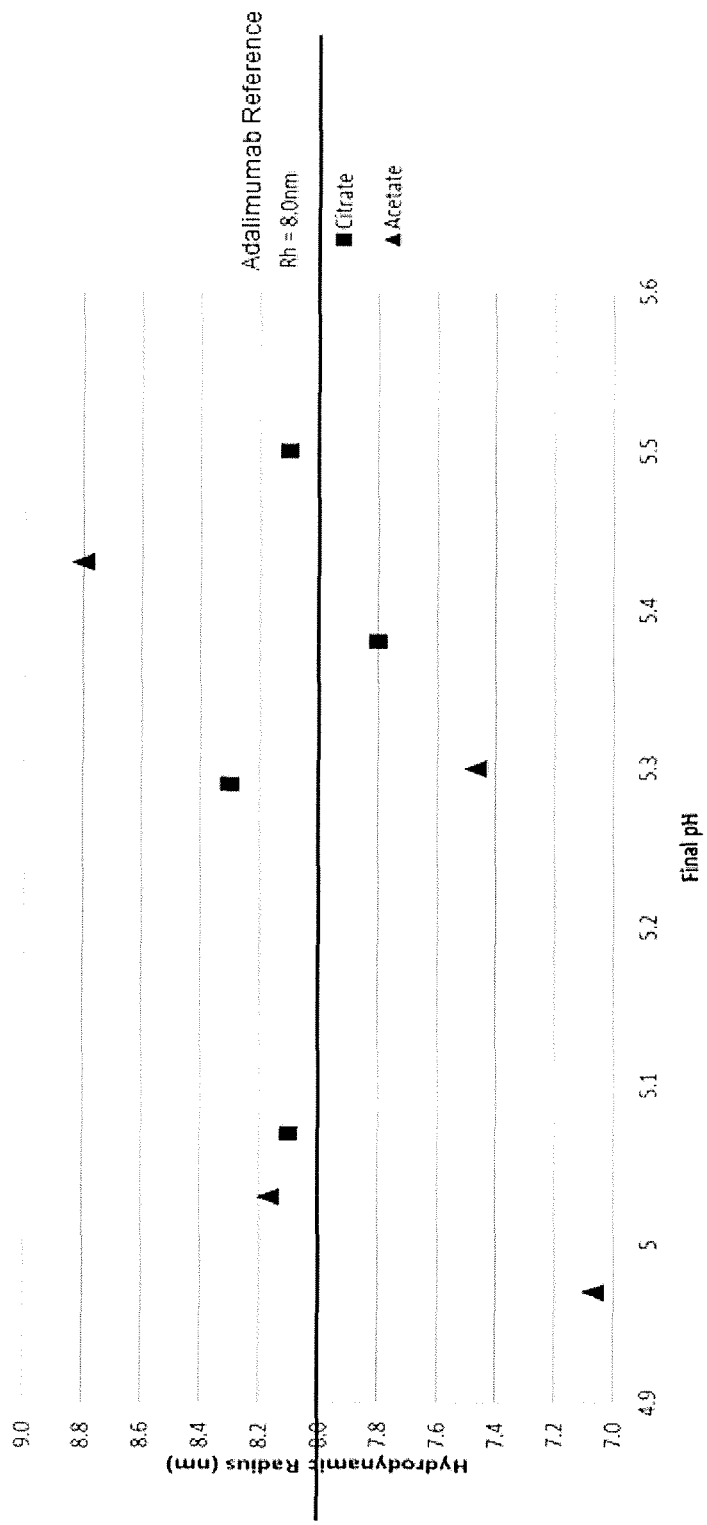
FIG. 4 shows a DLS and pH ranges for formulation solutions at 50 mg/ml protein concentration, coded by buffer composition.

Dynamic light scattering (DLS) was used to monitor the hydrodynamic radius Rh (size) of protein molecules in solution. Hydrodynamic radius size in the 5-6 nanometer range under lower (~1 mg/mL) protein concentration are typical for monomeric monoclonal antibodies (about 140 kDa in size); this size increases with protein concentration, possibly due to crowding, self-association, or aggregation. Such higher sizes should typically be avoided under formulation conditions since they are indicative of an inherently unstable condition. Hydrodynamic radii of ONS-3010 in experimental series 1 formulation conditions were monitored at two protein concentrations for more complete picture of colloidal stability. Rh was not dominated by pH (FIG. 4): there was considerable variation in Rh even within a relatively narrow pH range, underscoring the impact of buffer composition on colloidal stability. The conditions that had Rh ≤ adalimumab reference formulation of 8.0 nm were selected for further evaluation in experimental series 2.

Experimental series 2. The second experimental series utilized stressed stability studies with a refined set of formulation conditions based on results of experimental series 1. Acetate buffer is of particular interest at the 20 mM level. Sodium chloride concentration was also evaluated. Some conditions matched the adalimumab reference formulation NaCl levels, while others did not contain NaCl (Table 2).

TABLE 2

Experimental Series 2 Formulation Conditions

| Description | Citrate | Phosphate | Acetate | NaCl | Mannitol |
|---|---|---|---|---|---|
| Adalimumab reference | Y | Y | | Y | Y |
| Acetate high with NaCl | | | 20 mM | Y | Y |
| Acetate high no NaCl | | | 20 mM | N | Y |

Figure 5:
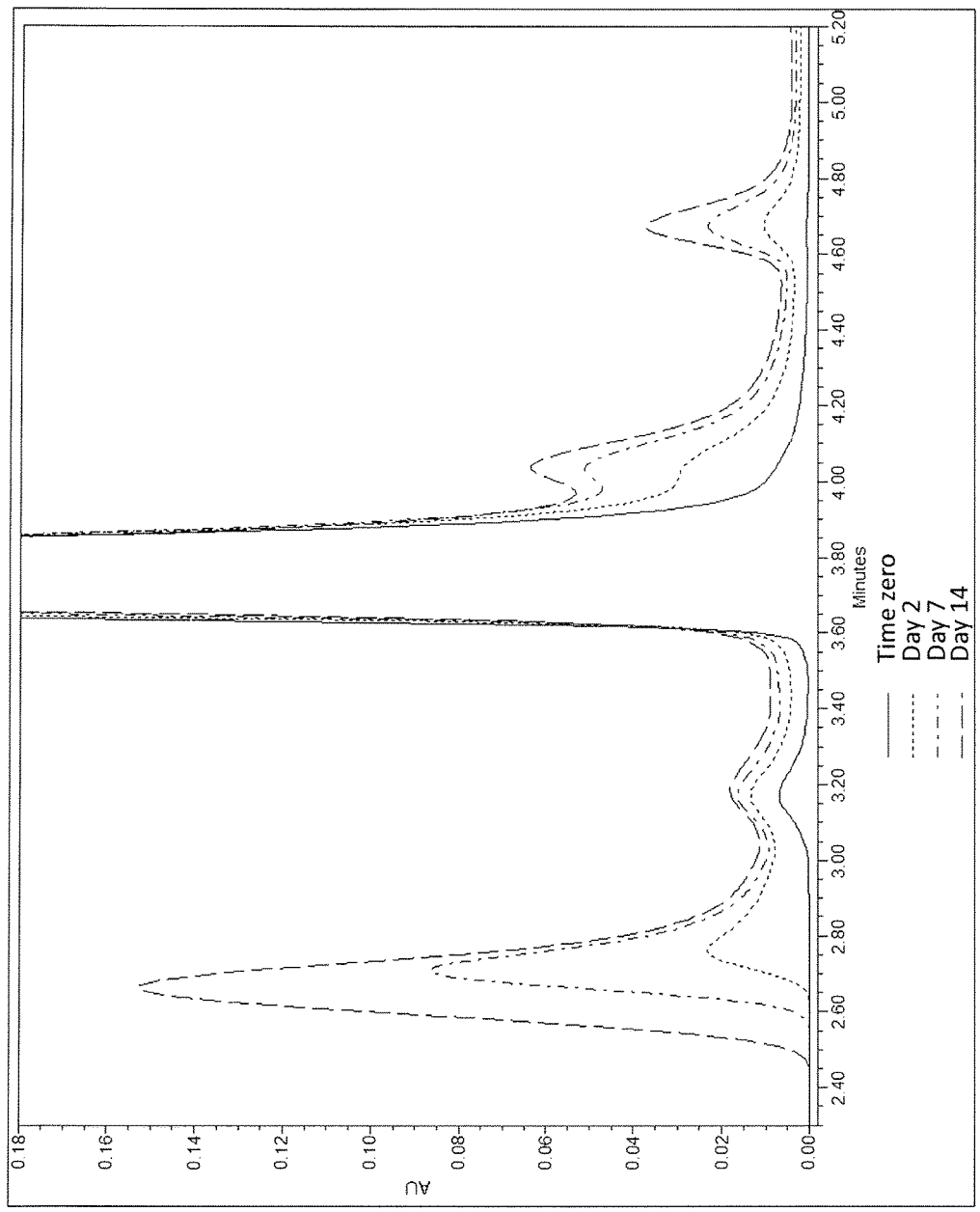
FIG. 5 shows an overlay of SE-UPLC chromatograms for the adalimumab reference formulation under duration of stressed stability experiment (55° C. up to 14 days).
Figure 6:
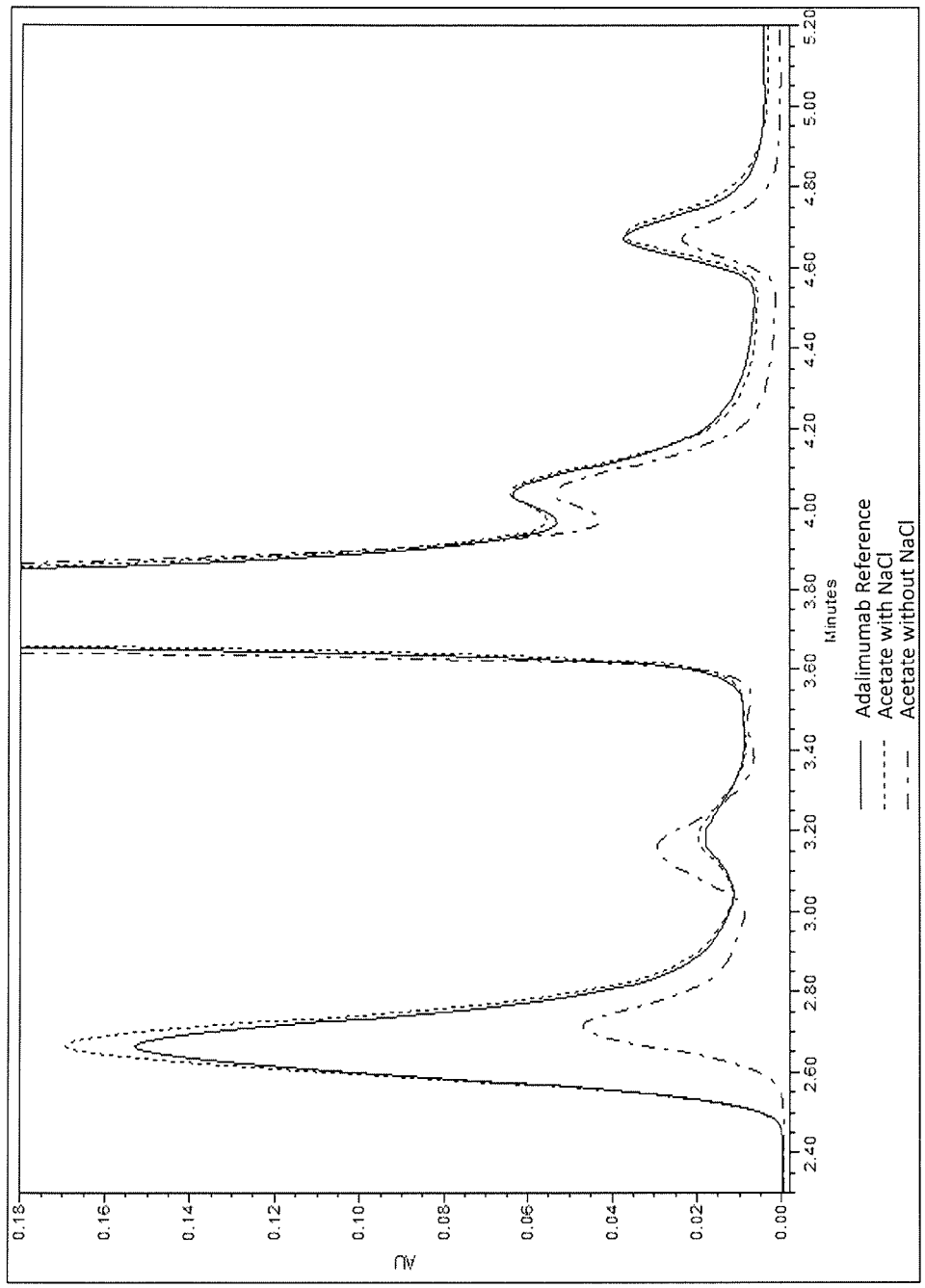
FIG. 6 shows an overlay of representative SE-UPLC chromatograms from experimental series 2 formulation conditions of ONS-3010.
Figure 7:
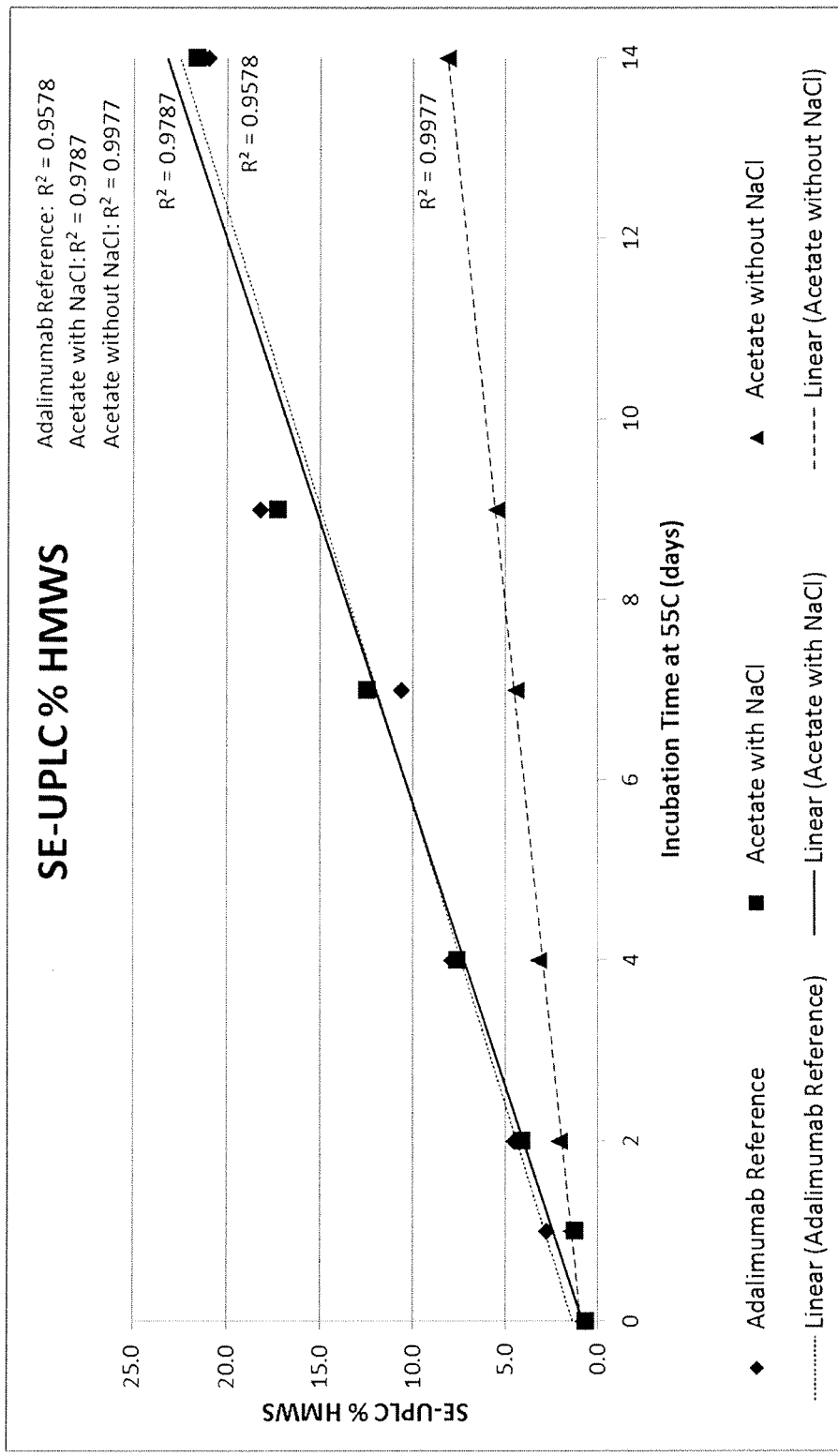
FIG. 7 shows trends in SE-UPLC aggregation over time at stressed conditions.
Figure 8:
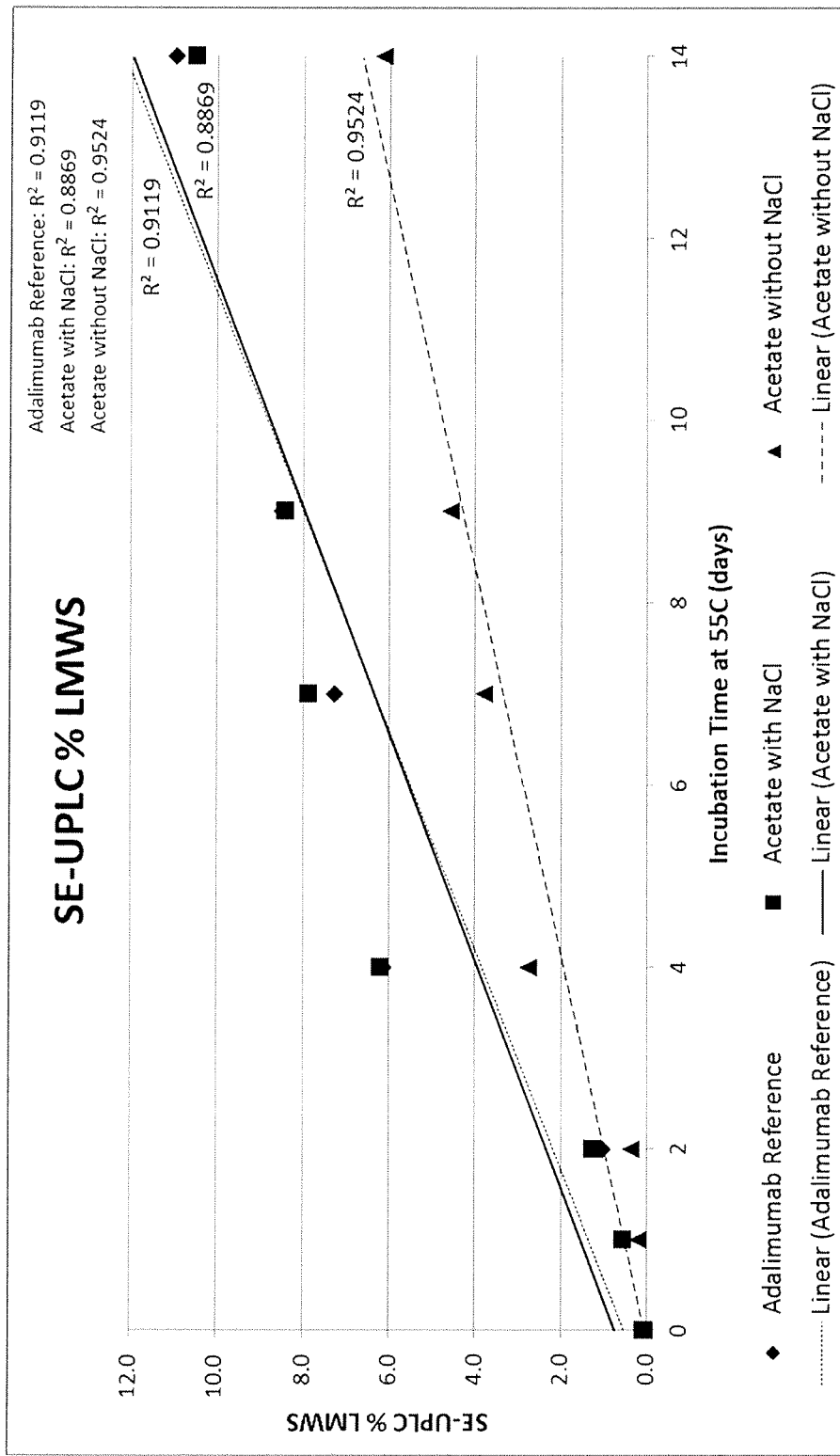
FIG. 8 shows trends in SE-UPLC fragmentation over time at stressed conditions.

Y: NaCl and mannitol included at Adalimumab reference (AR) buffer concentrations (4.93 mg/0.8 mL and 9.6 mg/0.8 mL, respectively).
N: no NaCl added Experimental series 2 formulation buffers containing NaCl were less stable upon incubation at 55° C. for up to 14 days as compared to the buffers without NaCl. As shown in FIG. 5, time at elevated temperature caused both aggregation (increasing SE-UPLC high molecular weight species or HMWS), as well as degradation and fragmentation (increasing low molecular weight species or LMWS). Formulation conditions containing NaCl in these experiments showed comparable rates of aggregation and fragmentation relative to that of the adalimumab reference formulation. Formulations lacking NaCl, however, exhibited improved stability toward both mechanisms of aggregation and degradation. This is illustrated in FIG. 6, which displays overlaid chromatograms of ONS-3010 formulated with the adalimumab reference buffer, formulated with a NaCl-containing acetate buffer, and formulated with an acetate buffer without NaCl. FIG. 7 and FIG. 8 highlight trends in SE-UPLC aggregation and fragmentation, respectively.

The removal of NaCl appeared to also correlate with improved colloidal stability as measured by DLS, and with improved stability in CEX-HPLC. For experimental series 3, lower NaCl conditions were designed which reduced (but did not eliminate) NaCl levels, while adjusting mannitol concentrations to result in osmolality levels close to that of reference product formulation.

Table 3 below summarizes the experimental series 2 conditions and their analytical results, highlighting reasons for their inclusion or exclusion from experimental series 3 investigations. In general, conditions selected for experimental series 3 showed comparable or improved stability toward thermal and chemical denaturation as monitored by a variety of orthogonal techniques (SE-UPLC, CEX-HPLC, CE-SDS). Relative potency was also assessed using the L929 cell-based potency assay, and colloidal stability was monitored with DLS. Finally, all samples were visually monitored throughout the study (and haziness upon dilution for testing became an exclusion criterion).

TABLE 3

Experimental Series 2 Data Summary

| | 55° C. | | | | | 37° C. | | Decision |
|---|---|---|---|---|---|---|---|---|
| Condition | SE (Δ % main/7 d) | CEX (Δ % basic/2 d) | CE-SDS (NR Δ % main/7 d) | Visual | Bioassay | SE (Δ % main/28 d) | DLS (Rh) | for Experimental Series 3 |
| Adalimumab Reference | −17.2 | 3.4 | −14.0 | Clear | Control | −4.5 | 7.4 nm | Control |
| Acetate high with NaCl | −19.6 | 4.1 | −12.5 | Hazy upon dilution | Comparable to Adalimumab Reference | −4.5 | 7.1 nm | Include |
| Acetate high no NaCl | −7.4 | 0.7 | −5.5 | Clear | Improvement relative to Adalimumab Reference | −2.8 | 3.0 nm | Include with modifications |

Experimental series 3. The final experimental series of formulation development studies compares three conditions including the adalimumab reference formulation as a control (Table 4). The other two reformulation conditions use acetate buffer. There is one acetate buffer matching the adalimumab reference level of NaCl and mannitol, and an acetate buffer where those levels are modified relative to the adalimumab reference (AR) formulation (lower NaCl, higher mannitol(LS/HM)). These modifications result in formulations of comparable osmolality to the adalimumab reference, maintaining isotonicity.

TABLE 4

Experimental Series 3 Formulation Conditions.

| Condition # | Description | Citrate | Phosphate | Acetate | NaCl | Mannitol | Polysorbate 80 |
|---|---|---|---|---|---|---|---|
| 1 | Adalimumab Reference (AR) | Y | Y | | Y | Y | Y |
| 2 | Acetate | | | 20 mM | AR level | AR level | AR level |
| 3 | Acetate LS/HM | | | 20 mM | Lower | Higher | AR level |

Y: NaCl and mannitol included at Adalimumab reference (AR) buffer concentrations (4.93 mg/0.8 mL and 9.6 mg/0.8 mL, respectively).
LS/HM: lower NaCl and higher mannitol levels.

A comprehensive series of stressed, accelerated, and real-time stability studies were executed as part of experimental series 3 formulation development (Table 5). Real-time studies were conducted in glass vials, both to provide a container contact similar to that in final drug product presentation (type 1 borosilicate glass) and to facilitate assessment of product appearance and particle formation. In addition to incubation of ONS-3010 under different temperatures as a liquid, the product will be stored under frozen conditions (both −20° C. and −80° C.) as well as exposed to repetitive cycles of frozen to liquid transitions. A forced oxidation study and a shaking/shear force study provide additional information to help inform final formulation selection.

TABLE 5

Components and Scope of Round 3 Experiments.

| Study Element | Condition | Duration | Analytical Testing | Findings |
|---|---|---|---|---|
| Stressed stability | 55° C. | Up to 7 days | SE-UPLC, CE-SDS, CEX-HPLC, peptide mapping, L929 bioassay | Condition 3 best across all assays |
| Accelerated stability | 37° C. | Up to 28 days | SE-UPLC, CE-SDS, CEX-HPLC, peptide mapping, L929 bioassay, appearance | Acetate formulations comparable to Adalimumab reference for CEX-HPLC, SE-UPLC, CE-SDS, peptide map and bioassay. |
| | 25° C. | Up to 28 days | SE-UPLC. CE-SDS, CEX-HPLC, peptide mapping, L929 bioassay, appearance | Acetate formulations comparable to Adalimumab reference for CEX-HPLC, SE-UPLC, CE-SDS, peptide map and bioassay. |
| Real-time stability | 2-8° C. | 0.1 m, 5 m, 12 m, 18 m | SE-UPLC, CE-SDS, CEX-HPLC, peptide mapping, L929 bioassay, particle count, appearance | All formulations comparable to Adalimumab reference. Lower salt condition 3 reduces particles up to 28 days. Particle count at 28 day better than Adalimumab reference. |
| Additional characterization | At time zero | At time zero | DLS, DSC, osmolality, Particle count | All formulations DLS comparable or better than Adalimumab reference. Lower salt helps Rh. Osmolality all isotonic. Particle count T = 0 comparable or better than Adalimumab reference. |

TABLE 5-continued

Components and Scope of Round 3 Experiments.

| Study Element | Condition | Duration | Analytical Testing | Findings |
|---|---|---|---|---|
| Forced oxidation | 1% t-butyl hydrogen peroxide, 25° C. | Up to 8 hours | SE-UPLC, CEX-HPLC, peptide mapping | No change in SE-UPLC, slight changes in CEX (condition 3 better), clear oxidation in peptide map (condition 3 better) |
| Frozen stability | −80° C. | 0.1 m, 5 m, 12 m, 18 m | SE-UPLC, CE-SDS, CEX-HPLC, peptide mapping, L929 bioassay | All formulations comparable to Adalimumab reference |
| Freeze-thaw cycles | −20° C. and −80° C. | Up to 5 cycles | SE-UPLC, CE-SDS (NR) | −20° C. shows some HMWS (noncovalent) with higher mannitol, all formulations comparable to Adalimumab reference at −80° C. |
| Shaking study | 37° C., with and without Tween | Up to 28 days | SE-UPLC, CE-SDS, CEX-HPLC, L929 bioassay, selected peptide map, appearance | All conditions show comparable or better protection to shear relative to Adalimumab reference for SE-UPLC, CE-SDS and bioassay. CEX showed acetate conditions comparable to Adalimumab reference. |

EXAMPLE 3

Characterization of Material

Figure 9:
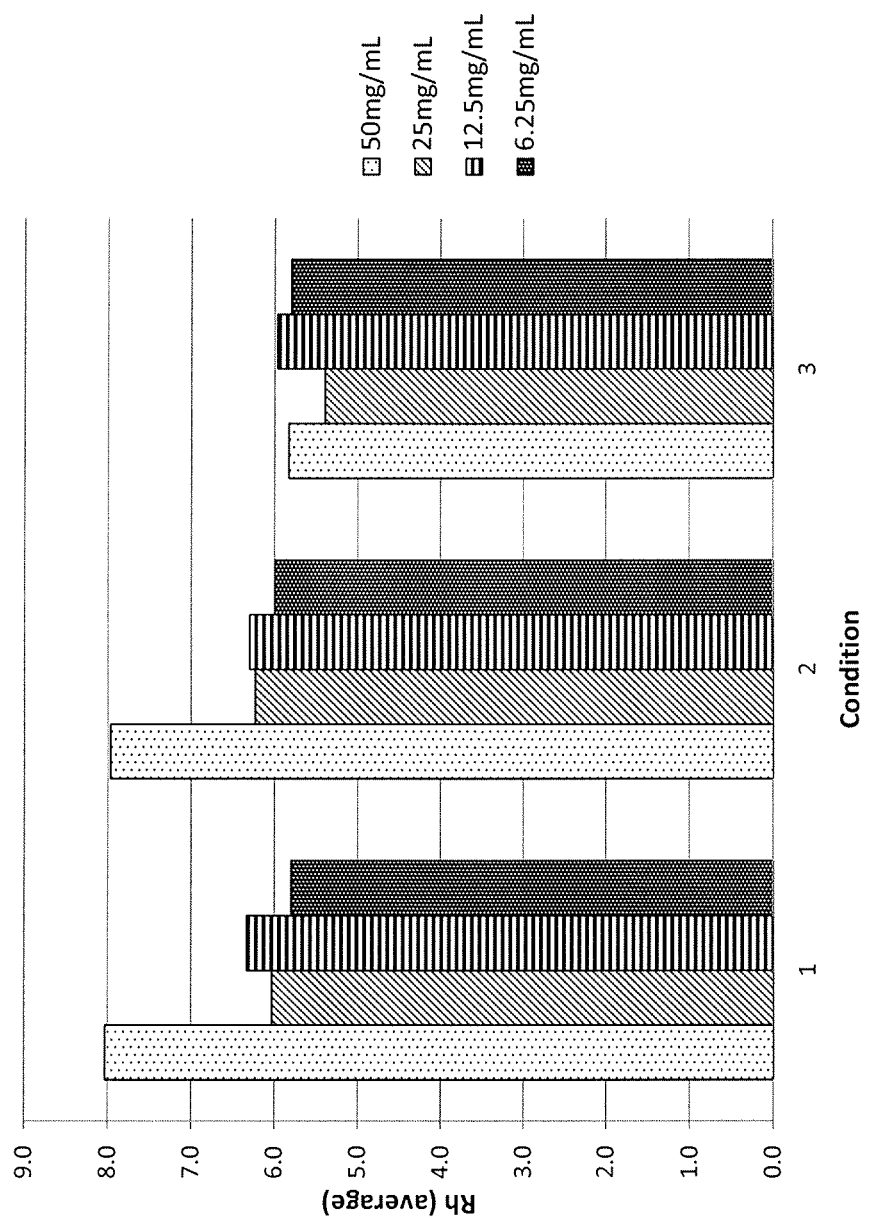
FIG. 9 shows ONS-3010 experimental series 3 DLS results.

Dynamic Light Scattering. Dynamic Light Scattering was used to measure the hydrodynamic radius (Rh) of ONS-3010 at four different protein concentrations (see FIG. 9 for graphical representation of the results). The adalimumab reference formulation, at 50 mg/ml, has an average hydrodynamic radius of 8.0 nm. Condition 2 (acetate) shows similar values at the full 50 mg/ml concentration, while condition 3 (acetate LS/HM) with lower salt shows a smaller Rh value, correlated with better control of self-association at higher protein concentrations. Lower amounts of sodium chloride as used in condition 3 are enough to disrupt the crowding/association taking place at 50 mg/mL used under typical formulation conditions. At lower concentrations, Rh values converge on values in the 5-6 nm range, typical for monomeric monoclonal antibodies. Condition 3 (Acetate LS/HM) results in the lowest Rh values over the entire range of protein concentrations measured.

Figure 11:
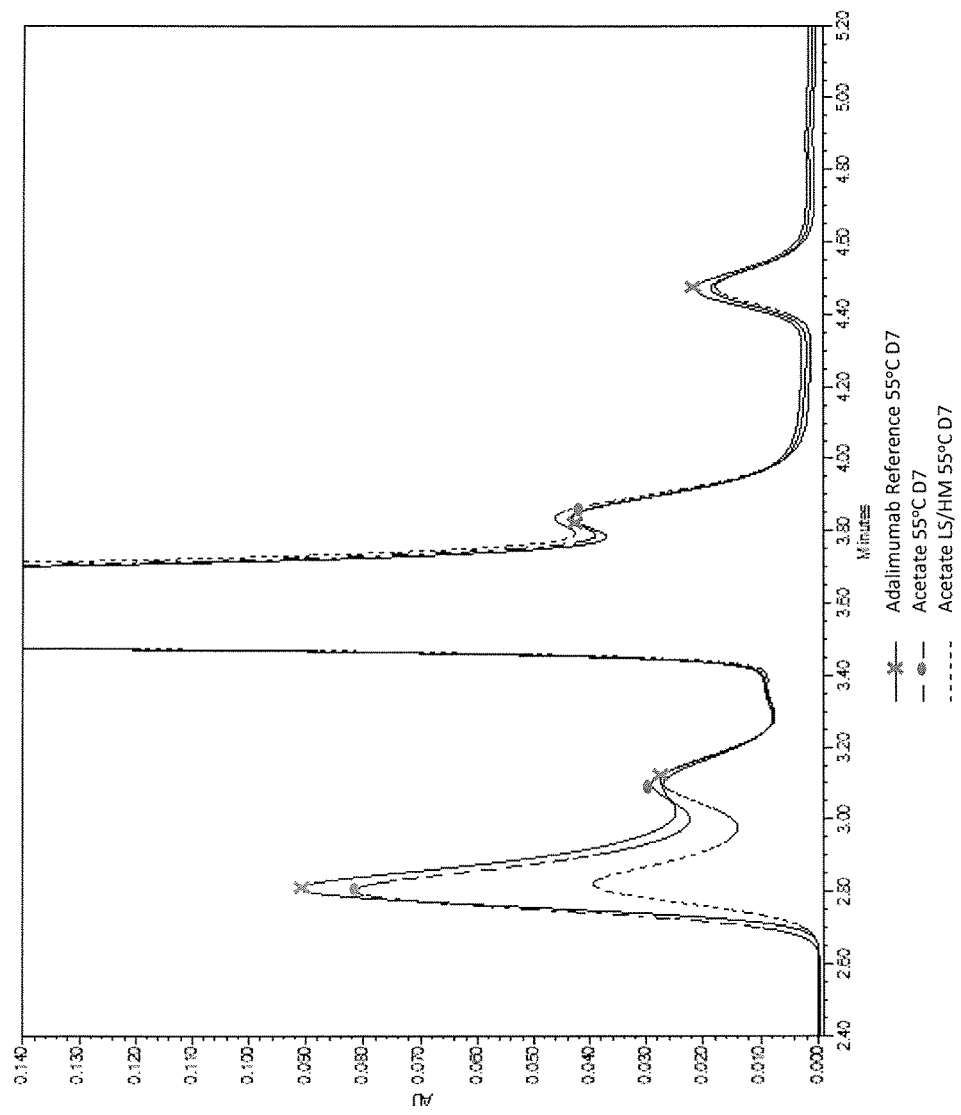
FIG. 11 shows an overlay of representative SE-UPLC chromatograms from experimental series 3 ONS-3010 formulation conditions.
Figure 12:
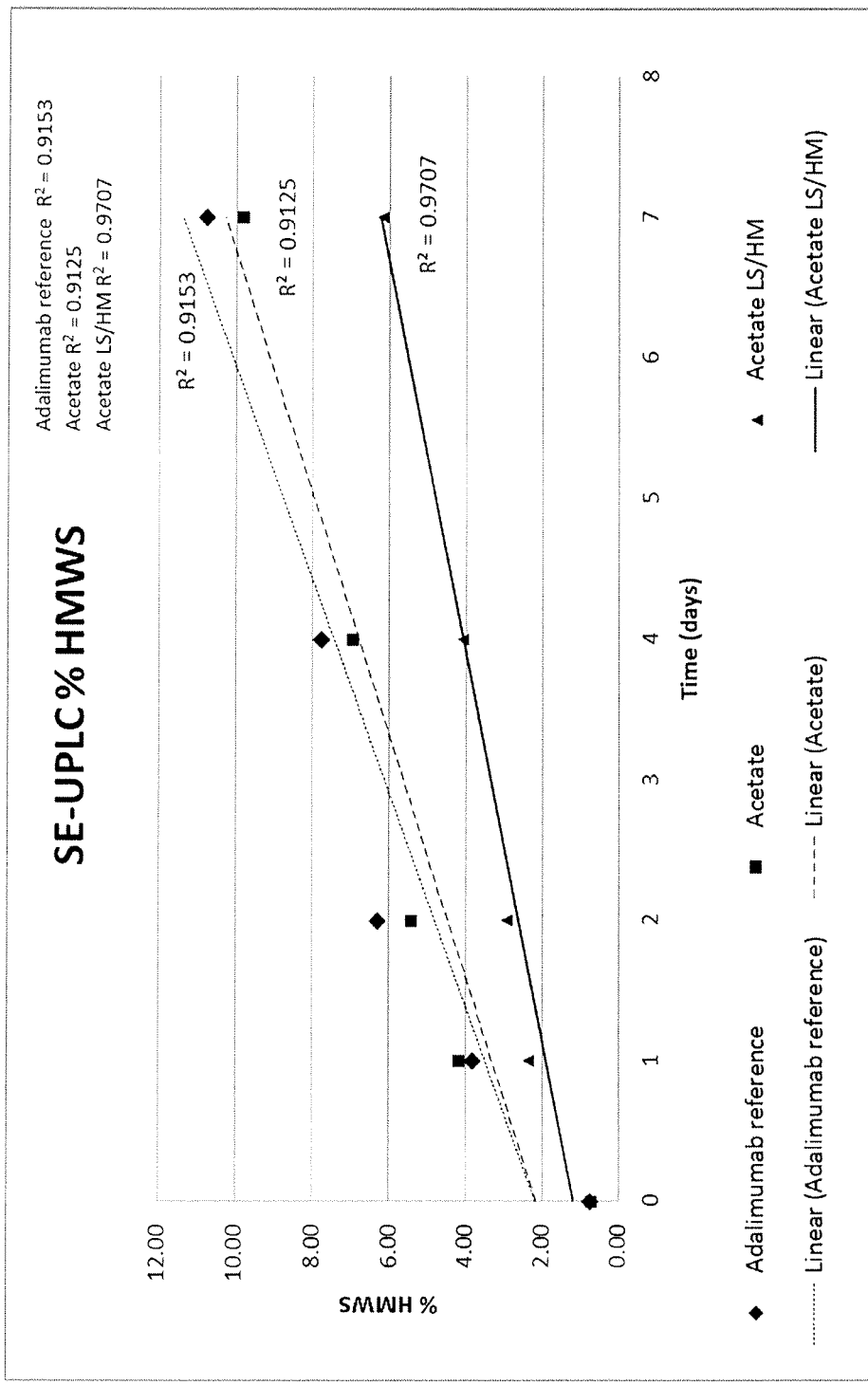
FIG. 12 shows trends in experimental series 3 SE-UPLC aggregation over time at stressed conditions.

The presence of minor quantities of sodium chloride (26.35 mM Sodium Chloride vs. 105.45 mM Sodium Chloride) in the buffered formulation prevents crowding of the individual antibody molecules at high protein concentrations of 50 mg/mL. This phenomenon is further confirmed by a lower hydrodynamic radius for the low sodium chloride containing the buffered formulation (FIG. 9 Acetate LS/HM buffer Condition 3 50 mg/mL). This is a unique synergistic effect of sodium chloride (lower concentrations) with acetate buffer that prevents crowding and reduces aggregation (HMWS) (FIGS. 11 and 12). It is believed that lower concentrations of sodium chloride and the absence of citrate in the formulation could be associated with better patient acceptability (reduced irritation and pain at site of injection). Modification of the buffer composition (lower concentration or removal of citrate, specifically) may reduce the incidence of injection-site reaction (e.g., a "burning sensation") upon subcutaneous administration of the drug.

Another such ONS-3010 material from the 200 L pilot scale was tested for its colloidal properties at ~50 mg/mL after storage in a glass vial (type I borosilicate) for 17 months at 2-8° C. The tested lot was formulated into both the acetate LS/HM buffer formulation (BDS-O) and the adalimumab reference formulation (BDS-H). As shown in Table 6, the hydrodynamic radius for BDS-O is about 5.5 nm, which is significantly lower than that for BDS-H (7.9 nm). This difference in hydrodynamic radius (Rh) is indicative of increased colloidal stability in the buffered formulation compared to the adalimumab reference formulation. Moreover this important colloidal property (Rh) remains unchanged over the storage period of 17 months at 2-8° C., indicating greater storage stability for the buffered formulation.

TABLE 6

ONS-3010 DLS results.

| Sample | Protein concentration (mg/mL) | Avg. Rh (nm) |
|---|---|---|
| BDS-O | 49.9 | 5.5 |
| Adalimumab reference (BDS-H) | 53.7 | 7.9 |

Osmolarity. Osmolality values for the three conditions were measured using the Nova Flex instrument. All conditions were similar to one another and to the adalimumab reference formulation, and were in the isotonic range of 290-340 mOsm/kg (Table 7).

TABLE 7

ONS-3010 Experimental Series 3 Osmolality Values

| Condition # | Description | Osmolality (mOsm/kg) |
|---|---|---|
| 1 | Adalimumab reference | 330 |
| 2 | Acetate | 320 |
| 3 | Acetate LS/HM | 324 |

Refer to Table 4 for buffer components. LS/HM: Lower NaCl and higher mannitol levels Particle Count. Particle analysis was conducted using a HIAC Model 9703+ system following a modified USP method (allowing for detection of particles as small as 2 µm). Cumulative results for all size ranges are shown in Table 8, with counts per container calculated based on the 0.8 ml pre-filled syringe presentation. The 10 and 25 µm size bins are specifically tracked per the USP method <788>. Values for all conditions are well below the limits of ≤600 cumulative counts per container for ≥25 micron particles, and ≤6000 cumulative counts per container for ≥10 micron particles. Lower salt (formulation condition 3) appears to further reduce particles at 2-10 micron relative to the adalimumab reference formulation and the higher salt formulation (Table 8).

TABLE 8

Particle Count Results for Experimental Series 3 Time Zero and Day 28 Samples

| Sample | Particle Size (µm) | Time Zero Avg. Cumulative Counts/mL | Counts/ container | Day 28 2-8° C. Avg. Cumulative Counts/mL | Counts/ container |
|---|---|---|---|---|---|
| Adalimumab Reference | 2 | 1932 | 1546 | 1946 | 1557 |
|  | 3 | 1020 | 816 | 1332 | 1066 |
|  | 5 | 198 | 158 | 304 | 243 |
|  | 10 | 56 | 45 | 40 | 32 |
|  | 15 | 28 | 22 | 20 | 16 |
|  | 25 | 10 | 8 | 6 | 5 |
|  | 50 | 2 | 2 | 0 | 0 |
|  | 100 | 2 | 2 | 0 | 0 |
| Acetate | 2 | 808 | 646 | 1788 | 1430 |
|  | 3 | 396 | 317 | 1058 | 846 |
|  | 5 | 96 | 77 | 214 | 171 |
|  | 10 | 30 | 24 | 36 | 29 |
|  | 15 | 10 | 8 | 22 | 18 |
|  | 25 | 6 | 5 | 6 | 5 |
|  | 50 | 4 | 3 | 0 | 0 |
|  | 100 | 0 | 0 | 0 | 0 |
| Acetate LS/HM | 2 | 356 | 285 | 290 | 232 |
|  | 3 | 240 | 192 | 178 | 142 |
|  | 5 | 112 | 90 | 72 | 58 |
|  | 10 | 56 | 45 | 18 | 14 |
|  | 15 | 30 | 24 | 10 | 8 |
|  | 25 | 12 | 10 | 0 | 0 |
|  | 50 | 2 | 2 | 0 | 0 |
|  | 100 | 0 | 0 | 0 | 0 |

Refer to Table 4 for buffer components.
LS/HM: Lower NaCl and higher mannitol levels Stressed Stability (55° C.). To probe the behavior of ONS-3010 toward a stressed condition of elevated temperature, samples were incubated at 55° C. for up to 7 days, and then tested by multiple analytical methods. While 55° C. is well above storage conditions and any expected short-term handling conditions that would be encountered in the clinic, the stressed stability arm is extremely useful at highlighting formulation ability to protect from a myriad of forced degradation events that dominate at higher temperature. For both adalimumab and ONS-3010, 55° C. is lower than the initial onset of thermal denaturation as monitored by differential scanning calorimetry.

Figure 10:
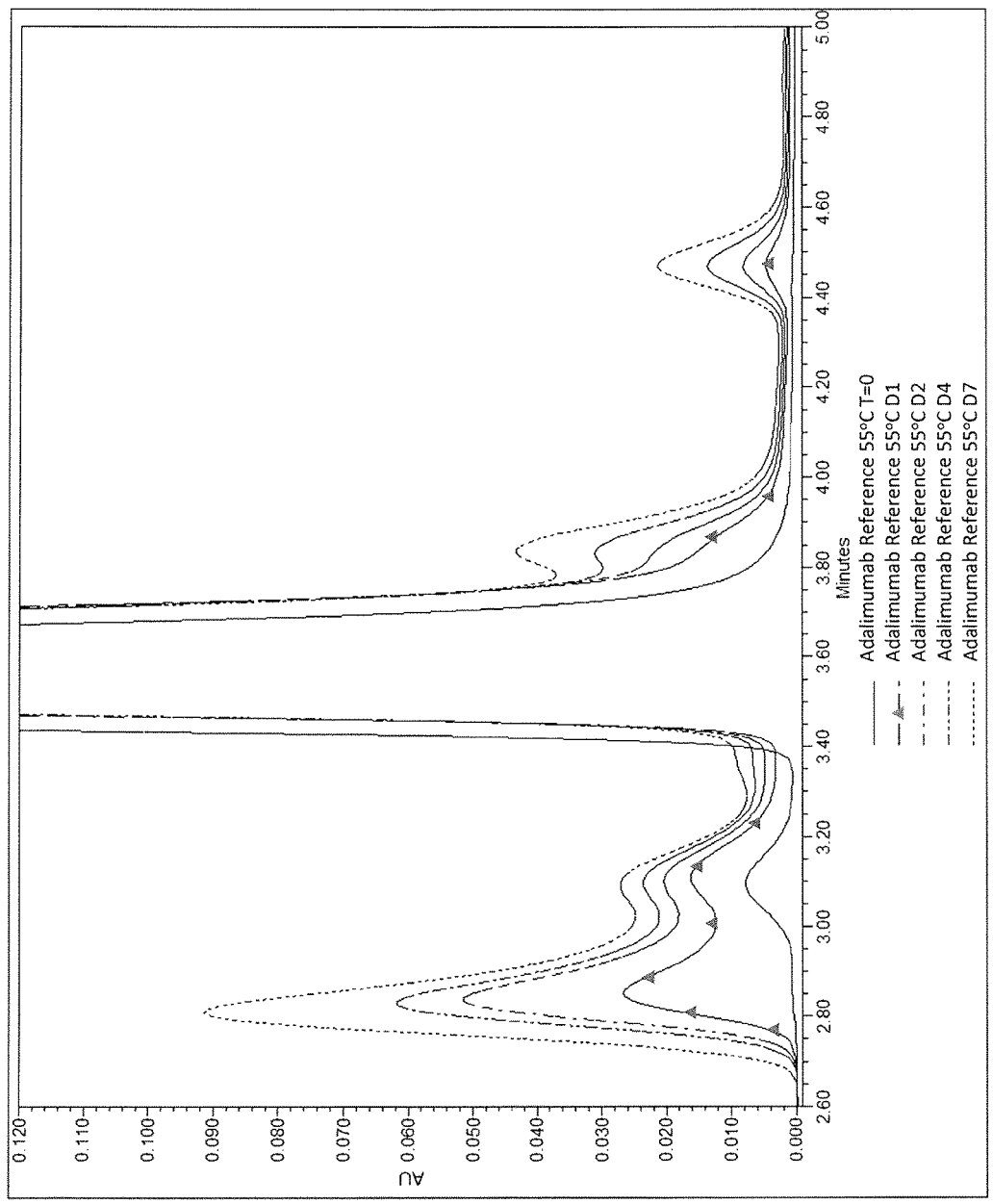
FIG. 10 shows an overlay of SE-UPLC chromatograms for the adalimumab reference formulation under duration of stressed stability experiment (55° C. up to 7 days).

SE-UPLC. Exposure of ONS-3010 to 55° C. generated both higher and lower molecular weight species (HMWS and LMWS) (Table 9), both of which can be monitored by SE-UPLC. From time zero to day 7, there were marked increases in dimer (with a retention time of approximately 3.1 minutes) and species larger-than-dimer with earlier retention times, both counted as HMWS. For fragmentation, a distinct peak was formed off the backside of the monomer peak at ~3.9 minutes, plus an additional peak at 4.5 minutes (FIG. 10). After 7 days of incubation, there were clear differences between the SE-UPLC chromatograms of the formulation conditions (FIG. 11). In particular, the Acetate LS/HM condition illustrated protection toward HMWS formation relative to the adalimumab reference formulation and to the other formulation conditions. This is also displayed in FIG. 12.

TABLE 9

SE-UPLC data for Stressed Stability (55° C.) Day 1 to Day 7

| Sample Name | % Area Total Aggregate | % Monomer Area | % Area Total Degradant |
|---|---|---|---|
| Adalimumab reference 55° C. D1 | 3.81 | 95.78 | 0.42 |
| Acetate 55° C. D1 | 4.18 | 95.48 | 0.34 |
| Acetate LS/HM 55° C. D1 | 2.32 | 97.40 | 0.28 |
| Adalimumab reference 55° C. D2 | 6.31 | 93.11 | 0.58 |
| Acetate 55° C. D2 | 5.42 | 94.00 | 0.58 |
| Acetate LS/HM 55° C. D2 | 2.89 | 96.53 | 0.57 |
| Adalimumab reference 55° C. D4 | 7.75 | 88.93 | 3.32 |
| Acetate 55° C. D4 | 6.92 | 89.94 | 3.13 |
| Acetate LS/HM 55° C. D4 | 4.03 | 93.24 | 2.73 |
| Adalimumab reference 55° C. D7 | 10.75 | 84.20 | 5.05 |
| Acetate 55° C. D7 | 9.81 | 85.43 | 4.76 |
| Acetate LS/HM 55° C. D7 | 6.15 | 89.37 | 4.48 |

Refer to Table 4 for buffer components.
LS/HM: Lower NaCl and higher mannitol levels CEX-HPLC. Cation exchange chromatography of samples treated at 55° C. provides a broad view of many physicochemical changes that can manifest themselves as changes in molecular charge. This includes specific charge based modifications such as deamidation, isomerization, and pyroglutamine formation, but can also reveal more subtle conformational shifts that can begin to occur at elevated temperatures. CEX-HPLC profiles were monitored for time zero through day 2 samples (Table 10).

TABLE 10

CEX data for Stressed Stability (55° C.)

| Sample Description | % Acidic Species | % Main Species | % Basic Species | % Extra Basic Species |
|---|---|---|---|---|
| Adalimumab reference T = 0 2-8° C. | 15.5 | 64.4 | 18.5 | 1.7 |
| Acetate T = 0 2-8° C. | 15.7 | 64.1 | 18.8 | 1.5 |
| Acetate LS/HM T = 0 2-8° C. | 15.5 | 64.0 | 18.6 | 1.8 |
| Adalimumab reference 55° C. Day 1 | 19.6 | 58.5 | 21.0 | 0.9 |
| Acetate 55° C. Day 1 | 19.4 | 58.8 | 20.8 | 1.1 |
| Acetate LS/HM 55° C. Day 1 | 20.4 | 58.1 | 19.6 | 2.0 |
| Adalimumab reference 55° C. Day 2 | 24.9 | 53.7 | 20.8 | 0.6 |
| Acetate 55° C. Day 2 | 24.4 | 54.3 | 20.5 | 0.9 |
| Acetate LS/HM 55° C. Day 2 | 26.2 | 53.5 | 19.4 | 0.9 |

Figure 13:
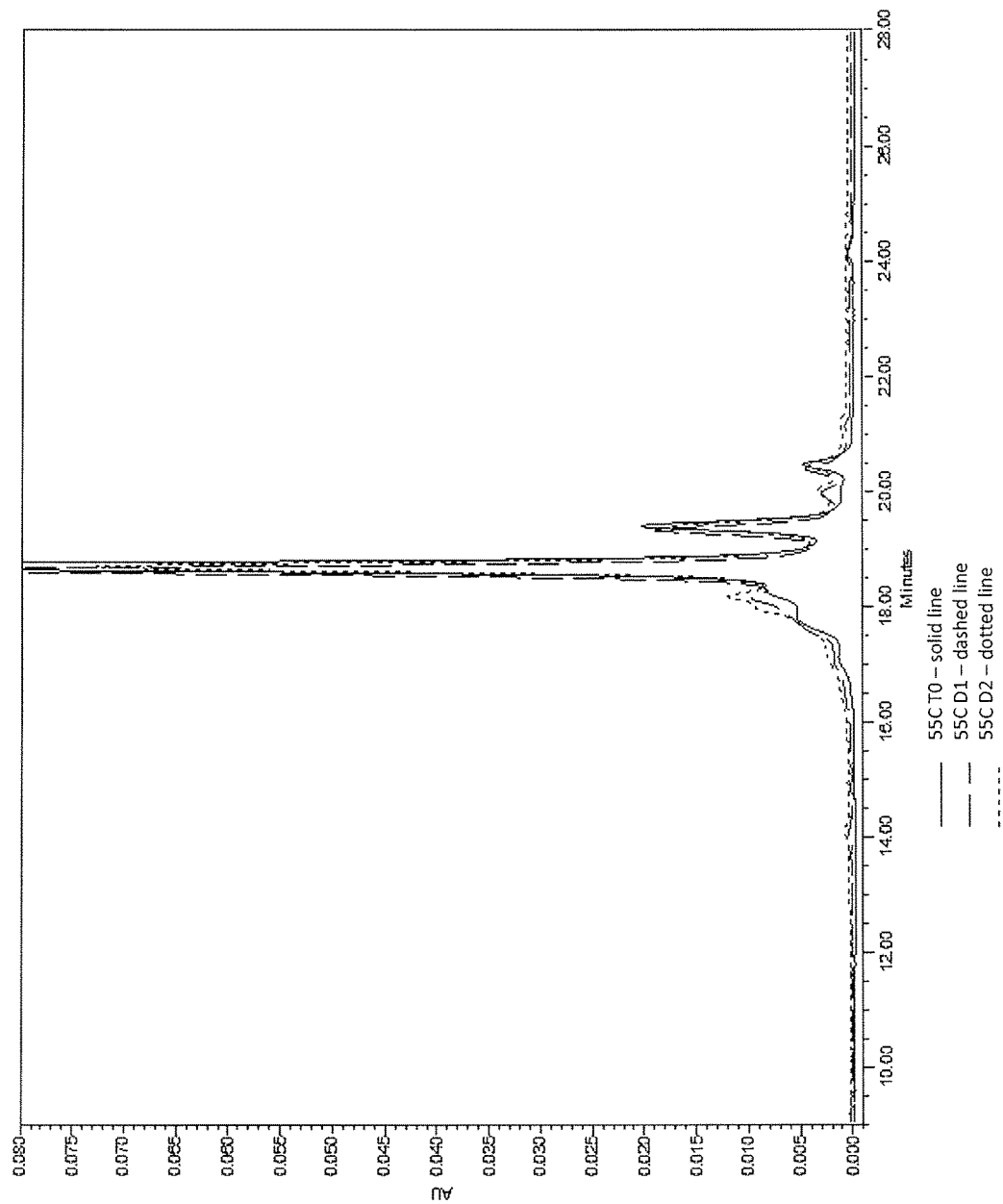
FIG. 13 shows an overlay of CEX-HPLC chromatograms for 55° C.-incubated samples in the adalimumab reference formulation, days 0, 1, and 2.
Figure 14:
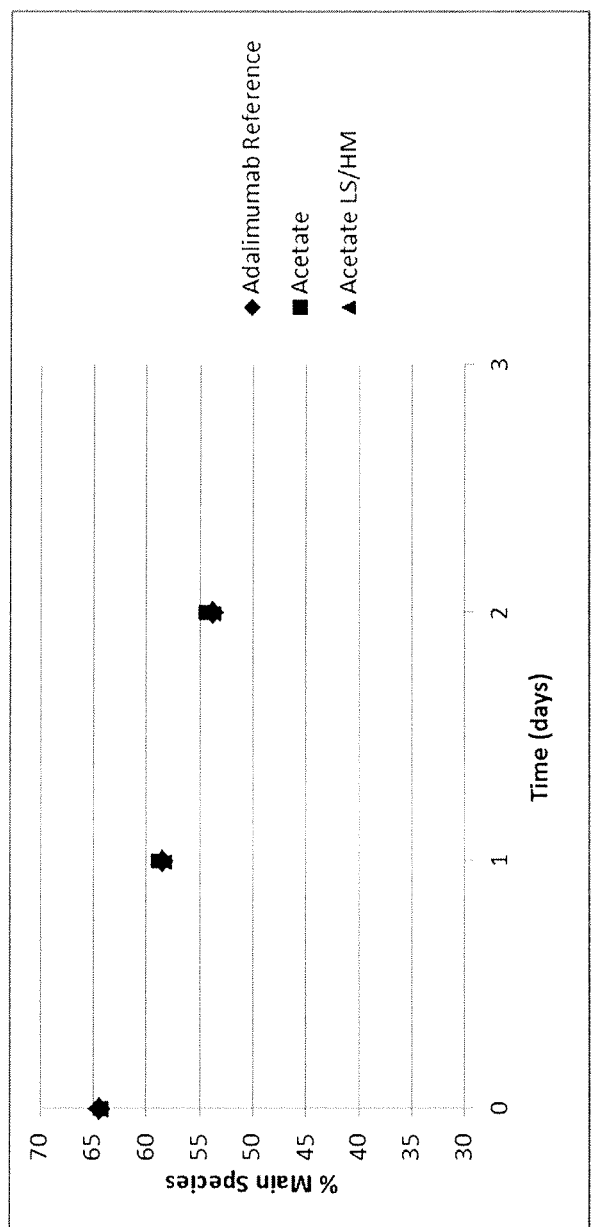
FIG. 14 shows CEX-HPLC Main Peak Percentages for 55° C.-incubated samples up to 2 days.
Figure 15:
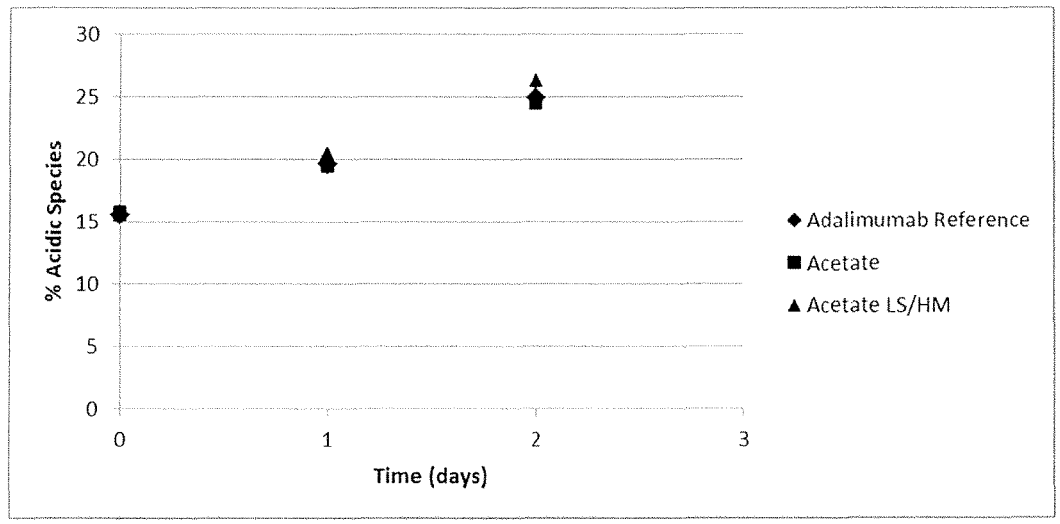
FIG. 15 shows CEX-HPLC Acidic Peak Percentages for 55° C.-incubated samples up to 2 days.
Figure 16:
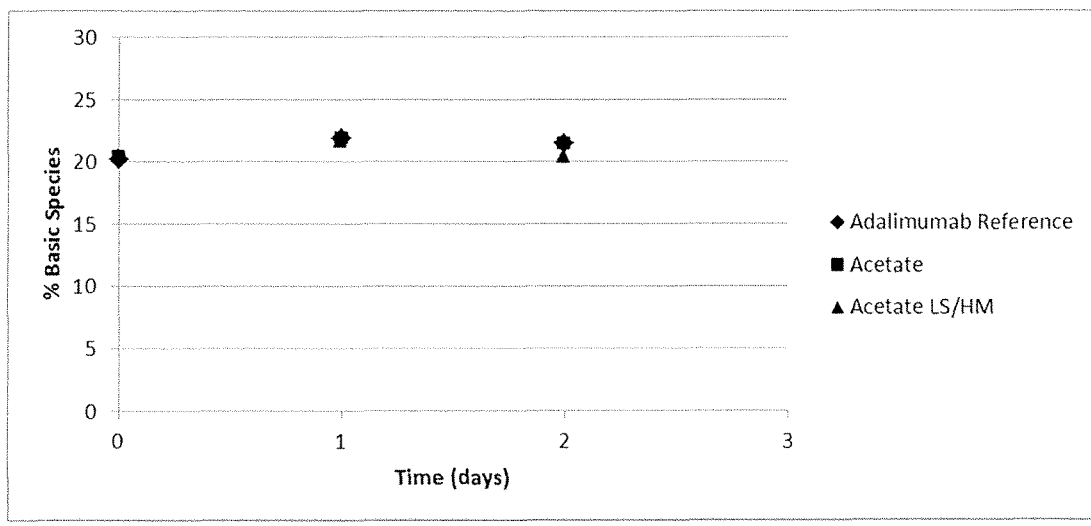
FIG. 16 shows CEX-HPLC Basic Peak Percentages for 55° C.-incubated samples up to 2 days.
Figure 17:
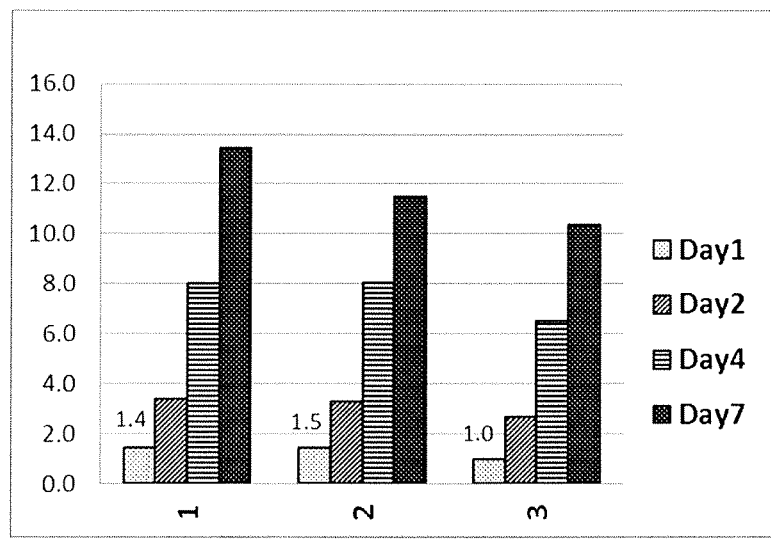
FIG. 17 shows the total percentage of isomerized species in peptide maps of 55° C. stressed ONS-3010 samples (x axis refers to formulation condition number).
Figure 18:
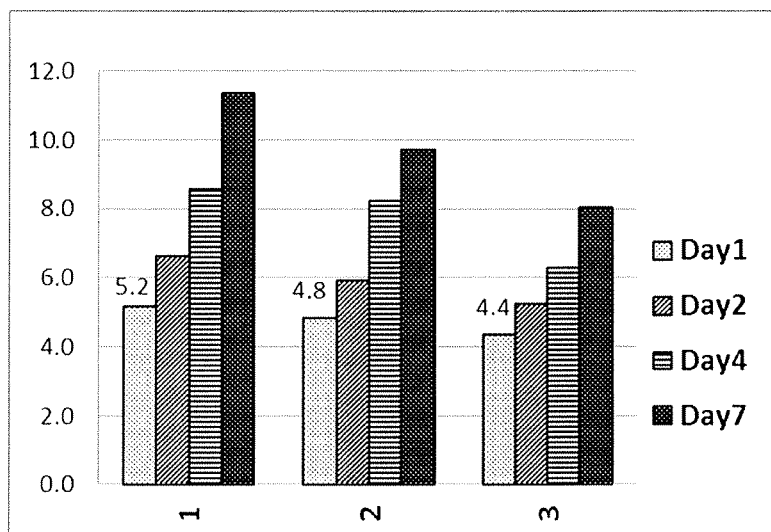
FIG. 18 shows the percentage of cyclized N-terminal peptides in peptide maps of 55° C. stressed ONS-3010 samples (x axis refers to formulation condition number).
Figure 19:
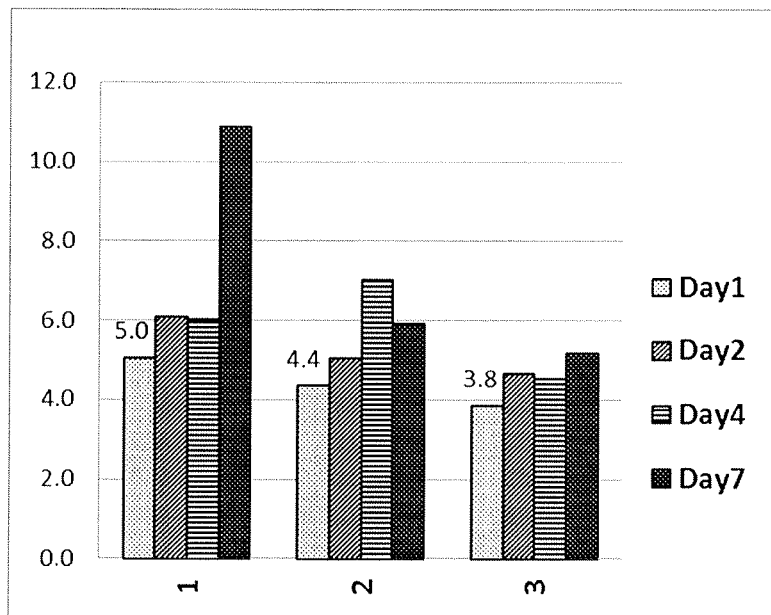
FIG. 19 shows the total percentage of oxidized methionine peptides in peptide maps of 55° C. stressed ONS-3010 samples (x axis refers to formulation condition number).
Figure 20:
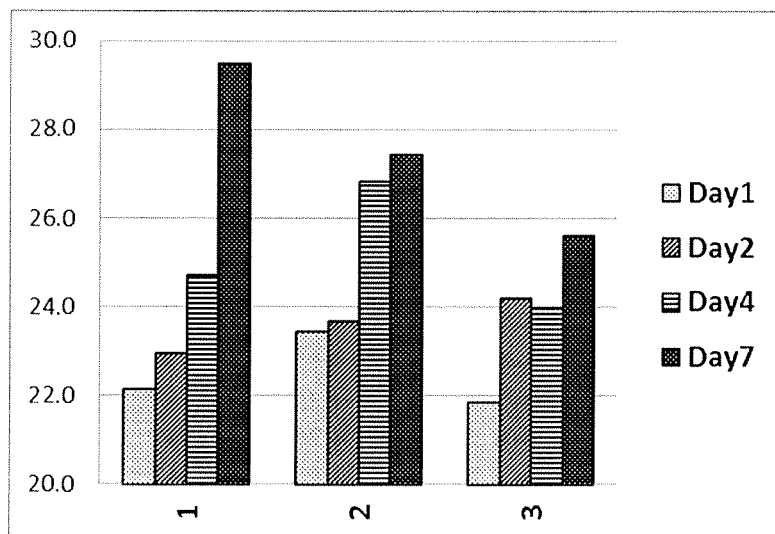
FIG. 20 shows the total percentage of deamidated peptides in peptide maps of 55° C. stressed ONS-3010 samples (x axis refers to formulation condition number).

Refer to Table 4 for buffer components.
LS/HM: Lower NaCl and higher mannitol levels Representative chromatograms for samples in the adalimumab reference formulation are shown in FIG. 13, with an overlay of 55° C. day 2 samples. Trends in CEX % Main, Acidic and Basic species are shown in FIG. 14, FIG. 15, and FIG. 16. The acetate LS/HM buffer formulation had a similar CEX profile to that of the adalimumab reference formulation after treatment at 55 degrees C. for two days. Minor differences are within assay variability.

CE-SDS R/NR. To provide an orthogonal view of size variants (denatured vs. the non-denatured SE-UPLC methodology), CE-SDS was used under both non-reducing and reducing conditions. The strong differentiation between formulation conditions observed with SE-UPLC is not seen under analysis by denaturing techniques, indicating that the size variants formed are largely noncovalent in nature.

Bioassay. In general, all samples tested showed comparable relative potency in the bioassay within method variability. There was no measurable change in potency after the 7 day treatment at 55 degrees C., demonstrating stability toward thermal denaturation.

Peptide Map. Peptide mapping allowed a more specific view of modifications in ONS-3010. The 55° C. incubation temperature fostered certain chemical modifications that are not commonly observed at lower temperatures, such as pyroglutamic acid formation of the N-terminal heavy chain and specific isomerization events. Condition 3 (Acetate LS/HM) appeared to have the most protection against this assortment of chemical modifications (FIG. 17, FIG. 18, FIG. 19, FIG. 20, and Table 11). The oxidation of methionine 256 in the CH2 domain in condition 3 day 7 stressed sample, for example, was kept to a level within the unstressed range. C-terminal variants and glycosylation levels remained constant throughout the treatment.

TABLE 11

Selected ONS-3010 post-translational modifications monitored by peptide mapping in stressed stability samples

| | | Unstressed | ONS-3010 day 7 55° C. | | |
| --- | --- | --- | --- | --- | --- |
| Modification | Site | Adalimumab Range (%) | Adalimumab reference | Acetate | Acetate LS/HM |
| N-terminal Pyro-E | N-term | <1.7 | 11.4 | 9.7 | 8.1 |
| Oxidation | HC M256 | 1.5-2.4 | 5.0 | 2.6 | 2.3 |
| Oxidation | HC M432 | <0.7 | 5.0 | 2.9 | 2.5 |
| Deamidation | LC N137/138 | 2.2-3.5 | 2.2 | 1.8 | 1.6 |
| Deamidation | LC N152/158 | 0.6-1.5 | 0.0 | 0.0 | 0.0 |
| Deamidation | HC N54 | 0.4-2.4 | 1.1 | 1.0 | 0.9 |
| Deamidation | HC N77/N84 | 0.2-1.3 | 1.0 | 0.9 | 0.8 |
| Deamidation | HC N280/290 | 0.1-1.9 | 0.6 | 0.5 | 0.4 |
| Deamidation mods | HC N319 | 3.9-11.2 | 6.1 | 5.3 | 4.8 |
| Deamidation mods | PENNY peptide HC N388/393/394 | 12.2-19.4 | 15.3 | 14.8 | 14.0 |
| Deamidation | HC N438 | 0.2-1.6 | 1.2 | 1.0 | 0.9 |
| Isomerization | HC D30 | <LOQ | 2.9 | 2.9 | 3.1 |
| Isomerization | HC D62 | <LOQ | 1.5 | 1.3 | 1.4 |
| Isomerization | HC D284 | <LOQ | 9.0 | 7.3 | 5.8 |

Refer to Table 4 for buffer components.
LS/HM: Lower NaCl and higher mannitol levels Accelerated Stability (37° C. and 25° C.). Accelerated (37° C. and 25° C.) and real-time stability studies were conducted in glass vials. Samples were pulled for analysis by SE-UPLC, CEX-HPLC, CE-SDS, Appearance, Bioassay, and peptide mapping (at selected timepoints). At 25° C. up to 28 days, acetate formulations were comparable to adalimumab reference formulations for CEX-HPLC, SE-UPLC, CE-SDS, peptide map and Bioassay.

Figure 21:
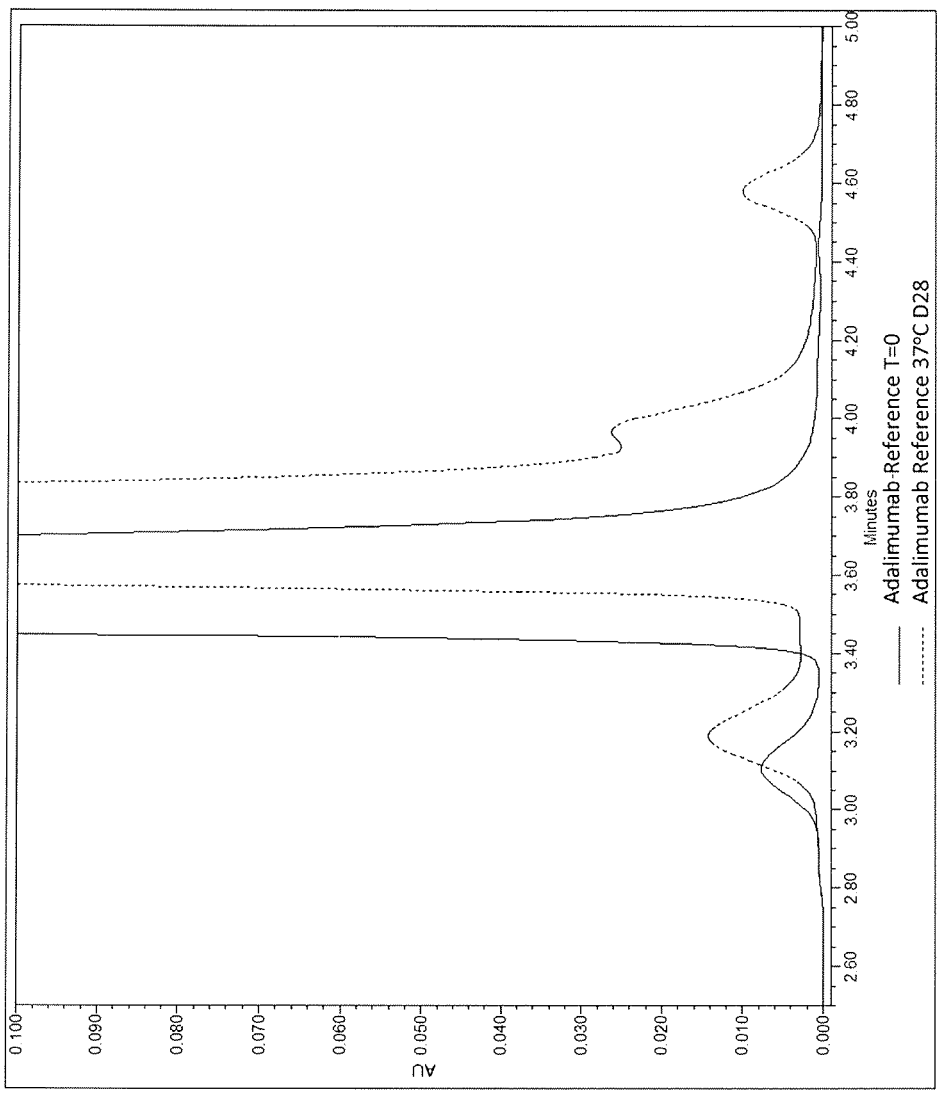
FIG. 21 shows an overlay of SE-UPLC chromatograms for adalimumab reference formulation samples incubated at 37° C., time zero and day 28.
Figure 22:
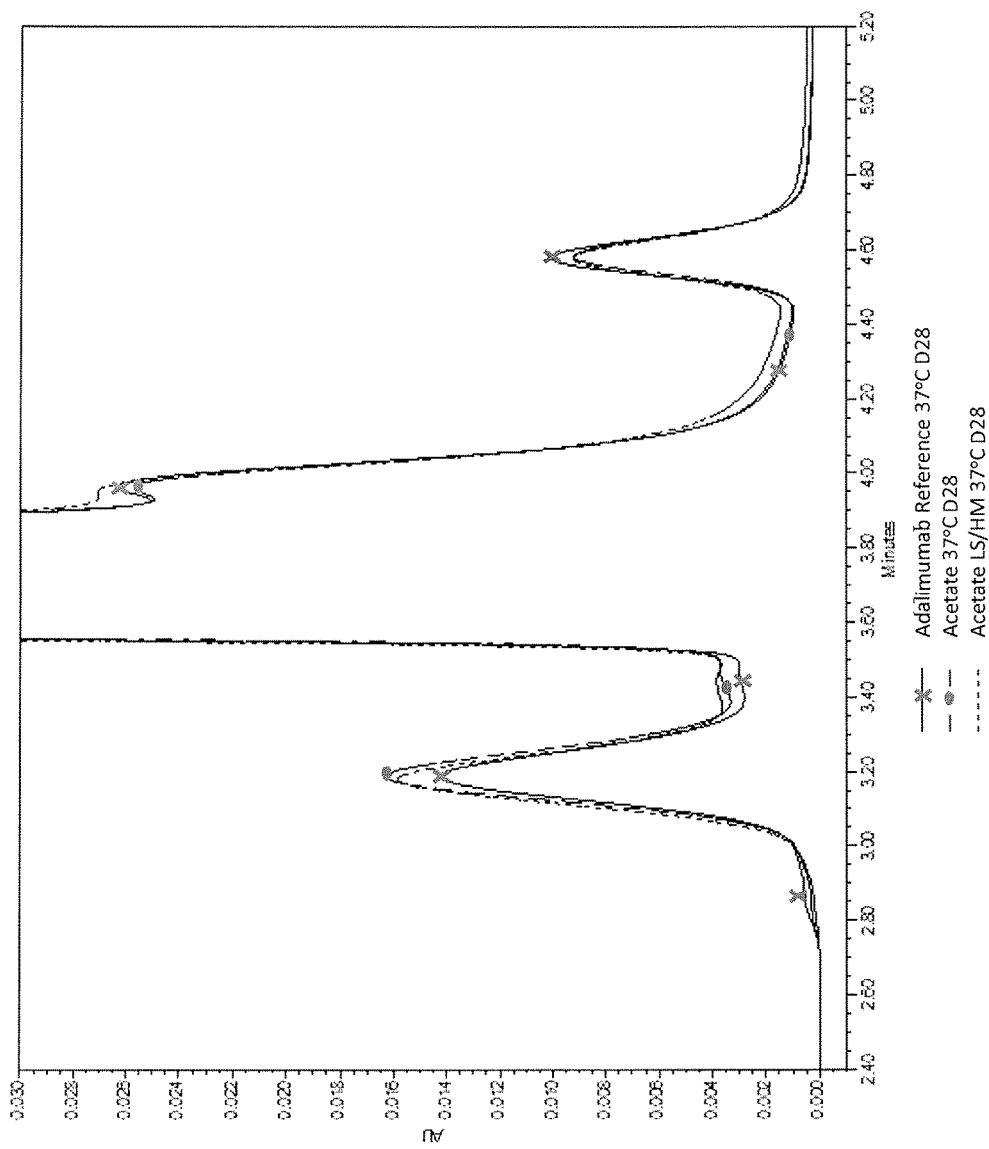
FIG. 22 shows an overlay of SE-UPLC chromatograms for 37° C.-incubated day 28 samples.

SE-UPLC. An overlay of 37° C. incubated chromatograms for the adalimumab reference formulation is shown in FIG. 21, with a zoomed overlay of all three conditions at day 28 in FIG. 22. All three conditions have similar SE-UPLC profiles after 28 days at 37° C., with main peak/monomer purity levels ~96%. The formation of a back shoulder on the monomer peak (4 minutes retention time) is observed in all formulation conditions, and was at the integration threshold for some earlier time points (leading to some variation in quantitating LMWS, see Table 12 for numerical values, noting the punctuated increase between day 21 and 28).

TABLE 12

SE-UPLC for 37° C. accelerated stability samples

| 37° C. | % HMWS | | | | % Monomer | | | | % LMWS | | | |
| --- | --- | --- | --- | --- | --- | --- | --- | --- | --- | --- | --- | --- |
| Sample | T0 | 14 d | 21 d | 28 d | T0 | 14 d | 21 d | 28 d | T0 | 14 d | 21 d | 28 d |
| Adalimumab reference | 0.74 | 1.25 | 1.36 | 1.52 | 99.16 | 98.34 | 98.08 | 95.9 | 0.10 | 0.40 | 0.57 | 2.58 |
| Acetate | 0.71 | 1.27 | 1.43 | 1.74 | 99.14 | 98.31 | 98.07 | 95.84 | 0.15 | 0.42 | 0.49 | 2.42 |
| Acetate LS/HM | 0.7 | 1.04 | 1.24 | 1.71 | 99.16 | 98.62 | 98.29 | 95.77 | 0.14 | 0.34 | 0.47 | 2.52 |

Refer to Table 4 for buffer components.
LS/HM: Lower NaCl and higher mannitol levels CEX-HPLC. CEX-HPLC analysis of accelerated stability samples at 14 day, 21 day and 28 days of treatment at 37° C. (Table 13) showed acetate conditions comparable to the adalimumab reference formulation.

TABLE 13

CEX-HPLC data for Stressed Stability (37° C.)

| Sample Description | % Acidic Species | % Main Species | % Basic Species | % Extra Basic Species |
|---|---|---|---|---|
| Adalimumab Reference 37° C. Day 14 | 22.4 | 56.4 | 19.9 | 1.4 |
| Acetate 37° C. Day 14 | 21.8 | 57.5 | 19.5 | 1.1 |
| Acetate LS/HM 37° C. Day 14 | 22.3 | 57.4 | 19.5 | 0.8 |
| Adalimumab Reference 37° C. Day 21 | 25.7 | 53.3 | 20.2 | 0.9 |
| Acetate 37° C. Day 21 | 24.3 | 54.3 | 20.2 | 1.2 |
| Acetate LS/HM 37° C. Day 21 | 26.2 | 52.7 | 19.6 | 1.5 |
| Adalimumab Reference 37° C. Day 28 | 29.0 | 49.7 | 20.1 | 1.1 |
| Acetate 37° C. Day 28 | 27.5 | 50.9 | 20.1 | 1.5 |
| Acetate LS/HM 37° C. Day 28 | 30.4 | 49.0 | 19.3 | 1.3 |

Refer to Table 4 for buffer components.
LS/HM: Lower NaCl and higher mannitol levels CE-SDS (R/NR). For the 37° C. incubated samples, CE-SDS testing reveals similar trends in NR denatured size variants between the three conditions after 28 days. For 37° C. R CE-SDS, all conditions relative to the adalimumab reference formulation are comparable after 28 days.

Bioassay. All formulation conditions displayed full potency in the L929 bioassay after 28 days incubation at 37° C.

Appearance. Regular visual inspection was conducted for the accelerated and real-time stability samples. Specifically, the samples were monitored for any change in color, clarity, and the presence of particles, proteinaceous or not. In general, the ONS-3010 samples displayed visual appearance as desired for a protein product. In 37° C. incubated samples, all formulations except condition 3 displayed some particle formation by day 20, while condition 3 (acetate LS/HM) remained free from particles at day 28 (Table 14). All formulations showed some visible particles at 26 days at 2-8° C. (Table 30).

TABLE 14

Appearance data for Stressed Stability (37° C.)

| Day | Adalimumab Reference | Acetate | Acetate LS/HM |
|---|---|---|---|
| 0 | C | C | C |
| 1 | C | C | C |
| 4 | C | C | C |
| 5 | C | C | C |
| 6 | C | C | C |
| 7 | C | C | C |
| 8 | C | C | C |
| 11 | C | C | C |
| 12 | C | C | C |
| 13 | C | C | C |
| 14 | C | C | C |
| 15 | C | C | C |
| 18 | C | C | C |
| 19 | C | C | C |
| 20 | 1P | C | C |
| 21 | 1P | 1P | C |
| 22 | 1P | 1P | C |
| 25 | 1P | 1P | C |
| 26 | 1P | 1P | C |
| 27 | 1P | 1P | C |
| 28 | 1P | 1P | C |

C = Clear,
1P to 5P scale: 1P = particle visible, 5P = many particles visible
Refer to Table 4 for buffer components.
LS/HM: Lower NaCl and higher mannitol levels Forced Oxidation. A forced oxidation study utilized 1% t-butyl hydrogen peroxide treatment to induce oxidation in ONS-3010 formulation candidates. SE-UPLC, CEX-HPLC, and tryptic peptide map methodologies were used to monitor changes in product quality attributes and specific amino acid residues that are susceptible to oxidation. Oxidative modification is one of the major chemical degradation pathways. Sites of oxidation damage on backbone or side-chain can change hydrophobicity of protein surfaces. The fingerprint of oxidation by using LC-MS peptide mapping enables a fast and reliable approach for formulation selection.

There were five methionine residues distributed along the sequence of ONS-3010: at residue M4 in the light chain, and residues M34, M83, M256, and M432 in the heavy chain. M34 is within the CDR.

Figure 23:
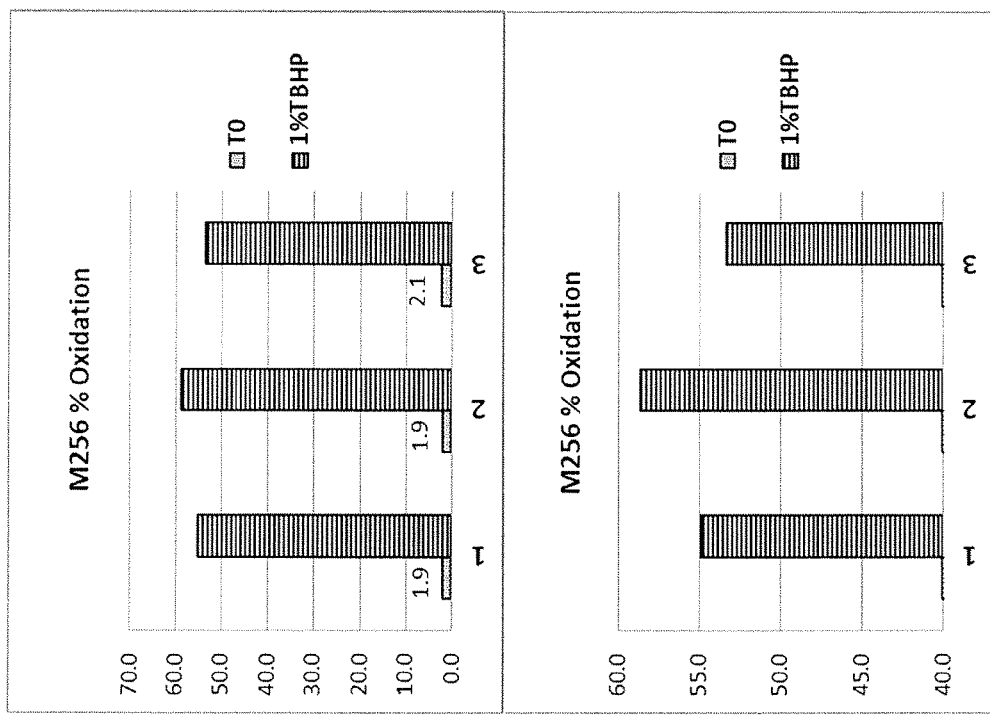
FIG. 23 shows the percentage of oxidized methionine-256 peptides in ONS-3010 forced oxidation study peptide maps (x axis refers to formulation condition number). Top=full view, bottom=zoomed.
Figure 24:
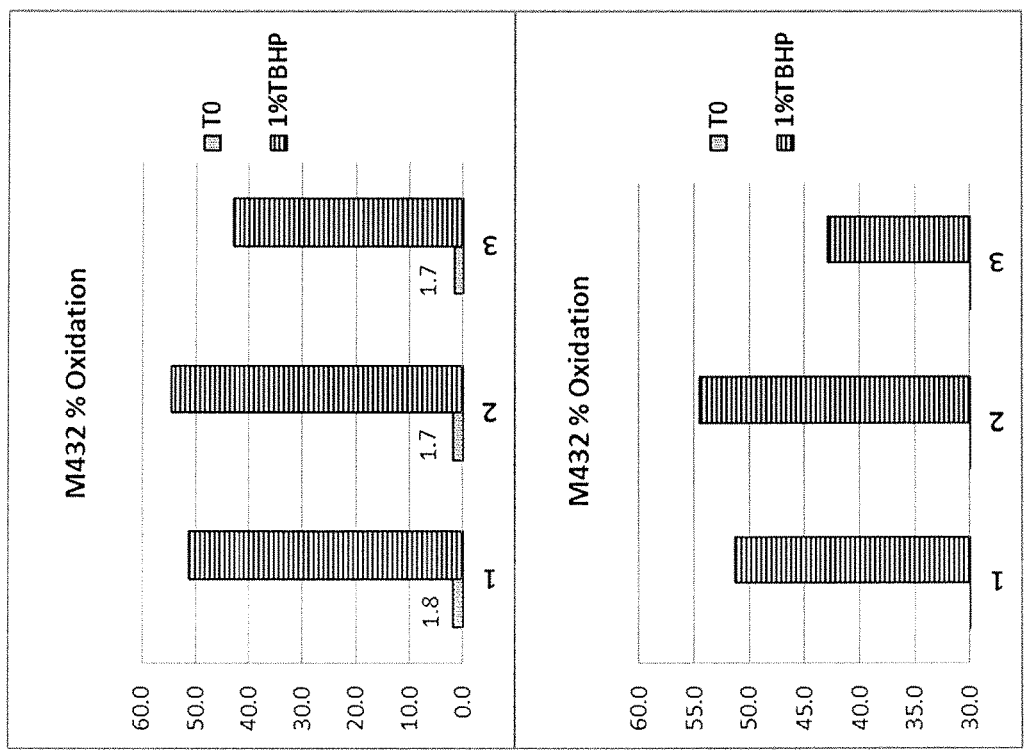
FIG. 24 shows the percentage of oxidized methionine-432 peptides in ONS-3010 forced oxidation study peptide maps (x axis refers to formulation condition number). Top=full view, bottom=zoomed.
Figure 25:
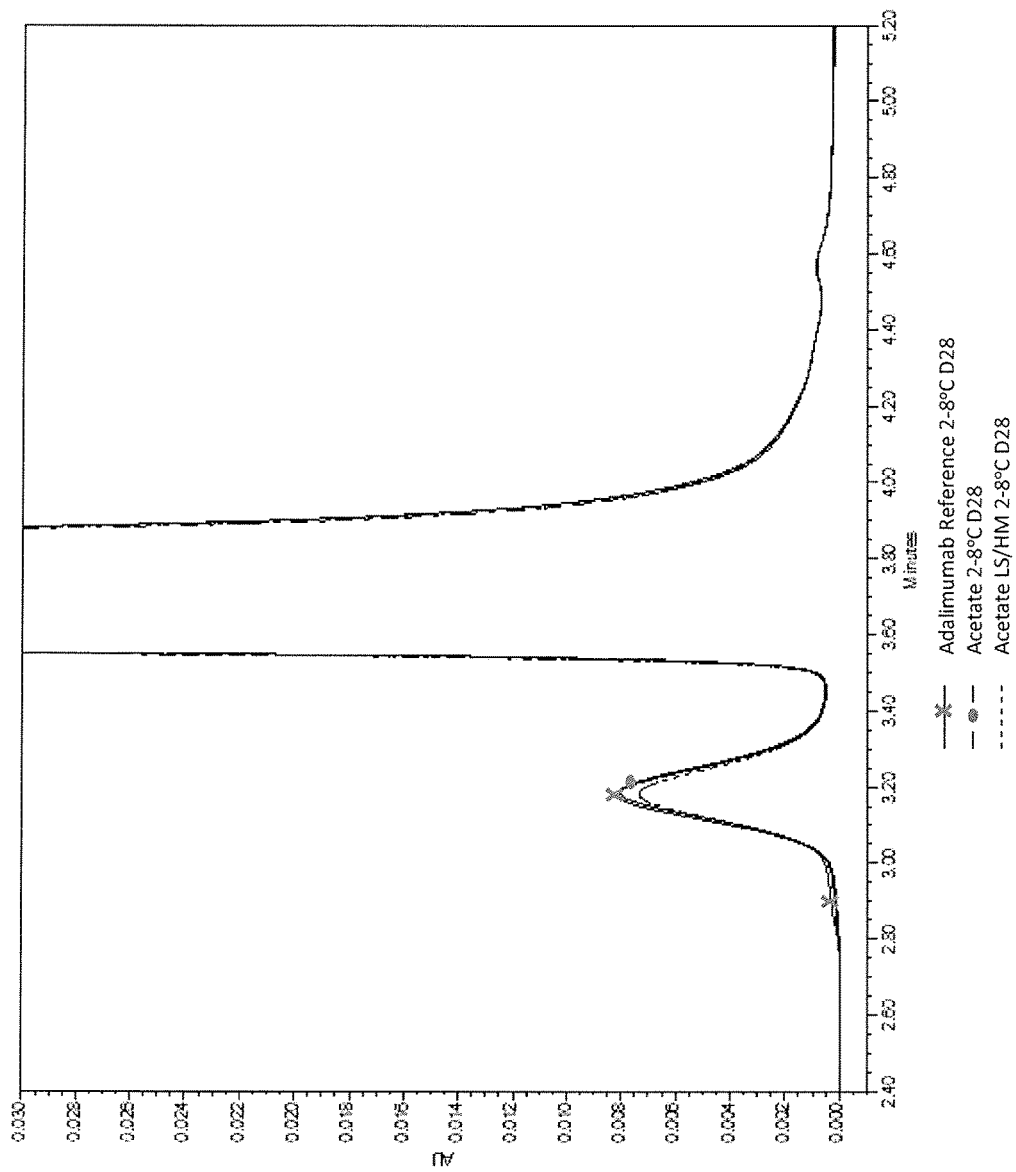
FIG. 25 shows an overlay of SE-UPLC chromatograms for 2-8° C.-incubated day 28 samples.
Figure 26:
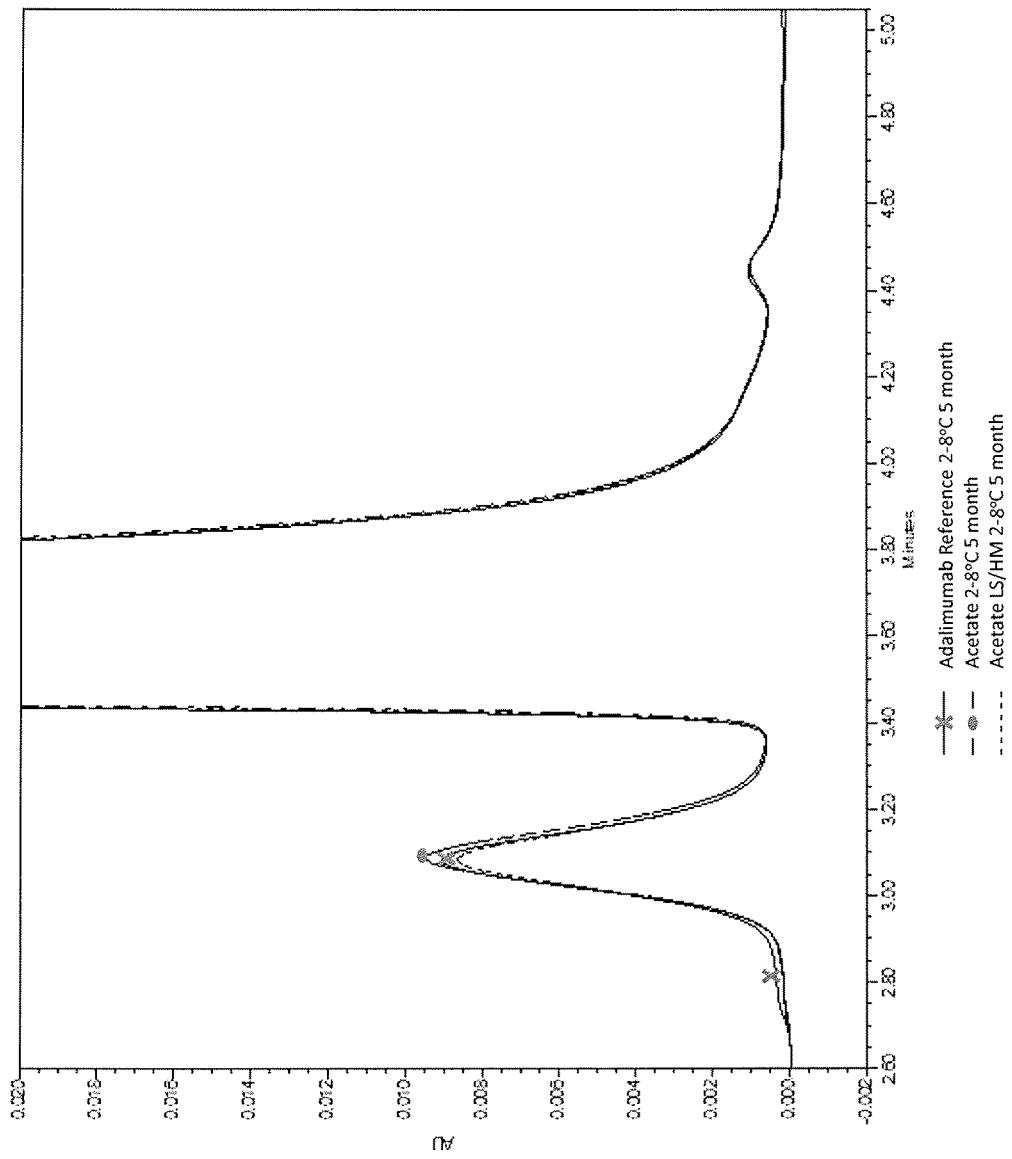
FIG. 26 shows an overlay of SE-UPLC chromatograms for 2-8° C.-incubated 5 month samples.
Figure 27:
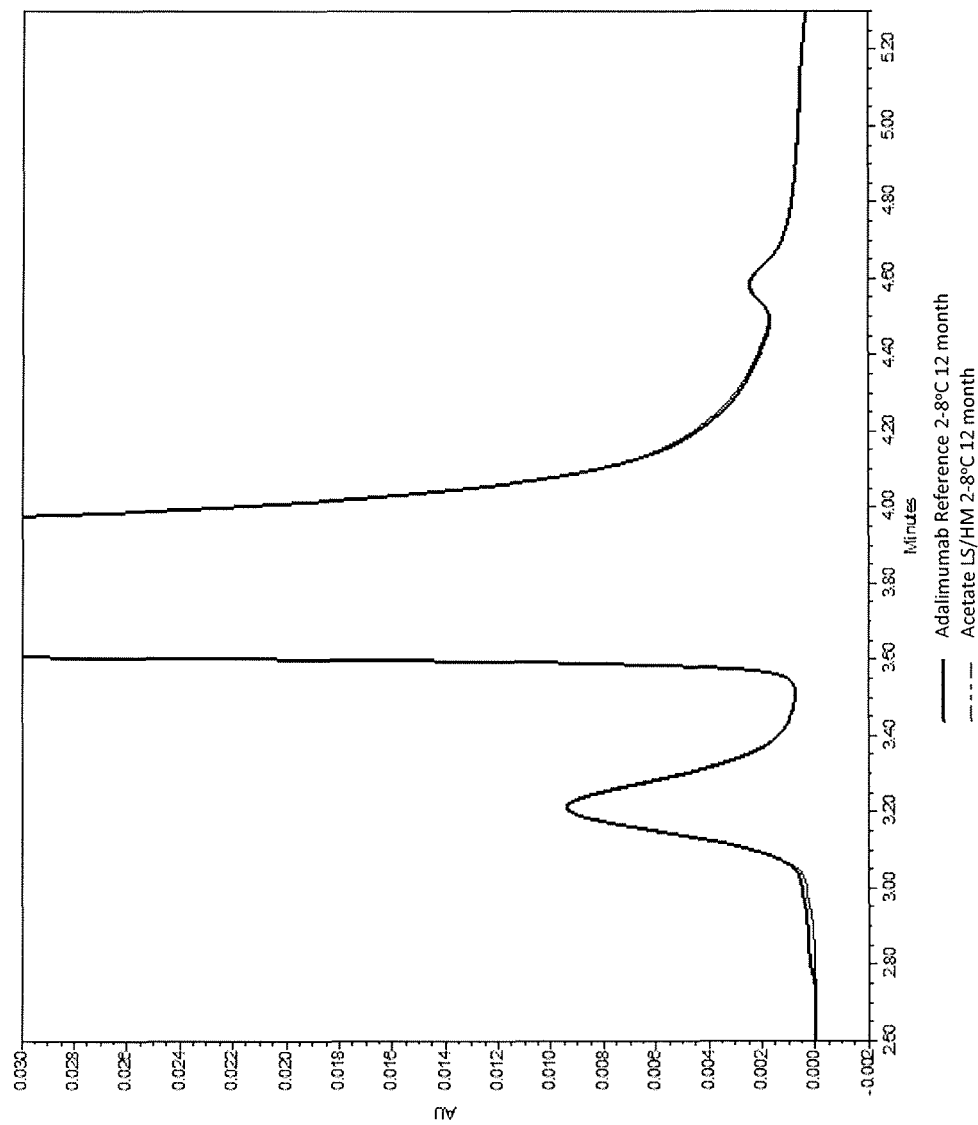
FIG. 27 shows an overlay of SE-UPLC chromatograms for 2-8° C.-incubated 12 month samples, conditions 1 and 3.
Figure 28:
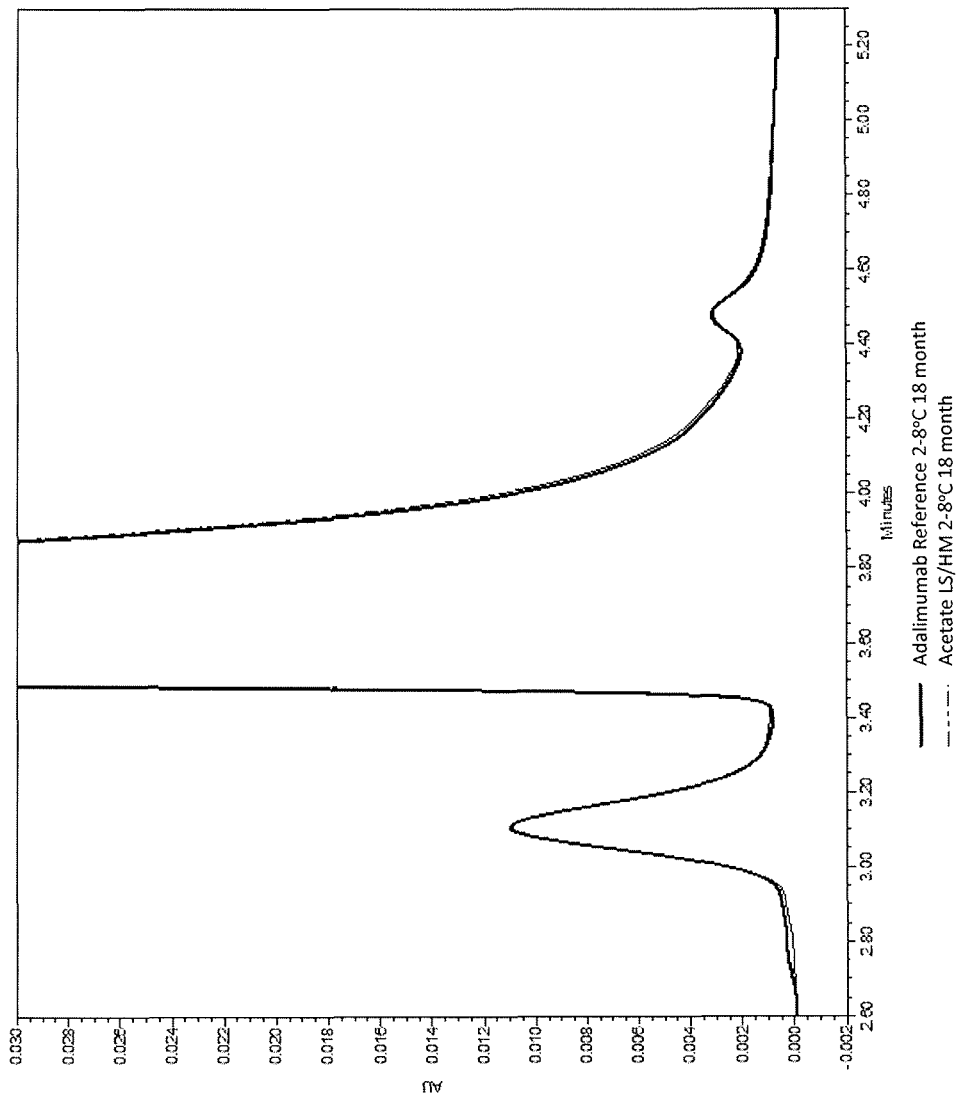
FIG. 28 shows an overlay of SE-UPLC chromatograms for 2-8° C.-incubated 18 month samples, conditions 1 and 3.

Based on the peptide mapping data, the Fc region methionine residues M256 and M432 were the dominant residues modified by oxidation (FIG. 23 and FIG. 24). Formulation condition #3 provided the most protection overall to oxidation. Oxidized species of residues M4 and M83 were below the method LOQ even in stressed conditions. Upon stress, oxidized M34 was at the LOQ, with the three conditions comparable within method variability.

For CEX-HPLC, the oxidative stress treatment results in a decrease in main peak and a corresponding increase in basic peak percentages of several percent (Table 15). Condition 3 (Acetate LS/HM) appeared more protective to the oxidation than the other conditions. SE-UPLC values are essentially unchanged upon treatment.

TABLE 15

CEX-HPLC data for Forced Oxidation 37° C.

| Sample Description | % Acidic Species | % Main Species | % Basic Species | % Extra Basic Species |
|---|---|---|---|---|
| Adalimumab Reference T = 0 2-8° C. | 15.3 | 65.2 | 18.6 | 0.8 |
| Acetate T = 0 2-8° C. | 15.1 | 65.4 | 18.7 | 0.8 |
| Acetate LS/HM T = 0 2-8° C. | 15.5 | 65.1 | 18.6 | 0.8 |

TABLE 15-continued

CEX-HPLC data for Forced Oxidation 37° C.

| Sample Description | % Acidic Species | % Main Species | % Basic Species | % Extra Basic Species |
|---|---|---|---|---|
| Adalimumab Reference 1% TBHP | 14.0 | 63.4 | 20.9 | 1.7 |
| Acetate 1% TBHP | 14.2 | 64.1 | 20.5 | 1.3 |

TABLE 15-continued

CEX-HPLC data for Forced Oxidation 37° C.

| Sample Description | % Acidic Species | % Main Species | % Basic Species | % Extra Basic Species |
|---|---|---|---|---|
| Acetate LS/HM 1% TBHP | 14.6 | 64.6 | 19.9 | 0.9 |

Refer to Table 4 for buffer components.
LS/HM: Lower NaCl and higher mannitol levels Freeze-Thaw Cycling. Freeze-thaw cycling was conducted for samples in the candidate formulations at two temperatures: −20° C. and −80° C. Samples were placed in freezers set to the appropriate temperature and allowed to freeze thoroughly (for at least one hour). Samples were then removed from the freezer and allowed to thaw at 25° C. (approximately 1 hour). This freezing step plus the thawing step constituted a single cycle. Samples were subjected to up to 5 freeze-thaw cycles, and then analyzed together by SE-UPLC, with a subset of samples also tested by NR CE-SDS.

All formulation conditions appeared to be stable to multiple freeze-thaw cycles at −80° C., with main peak purity values after five cycles equivalent to time zero values. With −20° C. cycling, some increases in % HMWS were observed, more prevalent in the higher mannitol formulation condition 3 (Table 16). It is believed that this may be indicative of mannitol crystallization fostered at this lower frozen temperature. The adalimumab reference formulation and condition 3 exhibited similar patterns upon cycling as monitored by NR CE-SDS.

TABLE 16

SE-UPLC data for Freeze/Thaw ("C" = freeze/thaw cycle 1-5)

| Sample Name | % Area Total Aggregate | % Monomer Area | % Area Total Degradant |
|---|---|---|---|
| Adalimumab Reference F/T C1 25/−20° C. | 0.71 | 99.21 | 0.07 |
| Acetate F/T C1 25/−20° C. | 0.68 | 99.28 | 0.04 |
| Acetate LS/HM F/T C1 25/−20° C. | 0.66 | 99.22 | 0.13 |
| Adalimumab Reference F/T C1 25/−80° C. | 0.72 | 99.18 | 0.09 |
| Acetate F/T C1 25/−80° C. | 0.69 | 99.25 | 0.05 |
| Acetate LS/HM F/T C1 25/−80° C. | 0.65 | 99.28 | 0.07 |
| Adalimumab Reference F/T C2 25/−20° C. | 0.71 | 99.22 | 0.07 |
| Acetate F/T C2 25/−20° C. | 0.71 | 99.14 | 0.14 |
| Acetate LS/HM F/T C2 25/−20° C. | 1.42 | 98.44 | 0.14 |
| Adalimumab Reference F/T C2 25/−80° C. | 0.73 | 99.16 | 0.1 |
| Acetate F/T C2 25/−80° C. | 0.70 | 99.18 | 0.12 |
| Acetate LS/HM F/T C2 25/−80° C. | 0.66 | 99.20 | 0.14 |
| Adalimumab Reference F/T C3 25/−20° C. | 0.73 | 99.15 | 0.1 |
| Acetate F/T C3 25/−20° C. | 0.72 | 99.13 | 0.15 |
| Acetate LS/HM F/T C3 25/−20° C. | 1.40 | 98.48 | 0.12 |
| Adalimumab Reference F/T C3 25/−80° C. | 0.73 | 99.15 | 0.13 |
| Acetate F/T C3 25/−80° C. | 0.70 | 99.15 | 0.14 |
| Acetate LS/HM F/T C3 25/−80° C. | 0.65 | 99.26 | 0.09 |
| Adalimumab Reference F/T C4 25/−20° C. | 0.73 | 99.17 | 0.11 |
| Acetate F/T C4 25/−20° C. | 0.71 | 99.14 | 0.14 |
| Acetate LS/HM F/T C4 25/−20° C. | 1.37 | 98.56 | 0.06 |
| Adalimumab Reference F/T C4 25/−80° C. | 0.73 | 99.14 | 0.12 |
| Acetate F/T C4 25/−80° C. | 0.69 | 99.24 | 0.07 |
| Acetate LS/HM F/T C4 25/−80° C. | 0.65 | 99.21 | 0.14 |
| Adalimumab Reference F/T C5 25/−20° C. | 0.72 | 99.17 | 0.11 |
| Acetate F/T C5 25/−20° C. | 0.70 | 99.15 | 0.14 |
| Acetate LS/HM F/T C5 25/−20° C. | 1.37 | 98.57 | 0.06 |
| Adalimumab Reference F/T C5 25/−80° C. | 0.72 | 99.16 | 0.12 |
| Acetate F/T C5 25/−80° C. | 0.70 | 99.15 | 0.15 |
| Acetate LS/HM F/T C5 25/−80° C. | 0.64 | 99.24 | 0.12 |

Refer to Table 4 for buffer components.
LS/HM: Lower NaCl and higher mannitol levels Shaking Studies. In order to assess the protective ability of the formulation toward shear forces, a shaking study was conducted in glass vials (0.5 mL fills) placed in an orbital shaking incubator set to 150 rpm at 37° C. A second arm contained formulations without the addition of polysorbate 80. Samples were tested with the following methods: SE-UPLC, CEX-HPLC, CE-SDS (R/NR), L929 BioAssay, Peptide Map, and Appearance.

For both shaking studies with and without polysorbate 80, based on SE-UPLC, conditions 2 and 3 (with main peak purities ~96% at day 28) were comparable or slightly better to the adalimumab reference formulation (Tables 17-24). CEX-HPLC results showed no significant difference in the acetate formulations compared to the adalimumab reference formulation (Tables 25-27). Day 28 samples displayed full potency in the L929 bioassay, and CE-SDS (R/NR) values are similar across conditions. At day 28, all conditions showed some visible particulate formation: condition 3 showed more protection than the other conditions (Tables 28 and 29).

TABLE 17

SE-UPLC data for Shaking Study with Polysorbate 80 - Day 7

| Sample Name | % Area Total Aggregate | % Monomer Area | % Area Total Degradant |
|---|---|---|---|
| Adalimumab Reference Shaking D7 | 1.02 | 98.71 | 0.26 |
| Acetate Shaking D7 | 1.08 | 98.65 | 0.26 |
| Acetate LS/HM Shaking D7 | 0.92 | 98.78 | 0.3 |

Refer to Table 4 for buffer components.
LS/HM: Lower NaCl and higher mannitol levels

TABLE 18

SE-UPLC data for Shaking Study with Polysorbate 80 - Day 14

| Sample Name | % Area Total Aggregate | % Monomer Area | % Area Total Degradant |
|---|---|---|---|
| Adalimumab Reference Shaking D14 | 1.21 | 98.36 | 0.42 |
| Acetate Shaking D14 | 1.30 | 98.30 | 0.40 |
| Acetate LS/HM Shaking D14 | 1.09 | 98.56 | 0.34 |

Refer to Table 4 for buffer components.
LS/HM: Lower NaCl and higher mannitol levels

TABLE 19

SE-UPLC data for Shaking Study with Polysorbate 80 - Day 21

| Sample Name | % Area Total Aggregate | % Monomer Area | % Area Total Degradant |
|---|---|---|---|
| Adalimumab Reference Shaking D21 | 1.30 | 96.75 | 1.96 |
| Acetate Shaking D21 | 1.47 | 98.05 | 0.49 |
| Acetate LS/HM Shaking D21 | 1.36 | 98.16 | 0.48 |

Refer to Table 4 for buffer components.
LS/HM: Lower NaCl and higher mannitol levels

TABLE 20

SE-UPLC data for Shaking Study with Polysorbate 80 - Day 28

| Sample Name | % Area Total Aggregate | % Monomer Area | % Area Total Degradant |
|---|---|---|---|
| Adalimumab Reference Shaking D28 | 1.51 | 95.94 | 2.56 |
| Acetate Shaking D28 | 1.78 | 95.81 | 2.41 |
| Acetate LS/HM Shaking D28 | 1.58 | 96.07 | 2.35 |

Refer to Table 4 for buffer components.
LS/HM: Lower NaCl and higher mannitol levels

TABLE 21

SE-UPLC data for Shaking Study without Polysorbate 80 - Day 6 without Polysorbate 80 (Tw)

| Sample Name | % Area Total Aggregate | % Monomer Area | % Area Total Degradant |
|---|---|---|---|
| Adalimumab Reference Shaking w/o Tw D6 | 0.97 | 98.77 | 0.25 |
| Acetate Shaking w/o Tw D6 | 0.99 | 98.80 | 0.20 |
| Acetate LS/HM Shaking w/o Tw D6 | 0.86 | 98.94 | 0.20 |

Refer to Table 4 for buffer components.
LS/HM: Lower NaCl and higher mannitol levels

TABLE 22

SE-UPLC data for Shaking Study without Polysorbate 80 (Tw) - Day 13

| Sample Name | % Area Total Aggregate | % Monomer Area | % Area Total Degradant |
|---|---|---|---|
| Adalimumab Reference Shaking w/o Tw D13 | 1.17 | 98.46 | 0.37 |
| Acetate Shaking w/o Tw D13 | 1.21 | 98.41 | 0.39 |
| Acetate LS/HM Shaking w/o Tw D13 | 1.00 | 98.68 | 0.32 |

Refer to Table 4 for buffer components.
LS/HM: Lower NaCl and higher mannitol levels

TABLE 23

SE-UPLC data for Shaking Study without Polysorbate 80 (Tw) - Day 20

| Sample Name | % Area Total Aggregate | % Monomer Area | % Area Total Degradant |
|---|---|---|---|
| Adalimumab Reference Shaking w/o Tw D20 | 1.35 | 96.75 | 1.90 |
| Acetate Shaking w/o Tw D20 | 1.38 | 98.10 | 0.51 |
| Acetate LS/HM Shaking w/o Tw D20 | 1.14 | 98.39 | 0.47 |

Refer to Table 4 for buffer components.
LS/HM: Lower NaCl and higher mannitol levels

TABLE 24

SE-UPLC data for Shaking Study without Polysorbate 80 - Day 28

| Sample Name | % Area Total Aggregate | % Monomer Area | % Area Total Degradant |
|---|---|---|---|
| Adalimumab Reference Shaking w/o Tw D28 | 1.56 | 95.84 | 2.60 |
| Acetate Shaking w/o Tw D28 | 1.54 | 96.03 | 2.42 |
| Acetate LS/HM Shaking w/o Tw D28 | 1.44 | 96.18 | 2.39 |

Refer to Table 4 for buffer components.
LS/HM: Lower NaCl and higher mannitol levels

TABLE 25

CEX-HPLC data for Shaking Study with Polysorbate 80 - Day 14

| Sample Description | % Acidic Species | % Main Species | % Basic Species | % Extra Basic Species |
|---|---|---|---|---|
| Adalimumab Reference Shaking D14 | 22.4 | 56.9 | 20.2 | 0.5 |
| Acetate Shaking D14 | 21.5 | 58.1 | 19.7 | 0.7 |
| Acetate LS/HM Shaking D14 | 22.5 | 57.2 | 19.6 | 0.7 |

Refer to Table 4 for buffer components.
LS/HM: Lower NaCl and higher mannitol levels

TABLE 26

CEX-HPLC data for Shaking Study with Polysorbate 80 - Day 28

| Sample Description | % Acidic Species | % Main Species | % Basic Species | % Extra Basic Species |
|---|---|---|---|---|
| Adalimumab Reference shaking D28 | 29.0 | 51.2 | 19.5 | 0.4 |

TABLE 26-continued

CEX-HPLC data for Shaking Study with Polysorbate 80 - Day 28

| Sample Description | % Acidic Species | % Main Species | % Basic Species | % Extra Basic Species |
|---|---|---|---|---|
| Acetate shaking D28 | 27.0 | 53.3 | 19.2 | 0.6 |
| Acetate LS/HM shaking D28 | 29.1 | 51.0 | 18.3 | 1.6 |

Refer to Table 4 for buffer components.
LS/HM: Lower NaCl and higher mannitol levels

TABLE 27

CEX-HPLC data for Shaking Study without Polysorbate 80 (Tw) - Day 28

| Sample Description | % Acidic Species | % Main Species | % Basic Species | % Extra Basic Species |
|---|---|---|---|---|
| Adalimumab Reference shaking D28 w/o Tw | 27.8 | 49.6 | 20.5 | 2.2 |
| Acetate shaking D28 w/o Tw | 27.0 | 51.2 | 19.9 | 1.9 |
| Acetate LS/HM shaking D28 w/o Tw | 28.4 | 51.8 | 19.2 | 0.6 |

Refer to Table 4 for buffer components.
LS/HM: Lower NaCl and higher mannitol levels

TABLE 28

Appearance data for Shaking Study with Polysorbate 80

| Day | Adalimumab Reference | Acetate | Acetate LS/HM |
|---|---|---|---|
| 0 | C | C | C |
| 1 | C | C | C |
| 2 | C | C | C |
| 3 | C | C | C |
| 4 | 1P | C | C |
| 7 | 2P | 1P | 1P |
| 8 | 2P | 1P | 1P |
| 9 | 2P | 1P | 1P |
| 10 | 2P | 1P | 1P |
| 11 | 2P | 1P | 1P |
| 14 | 2P | 2P | 1P |
| 15 | 2P | 2P | 1P |
| 16 | 2P | 2P | 1P |
| 17 | 2P | 2P | 1P |
| 18 | 2P | 2P | 1P |
| 21 | 2P | 2P | 1P |
| 22 | 2P | 2P | 1P |
| 23 | 2P | 2P | 1P |
| 24 | 2P | 2P | 1P |
| 25 | 2P | 2P | 1P |
| 28 | 2P | 2P | 1P |

C = Clear,
1P to 5P scale: 1P = particle visible, 5P = many particles visible
Refer to Table 4 for buffer components.
LS/HM: Lower NaCl and higher mannitol levels

TABLE 29

Appearance data for Shaking Study without Polysorbate 80

| Day | Adalimumab Reference | Acetate | Acetate LS/HM |
|---|---|---|---|
| 0 | C | C | C |
| 1 | C | C | C |
| 2 | C | C | C |
| 3 | C | C | C |
| 6 | C | C | 1P |
| 7 | C | C | 1P |
| 8 | C | C | 1P |
| 9 | C | C | 1P |
| 10 | C | C | 1P |
| 13 | C | C | 1P |
| 14 | C | C | 1P |
| 15 | C | C | 1P |
| 16 | C | C | 1P |
| 17 | C | C | 1P |
| 20 | C | C | 1P |
| 21 | C | C | 1P |
| 22 | C | C | 1P |
| 23 | C | C | 1P |
| 24 | C | C | 1P |
| 27 | C | C | 1P |
| 28 | C | C | 1P |

C = Clear,
1P to 5P scale: 1P = particle visible, 5P = many particles visible
Refer to Table 4 for buffer components.
LS/HM: Lower NaCl and higher mannitol levels Real-time Stability at 2-8° C. and −80° C. Prior to the long term real-time stability study, formulation studies including stressed and accelerated temperature, forced oxidation, exposure high shear and freeze-thaw have been conducted to evaluate formulation candidates. The relationship between thermal stability, aggregation, fragmentation, degradation pathways and potency has been observed as a result of these treatments. Experimental series 3, Condition 3 (acetate LS/HM) has shown more protection than the others in several extreme conditions tested.

Storage at 2-8° C. and −80° C. is anticipated for ONS-3010 drug product. Long term real-time stability studies at 2-8° C. and −80° C. have been conducted with timepoints at: 1 month, 5 month, 12 month and 18 month. Samples have been tested with the following methods: SE-UPLC (Tables 32-34), CEX-HPLC (Tables 35-37), CE-SDS (R/NR) (Tables 38-42), L929 BioAssay (Table 43), Peptide Map (Tables 44-46), Particle Count (day 28 2-8° C. Table 8) and Appearance (Tables 30-31).

Testing results on ONS-3010 samples formulated with the three different conditions show no significant biochemical change according to SE-UPLC (FIGS. 25-28) and bioassay results are equivalent and within method variability. There were no significant differences in the visual appearance for formulation conditions 1 and 3 (Tables 30 and 31). Sub-visible particle counts for day 28 timepoint are recorded in Table 8. At the day 28 timepoint, lower salt (formulation condition 3 Acetate LS/HM) appears to further reduce particles at 2-10 micron relative to the adalimumab reference formulation and the higher salt formulation. Stability evaluation for Condition 2 was discontinued after the 5 month time point and stability sample was subsequently frozen at −80° C. for future testing if required.

TABLE 30

Appearance for 2-8° C. Real time incubation

| Day | Adalimumab Reference | Acetate | Acetate LS/HM |
|---|---|---|---|
| 0 | C | C | C |
| 1 | C | C | C |

TABLE 30-continued

Appearance for 2-8° C. Real time incubation

| Day | Adalimumab Reference | Acetate | Acetate LS/HM |
|---|---|---|---|
| 4 | C | C | C |
| 5 | C | C | C |
| 6 | C | C | C |
| 7 | C | C | C |
| 8 | C | C | C |
| 11 | C | C | C |
| 12 | C | C | C |
| 13 | C | C | C |
| 14 | C | C | C |
| 15 | C | C | C |
| 18 | C | C | C |
| 19 | C | C | C |
| 20 | C | C | C |
| 21 | C | C | C |
| 22 | C | C | C |
| 25 | C | C | C |
| 26 | 1P | 1P | 1P |
| 27 | 1P | 1P | 1P |
| 28 | 1P | 1P | 1P |
| 5 month | 1P | 1P | 1P |
| 12 month | 1P | 2P | 1P |
| 18 month | 1P | 2P | 1P |

C = Clear,
1P to 5P scale: 1P = particle visible, 5P = many particles visible
Refer to Table 4 for buffer components.
LS/HM: Lower NaCl and higher mannitol levels

TABLE 31

Appearance for −80° C. Real time incubation

| Month | Condition 1 | Condition 2 | Condition 3 |
|---|---|---|---|
| 5 | 1P | 2P | 1P |
| 12 | 1P | Not tested | 1P |
| 18 | 1P | Not tested | 1P |

C = Clear,
1P to 5P scale: 1P = particle visible, 5P = many particles visible
Refer to Table 4 for buffer components.
LS/HM: Lower NaCl and higher mannitol levels

TABLE 32

SE-UPLC % HMWS for 2-8° C. and −80° C. incubation
% HMWS

| Sample | 2-8° C. T0 | 2-8° C. 28 d | 2-8° C. 5 month | 2-8° C. 12 month | 2-8° C. 18 month | −80° C. 5 month | −80° C. 12 month | −80° C. 18 month |
|---|---|---|---|---|---|---|---|---|
| 1. Adalimumab reference | 0.74 | 0.76 | 0.87 | 0.98 | 1.07 | 0.71 | 0.68 | 0.68 |
| 2. Acetate | 0.71 | 0.75 | 0.91 | Not tested | Not tested | 0.69 | Not tested | Not tested |
| 3. Acetate LS/HM | 0.7 | 0.68 | 0.83 | 0.96 | 1.03 | 0.66 | 0.64 | 0.64 |

Refer to Table 4 for buffer components.
LS/HM: Lower NaCl and higher mannitol levels

TABLE 33

SE-UPLC % Monomer for 2-8° C. and −80° C. incubation
% Monomer

| Sample | 2-8° C. T0 | 2-8° C. 28 d | 2-8° C. 5 month | 2-8° C. 12 month | 2-8° C. 18 month | −80° C. 5 month | −80° C. 12 month | −80° C. 18 month |
|---|---|---|---|---|---|---|---|---|
| 1. Adalimumab reference | 99.16 | 99.12 | 99.03 | 98.73 | 98.60 | 99.22 | 99.17 | 99.32 |
| 2. Acetate | 99.14 | 99.17 | 98.96 | Not tested | Not tested | 99.23 | Not tested | Not tested |
| 3. Acetate LS/HM | 99.16 | 99.25 | 99.09 | 98.75 | 98.62 | 99.27 | 99.16 | 99.36 |

Refer to Table 4 for buffer components.
LS/HM: Lower NaCl and higher mannitol levels

TABLE 34

SE-UPLC % LMWS for 2-8° C. and −80° C. incubation
% LMWS

| Sample | 2-8° C. T0 | 2-8° C. 28 d | 2-8° C. 5 month | 2-8° C. 12 month | 2-8° C. 18 month | −80° C. 5 month | −80° C. 12 month | −80° C. 18 month |
|---|---|---|---|---|---|---|---|---|
| 1. Adalimumab reference | 0.1 | 0.12 | 0.10 | 0.29 | 0.34 | 0.06 | 0.15 | 0.00 |

TABLE 34-continued

SE-UPLC % LMWS for 2-8° C. and −80° C. incubation

| | | | | % LMWS | | | | |
|---|---|---|---|---|---|---|---|---|
| Sample | 2-8° C. T0 | 2-8° C. 28 d | 2-8° C. 5 month | 2-8° C. 12 month | 2-8° C. 18 month | −80° C. 5 month | −80° C. 12 month | −80° C. 18 month |
| 2. Acetate | 0.15 | 0.08 | 0.14 | Not tested | Not tested | 0.08 | Not tested | Not tested |
| 3. Acetate LS/HM | 0.14 | 0.07 | 0.08 | 0.30 | 0.36 | 0.07 | 0.20 | 0.00 |

Refer to Table 4 for buffer components.
LS/HM: Lower NaCl and higher mannitol levels

TABLE 35

CEX-HPLC % Acidic Species for 2-8° C. and −80° C. incubation

| | | | | % Acidic Species | | | | |
|---|---|---|---|---|---|---|---|---|
| Sample | 2-8° C. T0 | 2-8° C. 28 d | 2-8° C. 5 month | 2-8° C. 12 month | 2-8° C. 18 month | −80° C. 5 month | −80° C. 12 month | −80° C. 18 month |
| 1. Adalimumab reference | 15.5 | 15.0 | 15.4 | 16.7 | 17.0 | 15.0 | 17.7 | 15.3 |
| 2. Acetate | 15.7 | 15.2 | 15.0 | Not tested | Not tested | 14.5 | Not tested | Not tested |
| 3. Acetate LS/HM | 15.5 | 15.0 | 15.7 | 16.8 | 17.0 | 15.2 | 16.5 | 15.3 |

Refer to Table 4 for buffer components.
LS/HM: Lower NaCl and higher mannitol levels

TABLE 36

CEX-HPLC % Main Species for 2-8° C. and −80° C. incubation

| | | | | % Main Species | | | | |
|---|---|---|---|---|---|---|---|---|
| Sample | 2-8° C. T0 | 2-8° C. 28 d | 2-8° C. 5 month | 2-8° C. 12 month | 2-8° C. 18 month | −80° C. 5 month | −80° C. 12 month | −80° C. 18 month |
| 1. Adalimumab reference | 64.4 | 64.8 | 64.4 | 63.2 | 62.5 | 65.4 | 63.1 | 65.0 |
| 2. Acetate | 64.1 | 64.9 | 64.5 | Not tested | Not tested | 65.6 | Not tested | Not tested |
| 3. Acetate LS/HM | 64.0 | 65.2 | 64.1 | 63.3 | 63.1 | 64.6 | 64.3 | 65.1 |

Refer to Table 4 for buffer components.
LS/HM: Lower NaCl and higher mannitol levels

TABLE 37

CEX-HPLC % Basic Species for 2-8° C. and −80° C. incubation

| | | | | % Basic Species | | | | |
|---|---|---|---|---|---|---|---|---|
| Sample | 2-8° C. T0 | 2-8° C. 28 d | 2-8° C. 5 month | 2-8° C. 12 month | 2-8° C. 18 month | −80° C. 5 month | −80° C. 12 month | −80° C. 18 month |
| 1. Adalimumab reference | 18.5 | 19.2 | 20.2 | 20.1 | 20.4 | 19.7 | 19.2 | 19.7 |
| 2. Acetate | 18.8 | 18.8 | 20.5 | Not tested | Not tested | 20.0 | Not tested | Not tested |
| 3. Acetate LS/HM | 18.6 | 19.0 | 20.2 | 19.8 | 20.0 | 20.2 | 19.2 | 19.7 |

Refer to Table 4 for buffer components.
LS/HM: Lower NaCl and higher mannitol levels

TABLE 38

CE-SDS Reduced Light Chain % area for 2-8° C. and −80° C. incubation

| | | | | Light Chain % area | | | | |
|---|---|---|---|---|---|---|---|---|
| Sample | 2-8° C. T0 | 2-8° C. 28 d | 2-8° C. 5 month | 2-8° C. 12 month | 2-8° C. 18 month | −80° C. 5 month | −80° C. 12 month | −80° C. 18 month |
| 1. Adalimumab reference | 29.5 | 29.6 | 29.9 | 32.6 | 32.7 | 30.1 | 32.5 | 31.3 |

TABLE 38-continued

CE-SDS Reduced Light Chain % area for 2-8° C. and −80° C. incubation
Light Chain % area

| Sample | 2-8° C. T0 | 2-8° C. 28 d | 2-8° C. 5 month | 2-8° C. 12 month | 2-8° C. 18 month | −80° C. 5 month | −80° C. 12 month | −80° C. 18 month |
|---|---|---|---|---|---|---|---|---|
| 2. Acetate | 29.6 | 29.3 | 29.8 | Not tested | Not tested | 30.0 | Not tested | Not tested |
| 3. Acetate LS/HM | 29.6 | 29.0 | 29.9 | 32.5 | 31.4 | 30.0 | 32.6 | 32.3 |

Refer to Table 4 for buffer components.
LS/HM: Lower NaCl and higher mannitol levels

TABLE 39

CE-SDS Reduced Heavy Chain % area for 2-8° C. and −80° C. incubation
Heavy Chain % area

| Sample | 2-8° C. T0 | 2-8° C. 28 d | 2-8° C. 5 month | 2-8° C. 12 month | 2-8° C. 18 month | −80° C. 5 month | −80° C. 12 month | −80° C. 18 month |
|---|---|---|---|---|---|---|---|---|
| 1. Adalimumab reference | 67.5 | 67.4 | 67.5 | 65.8 | 65.5 | 67.7 | 65.9 | 66.0 |
| 2. Acetate | 67.4 | 67.9 | 67.5 | Not tested | Not tested | 67.5 | Not tested | Not tested |
| 3. Acetate LS/HM | 66.4 | 67.6 | 67.4 | 65.7 | 66.9 | 67.2 | 65.8 | 66.0 |

Refer to Table 4 for buffer components.
LS/HM: Lower NaCl and higher mannitol levels

TABLE 40

CE-SDS Reduced Intermediate Species % area for 2-8° C. and −80° C. incubation
Intermediate Species % area

| Sample | 2-8° C. T0 | 2-8° C. 28 d | 2-8° C. 5 month | 2-8° C. 12 month | 2-8° C. 18 month | −80° C. 5 month | −80° C. 12 month | −80° C. 18 month |
|---|---|---|---|---|---|---|---|---|
| 1. Adalimumab reference | 2.1 | 2.0 | 1.6 | 0.2 | 0.6 | 1.1 | 0.2 | 0.9 |
| 2. Acetate | 2.0 | 2.0 | 1.5 | Not tested | Not tested | 1.2 | Not tested | Not tested |
| 3. Acetate LS/HM | 1.4 | 2.3 | 1.7 | 0.3 | 0.5 | 1.4 | 0.2 | 0.5 |

Refer to Table 4 for buffer components. LS/HM: Lower NaCl and higher mannitol levels

TABLE 41

CE-SDS Non-Reduced Main Peak % Area for 2-8° C. and −80° C. incubation
Main peak % Area

| Sample | 2 to 8° C. T0 | 2 to 8° C. 28 d | 2 to 8° C. 5 month | 2 to 8° C. 12 month | 2-8° C. 18 month | −80° C. 5 month | −80° C. 12 month | −80° C. 18 month |
|---|---|---|---|---|---|---|---|---|
| 1. Adalimumab reference | 91.4 | 91.7 | 92.2 | 93.1 | 93.9 | 92.4 | 93.3 | 93.9 |
| 2. Acetate | 91.8 | 91.7 | 92.3 | Not tested | Not tested | 92.2 | Not tested | Not tested |
| 3. Acetate LS/HM | 91.8 | 93.1 | 92.7 | 93.4 | 93.9 | 92.4 | 93.1 | 93.9 |

Refer to Table 4 for buffer components. LS/HM: Lower NaCl and higher mannitol levels

TABLE 42

CE-SDS Non-Reduced % Area of Pre-Main Peak Species for 2-8° C. and −80° C. incubation
% Area of pre-main peak species

| Sample | 2 to 8° C. T0 | 2 to 8° C. 28 d | 2 to 8° C. 5 month | 2 to 8° C. 12 month | 2-8° C. 18 month | −80° C. 5 month | −80° C. 12 month | −80° C. 18 month |
|---|---|---|---|---|---|---|---|---|
| 1. Adalimumab reference | 8.6 | 5.8 | 7.8 | 6.9 | 6.1 | 7.6 | 6.7 | 6.1 |
| 2. Acetate | 8.2 | 5.9 | 7.7 | Not tested | Not tested | 7.8 | Not tested | Not tested |
| 3. Acetate LS/HM | 8.2 | 6.9 | 7.3 | 6.6 | 6.1 | 7.6 | 6.9 | 6.1 |

Refer to Table 4 for buffer components. LS/HM: Lower NaCl and higher mannitol levels

TABLE 43

Bioassay L929 for 2-8° C. and −80° C. incubation
Potency Mean % ± Std Dev.

| Sample | 2 to 8° C. T0 | 2 to 8° C. 28 d | 2 to 8° C. 5 month | 2 to 8° C. 12 month | 2-8° C. 18 month | −80° C. 5 month | −80° C. 12 month | −80° C. 18 month |
|---|---|---|---|---|---|---|---|---|
| 1. Adalimumab reference | 96.76 ± 16.50 | 108.68 ± 4.08 | 98.76 ± 6.22 | 98.81 ± 1.73 | 102.03 ± 6.52 | 97.39 ± 6.82 | 101.38 ± 3.85 | 101.73 ± 5.89 |
| 2. Acetate | 93.40 ± 15.49 | 103.17 ± 3.19 | 100.37 ± 4.60 | Not tested | Not tested | 95.80 ± 7.77 | Not tested | Not tested |
| 3. Acetate LS/HM | 91.23 ± 11.44 | 107.92 ± 3.08 | 103.39 ± 8.05 | 101 ± 3.62 | 100.37 ± 5.67 | 95.27 ± 3.63 | 94.28 ± 1.62 | 102.76 ± 4.78 |

Refer to Table 4 for buffer components. LS/HM: Lower NaCl and higher mannitol levels

TABLE 44

N-terminal PyroE for 2-8° C. and −80° C. incubation
N-terminal PyroE

| Sample | 2-8° C. T0 | 2-8° C. 28 d | 2-8° C. 5 month | 2-8° C. 12 month | 2-8° C. 18 month | −80° C. 5 month | −80° C. 12 month | −80° C. 18 month |
|---|---|---|---|---|---|---|---|---|
| 1. Adalimumab reference | 1.5 | 2.4* | 1.7 | 1.7 | 1.7 | 1.6 | 1.4 | 1.2 |
| 2. Acetate | 1.5 | 2.4* | 1.4 | Not tested | Not tested | 1.5 | Not tested | Not tested |
| 3. Acetate LS/HM | 1.5 | 2.3* | 1.7 | 1.5 | 1.6 | 1.6 | 1.4 | 1.3 |

*samples at 2-8° C. for 28 days were tested alone with a separate set of samples at time zero.
Refer to Table 4 for buffer components. LS/HM: Lower NaCl and higher mannitol levels

TABLE 45

Oxidation for 2-8° C. and −80° C. incubation
Sum of Oxidation

| Sample | 2-8° C. T0 | 2-8° C. 28 d | 2-8° C. 5 month | 2-8° C. 12 month | 2-8° C. 18 month | −80° C. 5 month | −80° C. 12 month | −80° C. 18 month |
|---|---|---|---|---|---|---|---|---|
| 1. Adalimumab reference | 4.7 | 5.2 | 5.4 | 6.3 | 5.8 | 4.8 | 5.9 | 5.2 |
| 2. Acetate | 5.4 | 7.2 | 4.7 | Not tested | Not tested | 4.8 | Not tested | Not tested |
| 3. Acetate LS/HM | 5.2 | 5.1 | 5.0 | 6.7 | 6.7 | 4.3 | 5.7 | 5.2 |

Refer to Table 4 for buffer components. LS/HM: Lower NaCl and higher mannitol levels

TABLE 46

Isomerization for 2-8° C. and −80° C. incubation
Sum of Isomerization

| Sample | 2-8° C. T0 | 2-8° C. 28 d | 2-8° C. 5 month | 2-8° C. 12 month | 2-8° C. 18 month | −80° C. 5 month | −80° C. 12 month | −80° C. 18 month |
|---|---|---|---|---|---|---|---|---|
| 1. Adalimumab reference | LOD | LOD | LOD | 0.24 | 0.23 | LOD | 0.15 | 0.11 |
| 2. Acetate | LOD | LOD | LOD | Not tested | Not tested | LOD | Not tested | Not tested |
| 3. Acetate LS/HM | LOD | LOD | LOD | 0.21 | 0.24 | LOD | 0.15 | 0.15 |

Refer to Table 4 for buffer components. LS/HM: Lower NaCl and higher mannitol levels

EXAMPLE 4

Forced Degradation Evaluation

The data presented in this Example stem from forced degradation testing, and illustrate the enhanced stability with the acetate LS/HM buffer composition for ONS-3010. Test Sample as follows:
A. 51.0 mg/mL (acetate LS/HM buffer formulation) and 52.6 mg/mL (Adalimumab reference formulation)
B. 48.5 mg/mL (acetate LS/HM buffer formulation) and 50.3 mg/mL (Adalimumab reference formulation)

Purity SE-UPLC: SE-UPLC monitors ONS-3010 size homogeneity under non-denaturing conditions. The SE-UPLC testing method separates proteins based on size. The method is isocratic with a sodium phosphate running buffer, using a Waters Acquity UPLC BEH200 SEC column (1.7 μm, 4.6×150 mm). Peaks are monitored using absorbance at 280 nm. Species eluting before the monomer peak are aggregates (HMWS) and peaks eluting after the monomer peak are degradants (LMWS).

Purity CE-SDS (NR): CE-SDS analysis is used to monitor ONS-3010 size homogeneity under denaturing conditions, with non-reducing conditions, using a Beckman PA800 plus instrument. Samples are treated with an alkylation agent and SDS is bound to all proteins via a sample buffer. A polymer matrix is filled into the capillary prior to sample analysis. Samples are electrokinetically introduced to the capillary by an applied voltage, then electrophoresis is performed by applying a constant voltage to the capillary. The SDS treated proteins have a mass to charge properties that are proportional to the protein weights which allows for the separation of the SDS-bound proteins by the differences in molecular weight. Test article proteins are quantified by UV detection at 220 nm.

Peptide Map: UPLC Peptide mapping is used to characterize a protein's primary structure. ONS-3010 is digested with trypsin and the resulting peptides are separated by RP-UPLC. The characteristic peptide map fingerprint is analyzed for peak relative retention time and overall peak pattern compared with the reference.

55° C. Treatment: A 55° C. study was conducted on 2 lots of ONS-3010 in solution. The results indicated the ONS-3010 antibody in the acetate LS/HM buffer formulation demonstrated a slower rate of degradation compared to the same antibody in the Adalimumab reference formulation, displaying enhanced stability at 55° C. for aggregation and % intact protein on non-reduced CE as well as peptide map. There was also a visual difference due to the antibody in the Adalimumab reference buffer becoming opalescent by day 10 of treatment compared to the antibody in the acetate LS/HM buffer formulation, which remained clear throughout 10 days of treatment.

Tables 48-50 show the longest timepoints with significant differences. There was a consistent trend throughout the treatment, however.

TABLE 47

Summary of Forced Temperature Test for ONS-3010 at 55° C. for 10 Days

| Product | Buffer | Treatment | Visual | SEC % Aggregate | SEC % Monomer | SEC % Degradant | NR-CE % Intact |
|---|---|---|---|---|---|---|---|
| ONS-3010-BDS | Acetate LS/HM buffer | Untreated | clear | 0.5 | 99.2 | 0.4 | 94.9 |
| | | 55° C. D1 | clear | 1.8 | 97.3 | 0.9 | 91.2 |
| | | 55° C. D2 | clear | 3.2 | 95.6 | 1.3 | 90.0 |
| | | 55° C. D7 | clear | 7.6 | 84.0 | 8.4 | 85.0 |
| | | 55° C. D10 | clear | 10.3 | 79.8 | 9.9 | 83.0 |
| ONS-3010-BDS | Adalimumab reference | Untreated | clear | 0.5 | 99.4 | 0.2 | 96.2 |
| | | 55° C. D1 | clear | 2.3 | 96.9 | 0.8 | 88.2 |
| | | 55° C. D2 | clear | 3.8 | 95.2 | 1.0 | 83.1 |
| | | 55° C. D7 | clear | 10.3 | 83.3 | 6.4 | 77.1 |
| | | 55° C. D10 | opalescent | 13.7 | 78.9 | 7.4 | 75.1 |

Note:
No change in potency for treated samples in both formulations

TABLE 48

Summary of Forced Temperature Test for ONS-3010 and Adalimumab at 55° C. for 10 Days

| | | | | PTM | | | | |
| | | | | | Oxidation | | Isomerization | |
| Product | Buffer | Treatment | Total Deamidation | M256 | M432 | D31 | D284 | Pyro-E |
|---|---|---|---|---|---|---|---|---|
| ONS-3010-BDS | Acetate LS/HM buffer | Untreated | 29 | 3.1 | 1.2 | <LOD | 0.1 | 1.2 |
| | | 55° C. D1 | 29.4 | 3.3 | 1.0 | 0.2 | 0.9 | 1.9 |
| | | 55° C. D2 | 30.5 | 3.8 | 1.0 | 0.5 | 2.3 | 2.6 |
| | | 55° C. D7 | 37.7 | 5.0 | 1.7 | 2.9 | 8.4 | 7.0 |
| | | 55° C. D10 | 38.8 | 5.5 | 1.9 | 4.9 | 12.5 | 8.5 |
| ONS-3010-BDS | Adalimumab reference | Untreated | 26.9 | 2.6 | 1.1 | <LOD | 0.1 | 1.2 |
| | | 55° C. D1 | 29.7 | 4.0 | 1.2 | 0.1 | 1.3 | 2.2 |
| | | 55° C. D2 | 31.9 | 4.6 | 1.5 | 0.5 | 3.7 | 3.6 |
| | | 55° C. D7 | 30.7 | 5.7 | 2.6 | 2.2 | 11.0 | 8.8 |
| | | 55° C. D10 | 39.2 | 6.6 | 2.4 | 3.8 | 14.4 | 12.1 |

Note:
No change in potency for treated samples in both formulations.

pH 3.0 Treatment: Treatment at pH 3.0 was conducted on 2 lots of ONS-3010 antibody. The ONS-3010 BDS in the acetate LS/HM buffer formulation demonstrated a higher level of stability based on aggregation compared to the same antibody in the Adalimumab reference formulation. There was also a visual difference, with the antibody in the adalimumab reference buffer becoming cloudy after 12 hours of treatment compared to the antibody in the acetate LS/HM buffer formulation, which remained clear throughout 12 hours of treatment at pH 3.

TABLE 49

Summary of Low pH Test for ONS-3010 at pH 3 for up to 12 Hours*

| | | | | SEC | | |
| Product | Buffer | Treatment | Visual | % Aggregate | % Monomer | % Degradant |
|---|---|---|---|---|---|---|
| ONS-3010-BDS | Acetate LS/HM buffer | Untreated | clear | 0.6 | 99.4 | 0.1 |
| | | 0.5 Hrs. | clear | 2.5 | 97.5 | 0.0 |
| | | 1 Hrs. | clear | 3.3 | 96.7 | 0.1 |
| | | 2 Hrs. | clear | 4.4 | 95.4 | 0.2 |
| | | 3 Hrs. | clear | 5.6 | 94.2 | 0.2 |
| | | 12 Hrs. | clear | 12.5 | 87.2 | 0.4 |
| ONS-3010-BDS | Adalimumab reference | Untreated | clear | 0.5 | 99.5 | 0.0 |
| | | 0.5 Hrs. | clear | 7.7 | 92.1 | 0.2 |
| | | 1 Hrs. | clear | 11.1 | 88.7 | 0.2 |
| | | 2 Hrs. | clear | 15.8 | 84.0 | 0.2 |
| | | 3 Hrs. | clear | 18.3 | 81.5 | 0.3 |
| | | 12 Hrs. | cloudy | 30.5 | 69.0 | 0.5 |

Note:
No change in potency for treated samples in both formulations.
*There is a 2-3 fold difference in amount of aggregates formed in the adalimumab reference (citrate-phosphate buffer) vs. the acetate LS/HM buffer over 1-3 Hours at pH 3.0. These data suggest that acetate LS/HM buffer offers greater stability against aggregation at pH 3.0. The acetate LS/HM buffer formulation shows greater protection at low pH compared to the adalimumab reference formulation.

EXAMPLE 5

Summary

Results based on stressed and accelerated stability studies indicate promising reformulation conditions with comparable and/or improved degradation rates relative to that of the antibody in the adalimumab reference formulation. Formulation condition #3 (acetate LS/HM) used in experimental series 3, provides a protective effect to ONS-3010 relative to the adalimumab reference buffer. This observation is consistent in forced oxidation and shaking studies, as well as at elevated temperatures. The acetate LS/HM buffer formulation provides improved thermal, conformational and colloidal stability to ONS-3010, which indeed translates into comparable shelf life and/or improved product quality.

After 18 months of storage at 2-8° C. and −80° C., Condition 1 (adalimumab reference) and Condition 3 (acetate LS/HM buffer formulation) were stable and showed no significant change.

Adalimumab Reference Formulation Buffer Components:
105.45 mM Sodium Chloride
5.53 mM Sodium Phosphate, Monobasic Dihydrate
8.57 mM Sodium Phosphate, Dibasic Dihydrate
1.02 mM Sodium Citrate, Dihydrate
6.19 mM Citric Acid, Monohydrate
65.87 mM Mannitol
0.1% Polysorbate-80
pH 5.20 (adjust with sodium hydroxide as needed)
Q.S. with Sterile water for injection ONS-3010 Acetate LS/HM Formulation Buffer Components:
26.35 mM Sodium Chloride
1.00 mM Sodium Acetate Trihydrate
19.00 mM Glacial Acetic Acid
203.00 mM Mannitol 0.1% Polysorbate-80
pH 5.20 (adjust with sodium hydroxide as needed)
Q.S. with Sterile Water for injection

TABLE 50

Comparison Adalimumab Reference and ONS-3010 Formulation Compositions

| Component | Concentration in Adalimumab Reference Formulation Buffer (per 0.8 mL) | Concentration in ONS-3010 Formulation Buffer (per 0.8 mL) |
|---|---|---|
| Active | 40 mg | 40 mg |
| Sodium chloride | 4.93 mg | 1.23 mg |
| Monobasic sodium phosphate dihydrate | 0.69 mg | — |
| Dibasic sodium phosphate dihydrate | 1.22 mg | — |
| Sodium citrate dihydrate | 0.24 mg | — |
| Citric acid monohydrate | 1.04 mg | — |
| Sodium Acetate Trihydrate | — | 0.11 mg |
| Glacial Acetic Acid | — | 0.91 mg |
| Mannitol | 9.6 mg | 29.58 mg |
| Polysorbate 80 | 0.8 mg | 0.8 mg |
| pH | 5.2 | 5.2 |

The invention is not limited to the embodiments described and exemplified above, but is capable of variation and modification within the scope of the appended claims.

We claim:

1. A buffered antibody formulation, comprising an antibody comprising a heavy chain comprising the amino acid sequence of SEQ ID NO: 1 and a light chain comprising the amino acid sequence of SEQ ID NO: 2, a buffer comprising from about 0.7 mM to about 1.3 mM of an acetate salt, from about 200 mM to about 206 mM of mannitol, from about 16 mM to about 22 mM of glacial acetic acid, and from about 24 mM to about 28 mM of sodium chloride, and about 0.07% (v/v) to about 0.15% (v/v) of polysorbate 80, wherein the antibody formulation has a pH of from about 5.1 to about 5.3.

2. The buffered antibody formulation of claim 1, wherein the formulation comprises from about 30 mg to about 50 mg of the antibody.

3. The buffered antibody formulation of claim 1, wherein the formulation comprises from about 35 mg to about 45 mg of the antibody.

4. The buffered antibody formulation of claim 1, wherein the formulation comprises from about 37 mg to about 43 mg of the antibody.

5. The buffered antibody formulation of claim 1, wherein the formulation comprises about 40 mg of the antibody.

6. The buffered antibody formulation of claim 1, wherein the buffer comprises from about 0.8 mM to about 1.2 mM of the acetate salt.

7. The buffered antibody formulation of claim 1, wherein the buffer comprises from about 0.9 mM to about 1.1 mM of the acetate salt.

8. The buffered antibody formulation of claim 1, wherein the buffer comprises about 1 mM of the acetate salt.

9. The buffered antibody formulation of claim 1, wherein the buffer comprises from about 201 mM to about 205 mM of mannitol.

10. The buffered antibody formulation of claim 1, wherein the buffer comprises from about 202 mM to about 204 mM of mannitol.

11. The buffered antibody formulation of claim 1, wherein the buffer comprises about 203 mM of mannitol.

12. The buffered antibody formulation of claim 1, wherein the buffer comprises from about 17 mM to about 21 mM of glacial acetic acid.

13. The buffered antibody formulation of claim 1, wherein the buffer comprises from about 18 mM to about 20 mM of glacial acetic acid.

14. The buffered antibody formulation of claim 1, wherein the buffer comprises about 19 mM of glacial acetic acid.

15. The buffered antibody formulation of claim 1, wherein the buffer comprises from about 25 mM to about 27 mM of sodium chloride.

16. The buffered antibody formulation of claim 1, wherein the buffer comprises about 26 mM of sodium chloride.

17. The buffered antibody formulation of claim 1, wherein the buffer comprises about 26.35 mM of sodium chloride.

18. The buffered antibody formulation of claim 1, wherein the formulation comprises from about 0.08% (v/v) to about 0.12% (v/v) of polysorbate 80.

19. The buffered antibody formulation of claim 1, wherein the formulation comprises from about 0.09% (v/v) to about 0.11% (v/v) of polysorbate 80.

20. The buffered antibody formulation of claim 1, wherein the formulation comprises about 0.1% (v/v) of polysorbate 80.

21. The buffered antibody formulation of claim 1, wherein the formulation has a pH of about 5.2.

22. A buffered antibody formulation, comprising an antibody comprising a heavy chain comprising the amino acid sequence of SEQ ID NO: 1 and a light chain comprising the amino acid sequence of SEQ ID NO: 2, a buffer comprising about 0.8 mM to about 1.2 mM of an acetate salt, about 201 mM to about 205 mM of mannitol, about 17 mM to about 21 mM of glacial acetic acid, and about 25 mM to about 27 mM of sodium chloride, and about 0.08% to about 0.15% (by volume) of polysorbate 80, wherein the antibody formulation has a pH of from about 5.1 to about 5.3.

23. The buffered antibody formulation of claim 22, wherein the formulation comprises from about 30 mg to about 50 mg of the antibody.

24. The buffered antibody formulation of claim 22, wherein the formulation comprises from about 35 mg to about 45 mg of the antibody.

25. The buffered antibody formulation of claim 22, wherein the formulation comprises from about 37 mg to about 43 mg of the antibody.

26. The buffered antibody formulation of claim 22, wherein the formulation comprises about 40 mg of the antibody.

27. The buffered antibody formulation of claim 22, wherein the buffer comprises from about 0.9 mM to about 1.1 mM of the acetate salt.

28. The buffered antibody formulation of claim 22, wherein the buffer comprises about 1 mM of the acetate salt.

29. The buffered antibody formulation of claim 22, wherein the buffer comprises from about 202 mM to about 204 mM of mannitol.

30. The buffered antibody formulation of claim 22, wherein the buffer comprises about 203 mM of mannitol.

31. The buffered antibody formulation of claim 22, wherein the buffer comprises from about 18 mM to about 20 mM of glacial acetic acid.

32. The buffered antibody formulation of claim 22, wherein the buffer comprises about 19 mM of glacial acetic acid.

33. The buffered antibody formulation of claim 22, wherein the buffer comprises about 26 mM of sodium chloride.

34. The buffered antibody formulation of claim 22, wherein the buffer comprises about 27 mM of sodium chloride.

35. The buffered antibody formulation of claim 22, wherein the buffer comprises about 26.35 mM of sodium chloride.

36. The buffered antibody formulation of claim 22, wherein the formulation comprises from about 0.09% (v/v) to about 0.11% (v/v) of polysorbate 80.

37. The buffered antibody formulation of claim 22, wherein the formulation comprises about 0.1% (v/v) of polysorbate 80.

38. The buffered antibody formulation of claim 22, wherein the formulation has a pH of about 5.2.

39. A buffered antibody formulation, comprising an antibody comprising a heavy chain comprising the amino acid sequence of SEQ ID NO: 1 and a light chain comprising the amino acid sequence of SEQ ID NO: 2, a buffer comprising about 0.9 mM to about 1.1 mM of an acetate salt, about 202 mM to about 204 mM of mannitol, about 18 mM to about 20 mM of glacial acetic acid, and about 25.35 mM to about 26.35 mM of sodium chloride, and about 0.09% to about 0.11% (by volume) of polysorbate 80, wherein the antibody formulation has a pH of from about 5.1 to about 5.3.

40. The buffered antibody formulation of claim 39, wherein the formulation comprises from about 30 mg to about 50 mg of the antibody.

41. The buffered antibody formulation of claim 39, wherein the formulation comprises from about 35 mg to about 45 mg of the antibody.

42. The buffered antibody formulation of claim 39, wherein the formulation comprises from about 37 mg to about 43 mg of the antibody.

43. The buffered antibody formulation of claim 39, wherein the formulation comprises about 40 mg of the antibody.

44. The buffered antibody formulation of claim 39, wherein the buffer comprises about 1 mM of the acetate salt.

45. The buffered antibody formulation of claim 39, wherein the buffer comprises about 203 mM of mannitol.

46. The buffered antibody formulation of claim 39, wherein the buffer comprises about 19 mM of glacial acetic acid.

47. The buffered antibody formulation of claim 39, wherein the buffer comprises about 26 mM of sodium chloride.

48. The buffered antibody formulation of claim 39, wherein the buffer comprises about 26.35 mM of sodium chloride.

49. The buffered antibody formulation of claim 39, wherein the formulation comprises about 0.1% (v/v) of polysorbate 80.

50. The buffered antibody formulation of claim 39, wherein the formulation has a pH of about 5.2.

51. A buffered antibody formulation, comprising an antibody comprising a heavy chain comprising the amino acid sequence of SEQ ID NO: 1 and a light chain comprising the amino acid sequence of SEQ ID NO: 2, a buffer comprising about 1 mM of sodium acetate trihydrate, about 203 mM of mannitol, about 19 mM of glacial acetic acid, and about 26.35 mM of sodium chloride, and about 0.1% (by volume) of polysorbate 80, wherein the antibody formulation has a pH of about 5.2.

52. The buffered antibody formulation of claim 51, wherein the formulation comprises from about 30 mg to about 50 mg of the antibody.

53. The buffered antibody formulation of claim 51, wherein the formulation comprises from about 35 mg to about 45 mg of the antibody.

54. The buffered antibody formulation of claim 51, wherein the formulation comprises from about 37 mg to about 43 mg of the antibody.

55. The buffered antibody formulation of claim 51, wherein the formulation comprises about 40 mg of the antibody.

56. The buffered antibody formulation of claim 1 for use in the treatment of Rheumatoid Arthritis, Juvenile Idiopathic Arthritis, Psoriatic Arthritis, Ankylosing Spondylitis, Crohn's Disease, Plaque Psoriasis or Ulcerative Colitis.

57. A kit, comprising the buffered antibody formulation of claim 1 and instructions for using the antibody formulation in a method for treating Rheumatoid Arthritis, Juvenile Idiopathic Arthritis, Psoriatic Arthritis, Ankylosing Spondylitis, Crohn's Disease, Plaque Psoriasis or Ulcerative Colitis.

58. The kit of claim 57, further comprising a device for injecting the antibody formulation into a subject.

59. The kit of claim 58, wherein the device comprises a syringe and a needle.

60. The kit of claim 58, wherein the device comprises a catheter.

61. The buffered antibody formulation of claim 1, wherein the acetate salt comprises sodium acetate trihydrate.

62. The buffered antibody formulation of claim 22, wherein the acetate salt comprises sodium acetate trihydrate.

63. The buffered antibody formulation of claim 39, wherein the acetate salt comprises sodium acetate trihydrate.

64. A buffer formulation for antibody storage, comprising a buffer comprising from about 0.7 mM to about 1.3 mM of an acetate salt, from about 200 mM to about 206 mM of mannitol, from about 16 mM to about 22 mM of glacial acetic acid, and from about 24 mM to about 28 mM of sodium chloride, and about 0.07% (v/v) to about 0.15% (v/v) of polysorbate 80, wherein the formulation has a pH of from about 5.1 to about 5.3.

65. The buffer formulation of claim 64, wherein the buffer comprises from about 0.8 mM to about 1.2 mM of the acetate salt.

66. The buffer formulation of claim 64, wherein the buffer comprises from about 0.9 mM to about 1.1 mM of the acetate salt.

67. The buffer formulation of claim 64, wherein the buffer comprises about 1 mM of the acetate salt.

68. The buffer formulation of claim 64, wherein the buffer comprises from about 201 mM to about 205 mM of mannitol.

69. The buffer formulation of claim 64, wherein the buffer comprises from about 202 mM to about 204 mM of mannitol.

70. The buffer formulation of claim 64, wherein the buffer comprises about 203 mM of mannitol.

71. The buffer formulation of claim 64, wherein the buffer comprises from about 17 mM to about 21 mM of glacial acetic acid.

72. The buffer formulation of claim 64, wherein the buffer formulation comprises from about 18 mM to about 20 mM of glacial acetic acid.

73. The buffer formulation of claim 64, wherein the buffer comprises about 19 mM of glacial acetic acid.

74. The buffer formulation of claim 64, wherein the buffer comprises from about 25 mM to about 27 mM of sodium chloride.

75. The buffer formulation of claim 64, wherein the buffer comprises about 26 mM of sodium chloride.

76. The buffer formulation of claim 64, wherein the buffer comprises about 26.35 mM of sodium chloride.

77. The buffer formulation of claim 64, wherein the formulation comprises from about 0.08% (v/v) to about 0.12% (v/v) of polysorbate 80.

78. The buffer formulation of claim 64, wherein the formulation comprises from about 0.09% (v/v) to about 0.11% (v/v) of polysorbate 80.

79. The buffer formulation of claim 64, wherein the formulation comprises about 0.1% (v/v) of polysorbate 80.

80. The buffer formulation of claim 64, wherein the formulation has a pH of about 5.2.

81. The buffer formulation of claim 64, wherein the acetate salt comprises sodium acetate trihydrate.

82. The buffer formulation of claim 64, further comprising an antibody.

* * * * *

```
SEQUENCE LISTING

<160> NUMBER OF SEQ ID NOS: 9

<210> SEQ ID NO 1
<211> LENGTH: 451
<212> TYPE: PRT
<213> ORGANISM: Homo sapiens

<400> SEQUENCE: 1

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Ala Ile Thr Trp Asn Ser Gly His Ile Asp Tyr Ala Asp Ser Val
        50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240
```

```
Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 2
<211> LENGTH: 214
<212> TYPE: PRT
<213> ORGANISM: Homo sapiens

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
```

```
                145                 150                 155                 160
Glu Ser Val Thr Glu Gln Asp Ser Lys Asp Ser Thr Tyr Ser Leu Ser
                    165                 170                 175
Ser Thr Leu Thr Leu Ser Lys Ala Asp Tyr Glu Lys His Lys Val Tyr
                180                 185                 190
Ala Cys Glu Val Thr His Gln Gly Leu Ser Ser Pro Val Thr Lys Ser
            195                 200                 205
Phe Asn Arg Gly Glu Cys
            210

<210> SEQ ID NO 3
<211> LENGTH: 121
<212> TYPE: PRT
<213> ORGANISM: Homo sapiens

<400> SEQUENCE: 3

Glu Val Gln Leu Val Glu Ser Gly Gly Gly Leu Val Gln Pro Gly Arg
1               5                   10                  15
Ser Leu Arg Leu Ser Cys Ala Ala Ser Gly Phe Thr Phe Asp Asp Tyr
                20                  25                  30
Ala Met His Trp Val Arg Gln Ala Pro Gly Lys Gly Leu Glu Trp Val
            35                  40                  45
Ser Ala Ile Thr Trp Asn Ser Gly His Ile Asp Tyr Ala Asp Ser Val
        50                  55                  60
Glu Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Lys Val Ser Tyr Leu Ser Thr Ala Ser Ser Leu Asp Tyr Trp Gly
            100                 105                 110
Gln Gly Thr Leu Val Thr Val Ser Ser
        115                 120

<210> SEQ ID NO 4
<211> LENGTH: 98
<212> TYPE: PRT
<213> ORGANISM: Homo sapiens

<400> SEQUENCE: 4

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val

<210> SEQ ID NO 5
<211> LENGTH: 12
<212> TYPE: PRT
<213> ORGANISM: Homo sapiens
```

<400> SEQUENCE: 5

Glu Pro Lys Ser Cys Asp Lys Thr His Thr Cys Pro
1               5                   10

<210> SEQ ID NO 6
<211> LENGTH: 93
<212> TYPE: PRT
<213> ORGANISM: Homo sapiens

<400> SEQUENCE: 6

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
                20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
        50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys
                85                  90

<210> SEQ ID NO 7
<211> LENGTH: 127
<212> TYPE: PRT
<213> ORGANISM: Homo sapiens

<400> SEQUENCE: 7

Cys Lys Val Ser Asn Lys Ala Leu Pro Ala Pro Ile Glu Lys Thr Ile
1               5                   10                  15

Ser Lys Ala Lys Gly Gln Pro Arg Glu Pro Gln Val Tyr Thr Leu Pro
                20                  25                  30

Pro Ser Arg Asp Glu Leu Thr Lys Asn Gln Val Ser Leu Thr Cys Leu
            35                  40                  45

Val Lys Gly Phe Tyr Pro Ser Asp Ile Ala Val Glu Trp Glu Ser Asn
        50                  55                  60

Gly Gln Pro Glu Asn Asn Tyr Lys Thr Thr Pro Pro Val Leu Asp Ser
65                  70                  75                  80

Asp Gly Ser Phe Phe Leu Tyr Ser Lys Leu Thr Val Asp Lys Ser Arg
                85                  90                  95

Trp Gln Gln Gly Asn Val Phe Ser Cys Ser Val Met His Glu Ala Leu
            100                 105                 110

His Asn His Tyr Thr Gln Lys Ser Leu Ser Leu Ser Pro Gly Lys
        115                 120                 125

<210> SEQ ID NO 8
<211> LENGTH: 108
<212> TYPE: PRT
<213> ORGANISM: Homo sapiens

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
                20                  25                  30

Leu Ala Trp Tyr Gln Gln Lys Pro Gly Lys Ala Pro Lys Leu Leu Ile

```
                    35                  40                  45
Tyr Ala Ala Ser Thr Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg
            100                 105

<210> SEQ ID NO 9
<211> LENGTH: 106
<212> TYPE: PRT
<213> ORGANISM: Homo sapiens

<400> SEQUENCE: 9

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
                20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
        50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```